US012315617B2

(12) United States Patent
Shelton, IV et al.

(10) Patent No.: US 12,315,617 B2
(45) Date of Patent: May 27, 2025

(54) SURGICAL DATA PROCESSING ASSOCIATED WITH MULTIPLE SYSTEM HIERARCHY LEVELS

(71) Applicant: Cilag GmbH International, Zug (CH)

(72) Inventors: Frederick E. Shelton, IV, Hillsboro, OR (US); Aaron Chow, Cincinnati, OH (US); Kevin M. Fiebig, Cincinnati, OH (US); Shane R. Adams, Lebanon, OH (US)

(73) Assignee: Cilag GmbH International, Zug (CH)

( * ) Notice: Subject to any disclaimer, the term of this patent is extended or adjusted under 35 U.S.C. 154(b) by 265 days.

(21) Appl. No.: 18/092,056

(22) Filed: Dec. 30, 2022

(65) Prior Publication Data

US 2024/0221897 A1 Jul. 4, 2024

(51) Int. Cl.
*G16H 20/40* (2018.01)
*G06N 20/00* (2019.01)

(52) U.S. Cl.
CPC ............ *G16H 20/40* (2018.01); *G06N 20/00* (2019.01)

(58) Field of Classification Search
None
See application file for complete search history.

(56) References Cited

U.S. PATENT DOCUMENTS 9,687,230 B2 6/2017 Leimbach et al.
10,390,895 B2 8/2019 Henderson et al.
10,695,081 B2 6/2020 Shelton, IV et al.
10,842,523 B2 11/2020 Shelton, IV et al.
10,881,399 B2 1/2021 Shelton, IV et al.
(Continued)

FOREIGN PATENT DOCUMENTS

CN 108430339 A 8/2018

OTHER PUBLICATIONS

Alsallal, et al., "A Machine Learning Technique to Detect Counterfeit Medicine Based on X-Ray Fluorescence Analyser", International Conference on Computing, Electronics & Communications Engineering (ICCECE), IEEE, 2018, pp. 118-122.
(Continued)

*Primary Examiner* — Phuoc H Nguyen
(74) *Attorney, Agent, or Firm* — Condo Roccia Koptiw LLP

(57) ABSTRACT

Systems, methods, and instrumentalities may be described herein associated with data processing associated with multiple system hierarchical levels and compartmentalizing a machine learning algorithm into a plurality of parts. A surgical hub/edge device may obtain surgical data associated with a surgical task and determine sets of parameters associated with various surgical data subblocks. The surgical hub/edge device may determine processing levels to be used for processing each of the surgical data subblocks based on a capability associated with a processing device that is located in a computational hierarchy of the healthcare provider's network. The surgical hub/edge device may send the surgical data subblocks to the respective processing devices based on the parameters associated with the surgical data subblocks and the processing levels. Scaling of a surgical data attribute to be analyzed by a machine learning algorithm may be adjusted based on a resource-time relationship of a surgical hub/edge device.

16 Claims, 24 Drawing Sheets

(56) References Cited

U.S. PATENT DOCUMENTS

| | | | |
|---|---|---|---|
| 10,932,808 B2 | 3/2021 | Shelton, IV et al. | |
| 11,410,259 B2 | 8/2022 | Harris et al. | |
| 11,423,007 B2 | 8/2022 | Shelton, IV et al. | |
| 11,464,590 B1 | 10/2022 | Roh et al. | |
| 2001/0051881 A1* | 12/2001 | Filler | G16H 40/67 705/3 |
| 2008/0285626 A1 | 11/2008 | Ma et al. | |
| 2011/0112384 A1 | 5/2011 | Eisenhardt et al. | |
| 2019/0006047 A1 | 1/2019 | Gorek et al. | |
| 2019/0125455 A1 | 5/2019 | Shelton, IV et al. | |
| 2019/0201119 A1 | 7/2019 | Harris et al. | |
| 2019/0201123 A1 | 7/2019 | Shelton, IV et al. | |
| 2019/0201136 A1 | 7/2019 | Shelton, IV et al. | |
| 2019/0201144 A1 | 7/2019 | Shelton, IV et al. | |
| 2019/0205567 A1 | 7/2019 | Shelton, IV et al. | |
| 2019/0206555 A1 | 7/2019 | Morgan et al. | |
| 2019/0207857 A1 | 7/2019 | Shelton, IV et al. | |
| 2020/0015901 A1 | 1/2020 | Scheib et al. | |
| 2021/0196384 A1 | 7/2021 | Shelton, IV et al. | |
| 2021/0244290 A1* | 8/2021 | Tan | G16H 20/40 |
| 2021/0315579 A1 | 10/2021 | Shelton, IV et al. | |
| 2021/0322014 A1 | 10/2021 | Shelton, IV et al. | |
| 2021/0370790 A1 | 12/2021 | Feldman | |
| 2022/0096163 A1 | 3/2022 | Payyavula et al. | |
| 2022/0104822 A1 | 4/2022 | Shelton, IV et al. | |
| 2022/0238216 A1 | 7/2022 | Shelton, IV et al. | |
| 2022/0331047 A1 | 10/2022 | Shelton, IV et al. | |
| 2022/0370138 A1 | 11/2022 | Shelton, IV et al. | |
| 2023/0057949 A1* | 2/2023 | Tallent | G16H 40/20 |
| 2023/0377709 A1 | 11/2023 | Shelton, IV et al. | |
| 2024/0112768 A1 | 4/2024 | Shelton, IV et al. | |
| 2024/0216065 A1 | 7/2024 | Shelton, IV et al. | |
| 2024/0216081 A1 | 7/2024 | Shelton, IV et al. | |
| 2024/0220763 A1 | 7/2024 | Shelton, IV et al. | |
| 2024/0221878 A1 | 7/2024 | Shelton, IV et al. | |
| 2024/0221892 A1 | 7/2024 | Shelton, IV et al. | |
| 2024/0221893 A1 | 7/2024 | Shelton, IV et al. | |
| 2024/0221894 A1 | 7/2024 | Shelton, IV et al. | |
| 2024/0221895 A1 | 7/2024 | Shelton, IV et al. | |
| 2024/0221896 A1 | 7/2024 | Shelton, IV et al. | |
| 2024/0221923 A1 | 7/2024 | Shelton, IV et al. | |
| 2024/0221924 A1 | 7/2024 | Shelton, IV et al. | |
| 2024/0221931 A1 | 7/2024 | Shelton, IV et al. | |
| 2024/0221937 A1 | 7/2024 | Shelton, IV et al. | |
| 2024/0221960 A1 | 7/2024 | Shelton, IV et al. | |
| 2025/0000510 A1* | 1/2025 | Creamer | A61B 17/072 |

OTHER PUBLICATIONS

Anonymous, "Cloud computing", Wikipedia, the free encyclopedia, Dec. 22, 2022, pp. 1-24.

Asadizanjani, et al., "Counterfeit Electronics Detection Using Image Processing and Machine Learning", Journal of Physics Conference Series, vol. 787, 2017, pp. 1-6.

* cited by examiner

SURGICAL DATA PROCESSING ASSOCIATED WITH MULTIPLE SYSTEM HIERARCHY LEVELS

CROSS-REFERENCE TO RELATED APPLICATIONS

This application is related to the following, filed contemporaneously, the contents of each of which are incorporated by reference herein:

U.S. patent application Ser. No. 18/092,025, titled A METHOD FOR ADVANCED ALGORITHM SUPPORT;

U.S. patent application Ser. No. 18/092,047, titled SURGICAL DATA PROCESSING ASSOCIATED WITH MULTIPLE SYSTEM HEIRARCHY LEVELS.

BACKGROUND

Patient care is generally improved when tailored to the individual. Every person has different needs, so surgical and interventional solutions that center on the unique journey of every patient may represent efficient, groundbreaking pathways to healing. At the same time, the high stakes of patient care, in particular surgical processes, often drive a focus on conservative, repeatable activities.

Innovative medical technology, such as advanced surgical support computing systems and intelligent surgical instruments for example, may improve approaches to patient care and address the particular needs of health care providers.

The ever-increasing availability data and computing resources have made non-traditional algorithms, such as machine learning algorithms, a specific technical opportunity in health care systems. But incorporating such non-traditional algorithms into any medical technology presents many challenges.

SUMMARY

Systems, methods, and instrumentalities may be described herein associated with allometry (e.g., growth and/or decay) of surgical data as it moves up or down various hierarchical levels. A surgical device (e.g., a surgical hub) may receive a plurality of surgical data parameters associated with a first patient. The plurality of surgical data parameters may be of a first data magnitude (e.g., a first data size) and of a first data individuality level.

The surgical device may identify a processing device for processing the plurality of surgical data parameters. The processing device may be identified based on the first data magnitude, first data individuality level and/or characteristics of the processing server, and/or a rule set.

The surgical device may transform the plurality of surgical data parameters into a transformed plurality of surgical data parameters such that the transformed plurality of surgical data parameters is of a second surgical data individuality level and a second surgical data magnitude. The transformation of the plurality of surgical data parameters may include anonymization of a subset of the plurality of surgical data parameters. The anonymization may include at least one of redaction, randomization, aggregation, setting a range, or averaging. The transformed plurality of surgical data parameters may be sent for processing to the identified processing device.

Systems, methods, and instrumentalities may be described herein associated with surgical data processing at various system hierarchical levels. A surgical hub/edge server may obtain surgical data associated with a surgical task. The surgical data may include a data magnitude and a data form data individuality level. The data magnitude may be the extent the portion of the surgical data is to be processed. The data form may be the individuality level of the portion of the surgical data to be processed. The surgical hub/edge device may determine sets of parameters associated with a first surgical data subblock of the surgical data and a second surgical subblock of the surgical data. For example, the surgical hub/edge device may determine a first set of parameters associated with a first surgical data subblock of the surgical data and a second set of parameters associated with a second surgical data subblock of the surgical data.

The surgical hub/edge device may determine processing levels to be used for processing each of the first subblock of the surgical data and the second subblock of the surgical data. For example, the surgical hub/edge device may determine a first processing level to be used for processing the first surgical data subblock. The first processing level may be obtained based on a first capability associated with a first processing device located in a first computational hierarchal level of a healthcare provider's network. The surgical hub/edge device may also determine a second processing level to be used for processing the second surgical data subblock. The second processing level may be obtained based on a second capability associated with a second processing device located in a second computational hierarchy of the healthcare provider's network.

The surgical hub/edge device may send the first surgical data subblock to the first processing device, for example, based on at least one of the first set of parameters associated with the first surgical data subblock and the first processing level. The first set of parameters associated with the first surgical data subblock may include, for example, a first surgical data magnitude associated with the first surgical data subblock, a first data granularity associated with the first surgical data subblock, a timeliness of a result associated with the first surgical data subblock.

The surgical hub/edge device may send the second subblock to the second processing device, for example, based on at least one of the second set of parameters associated with the second surgical data subblock and second first processing level. The second set of parameters associated with the second surgical data subblock may include, for example, a second surgical data magnitude associated with the second surgical data subblock, a second data granularity associated with the second surgical data subblock, a timeliness of a result associated with the second surgical data subblock.

Systems, methods, and instrumentalities may be described herein associated with adjusting/scaling of at least one surgical data attribute to be analyzed by a machine learning (ML) algorithm based on a resource-time relationship associated with a computing resource. The resource-time relationship may be determined based on at least one of timeliness of a needed result, computational processing level associated with the surgical computing device, or a computational memory associated with the surgical computing device, a network bandwidth between the surgical computing device and where the needed result it to be sent, one or more communication parameters, risk level of functioning without obtaining the needed result, importance level of the surgical data or a surgical task associated with the surgical task, or availability of other data that may be used as a substitution. The communication parameters may include a throughput rate at the surgical computing device or a latency between the surgical computing device and where the needed result is to be sent.

The at least one surgical data attribute comprises a size of the surgical data, a number of surgical data variables, a frequency associated with the surgical data, an accuracy level associated with the surgical data, an ML algorithm type, a tolerable error associated with the ML algorithm, a number of stacking levels associated with the ML algorithm, or verification or checking of results.

Scaling or adjusting at least one attribute associated with the ML algorithm may performed be based on balance of a level of a needed result, a time associated with the needed result, and availability of the computing resource within the time associated with the needed result.

DETAILED DESCRIPTION

Figure 1:
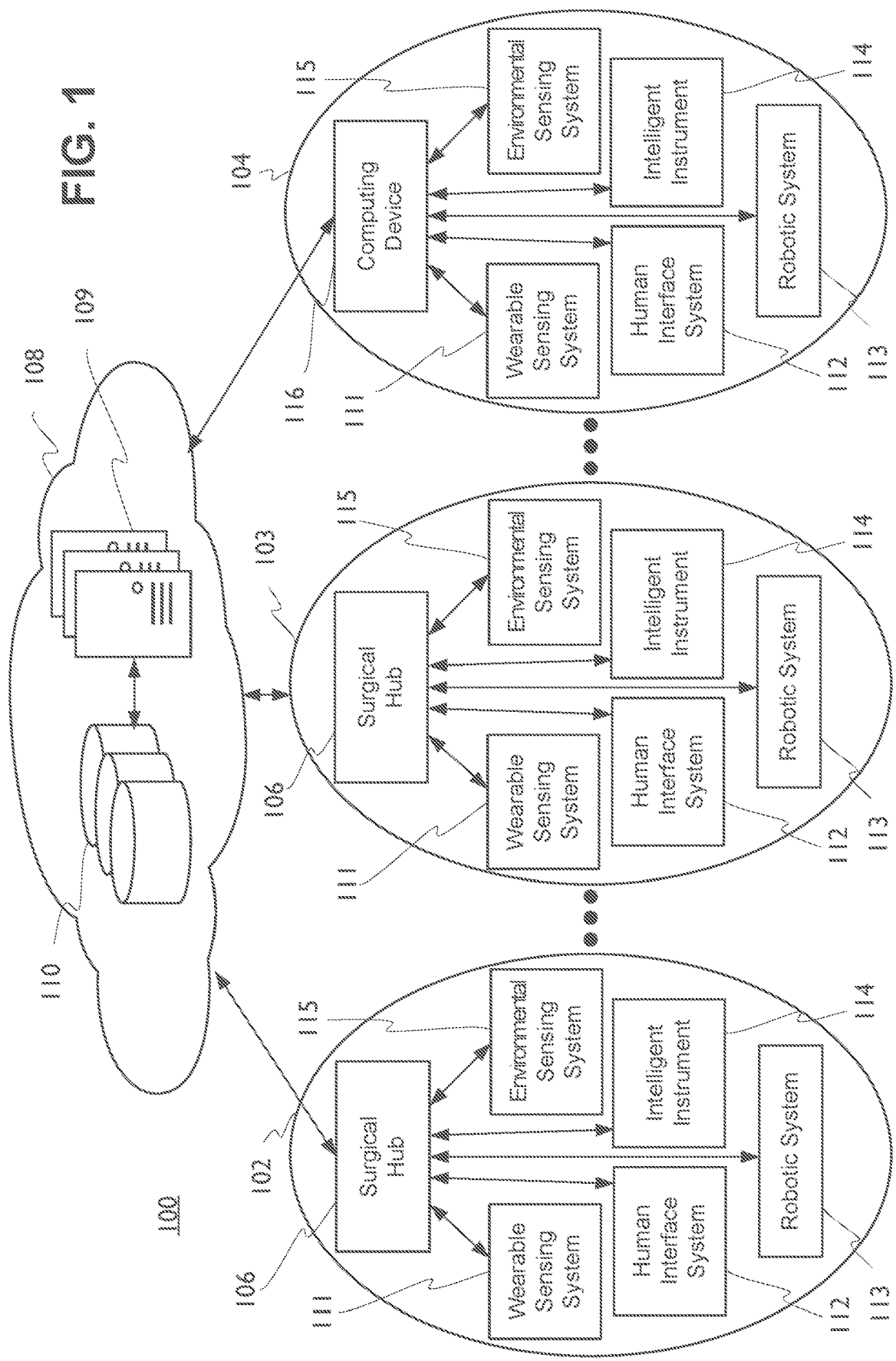
FIG. 1 is a block diagram of a computer-implemented surgical system.

FIG. 1 is a block diagram of a computer-implemented surgical system 100. An example surgical system, such as the surgical system 100, may include one or more surgical systems (e.g., surgical sub-systems) 102, 103, 104. For example, surgical system 102 may include a computer-implemented interactive surgical system. For example, surgical system 102, 103, 104 may include a surgical computing system, such as surgical hub 106 and/or computing device 116, in communication with a cloud computing system 108. The cloud computing system 108 may include a cloud server 109 and a cloud storage unit 110.

Surgical systems 102, 103, 104 may each computer-enabled surgical equipment and devices. For example, surgical systems 102, 103, 104 may include a wearable sensing system 111, a human interface system 112, a robotic system 113, one or more intelligent instruments 114, environmental sensing system 115, and/or the like. The wearable sensing system 111 may include one or more devices used to sense aspects of individuals status and activity within a surgical environment. For example, the wearable sensing system 111 may include health care provider sensing systems and/or patient sensing systems.

The human interface system 112 may include devices that enable an individual to interact with the surgical system 102, 103, 104 and/or the cloud computing system 108. The human interface system 112 may include a human interface device.

The robotic system 113 may include surgical robotic devices, such a surgical robot. The robotic system 113 may enable robotic surgical procedures. The robotic system 113 may receive information, settings, programming, controls and the like from the surgical hub 106 for example, the robotic system 113 may send data, such as sensor data, feedback information, video information, operational logs, and the like to the surgical hub 106.

Figure 2:
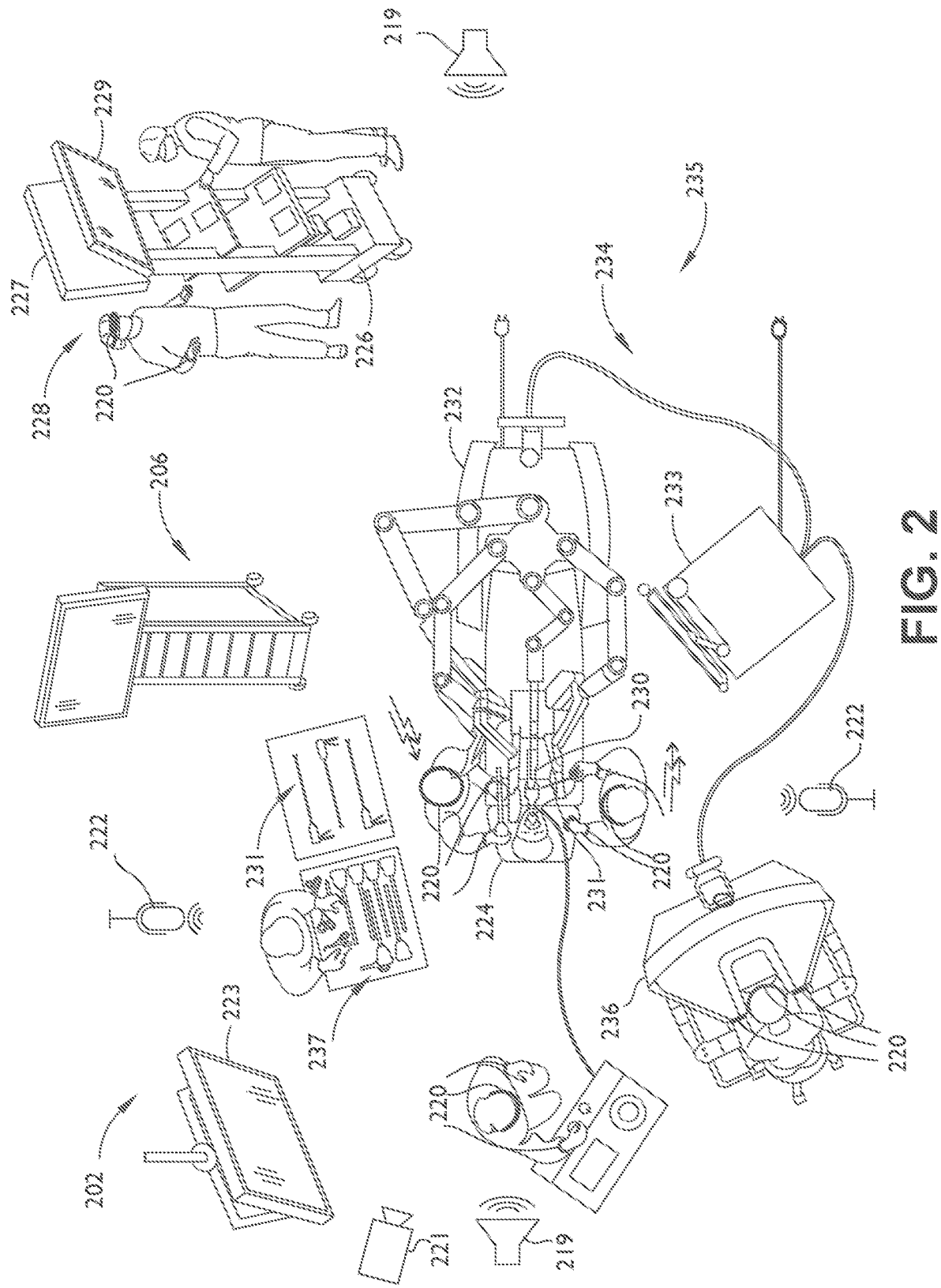
FIG. 2 shows an example surgical system in a surgical operating room.

The environmental sensing system 115 may include one or more devices, for example, used for measuring one or more environmental attributes, for example, as further described in FIG. 2. The robotic system 113 may include a plurality of devices used for performing a surgical procedure, for example, as further described in FIG. 2.

The surgical system 102 may be in communication with a remote server 109 that may be part of a cloud computing system 108. In an example, the surgical system 102 may be in communication with a remote server 109 via networked connection, such an internet connection (e.g., business internet service, T3, cable/FIOS networking node, and the like). The surgical system 102 and/or a component therein may communicate with the remote servers 109 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, the surgical hub 106 may facilitate displaying the image from an surgical imaging device, like a laparoscopic scope for example. The surgical hub 106 have cooperative interactions with the other local systems to facilitate displaying information relevant to those local systems. The surgical hub 106 may interact with one or more sensing systems 111, 115, one or more intelligent instruments 114, and/or multiple displays. For example, the surgical hub 106 may be configured to gather measurement data from the one or more sensing systems 111, 115 and send notifications or control messages to the one or more sensing systems 111, 115. The surgical hub 106 may send and/or receive information including notification information to and/or from the human interface system 112. The human interface system 112 may include one or more human interface devices (HIDs). The surgical hub 106 may send and/or receive notification information or control information to audio, display and/or control information to various devices that are in communication with the surgical hub.

For example, the sensing systems 111, 115 may include the wearable sensing system 111 (which may include one or more HCP sensing systems and one or more patient sensing systems) and the environmental sensing system 115. The one or more sensing systems 111, 115 may measure data relating to various biomarkers. The one or more sensing systems 111, 115 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 111, 115 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 100, for example. The information from the biomarkers may be determined and/or used by the computer-implemented patient and the surgical system 100 to improve said systems and/or to improve patient outcomes, for example. The one or more sensing systems 111, 115, biomarkers, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

FIG. 2 shows an example of a surgical system 202 in a surgical operating room. As illustrated in FIG. 2, a patient is being operated on by one or more health care professionals (HCPs). The HCPs are being monitored by one or more HCP sensing systems 220 worn by the HCPs. The HCPs and the environment surrounding the HCPs may also be monitored by one or more environmental sensing systems including, for example, a set of cameras 221, a set of microphones 222, and other sensors that may be deployed in the operating room. The HCP sensing systems 220 and the environmental sensing systems may be in communication with a surgical hub 206, which in turn may be in communication with one or more cloud servers 209 of the cloud computing system 208, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 223 and one or more audio output devices (e.g., speakers 219) are positioned in the sterile field to be visible to an operator at the operating table 224. In addition, a visualization/notification tower 226 is positioned outside the sterile field. The visualization/notification tower 226 may include a first non-sterile human interactive device (HID) 227 and a second non-sterile HID 229, which may face away from each other. The HID may be a display or a display with a touchscreen allowing a human to interface directly with the HID. A human interface system, guided by the surgical hub 206, may be configured to utilize the HIDs 227, 229, and 223 to coordinate information flow to operators inside and outside the sterile field. In an example, the surgical hub 206 may cause an HID (e.g., the primary HID 223) to display a notification and/or information about the patient and/or a surgical procedure step. In an example, the surgical hub 206 may prompt for and/or receive input from personnel in the sterile field or in the non-sterile area. In an example, the surgical hub 206 may cause an HID to display a snapshot of a surgical site, as recorded by an imaging device 230, on a non-sterile HID 227 or 229, while maintaining a live feed of the surgical site on the primary HID 223. The snapshot on the non-sterile display 227 or 229 can permit a non-sterile operator to perform a diagnostic step relevant to the surgical procedure, for example.

In one aspect, the surgical hub 206 may be configured to route a diagnostic input or feedback entered by a non-sterile operator at the visualization tower 226 to the primary display 223 within the sterile field, where it can be viewed by a sterile operator at the operating table. In one example, the input can be in the form of a modification to the snapshot displayed on the non-sterile display 227 or 229, which can be routed to the primary display 223 by the surgical hub 206.

Referring to FIG. 2, a surgical instrument 231 is being used in the surgical procedure as part of the surgical system 202. The hub 206 may be configured to coordinate information flow to a display of the surgical instrument 231. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 226 can be routed by the hub 206 to the surgical instrument display within the sterile field, where it can be viewed by the operator of the surgical instrument 231. Example surgical instruments that are suitable for use with the surgical system 202 are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 202 being used to perform a surgical procedure on a patient who is lying down on an operating table 224 in a surgical operating room 235. A robotic system 234 may be used in the surgical procedure as a part of the surgical system 202. The robotic system 234 may include a surgeon's console 236, a patient side cart 232 (surgical robot), and a surgical robotic hub 233. The patient side cart 232 can manipulate at least one removably coupled surgical tool 237 through a minimally invasive incision in the body of the patient while the surgeon views the surgical site through the surgeon's console 236. An image of the surgical site can be obtained by a medical imaging device 230, which can be manipulated by the patient side cart 232 to orient the imaging device 230. The robotic hub 233 can be used to process the images of the surgical site for subsequent display to the surgeon through the surgeon's console 236.

Other types of robotic systems can be readily adapted for use with the surgical system 202. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 208, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 230 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 230 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 230 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 230 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 211 illustrated in FIG. 1 may include one or more sensing systems, for example, HCP sensing systems 220 as shown in FIG. 2. The HCP sensing systems 220 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 220 may measure a set of biomarkers to monitor the heart rate of an HCP. In an example, a sensing system 220) worn on a surgeon's wrist (e.g., a watch or a wristband) may use an accelerometer to detect hand motion and/or shakes and determine the magnitude and frequency of tremors. The sensing system 220 may send the measurement data associated with the set of biomarkers and the data associated with a physical state of the surgeon to the surgical hub 206 for further processing. One or more environmental sensing devices may send environmental information to the surgical hub 206. For example, the environmental sensing devices may include a camera 221 for detecting hand/body position of an HCP. The environmental sensing devices may include microphones 222 for measuring the ambient noise in the surgical theater. Other environmental sensing devices may include devices, for example, a thermometer to measure temperature and a hygrometer to measure humidity of the surroundings in the surgical theater, etc. The surgical hub 206, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 220 may measure one or more surgeon biomarkers associated with an HCP and send the measurement data associated with the surgeon biomarkers to the surgical hub 206. The HCP sensing systems 220 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 206 may use the surgeon biomarker measurement data associated with an HCP to adaptively control one or more surgical instruments 231. For example, the surgical hub 206 may send a control program to a surgical instrument 231 to control its actuators to limit or compensate for fatigue and use of fine motor skills. The surgical hub 206 may send the control program based on situational awareness and/or the context on importance or criticality of a task. The control program may instruct the instrument to alter operation to provide more control when control is needed.

Figure 3:
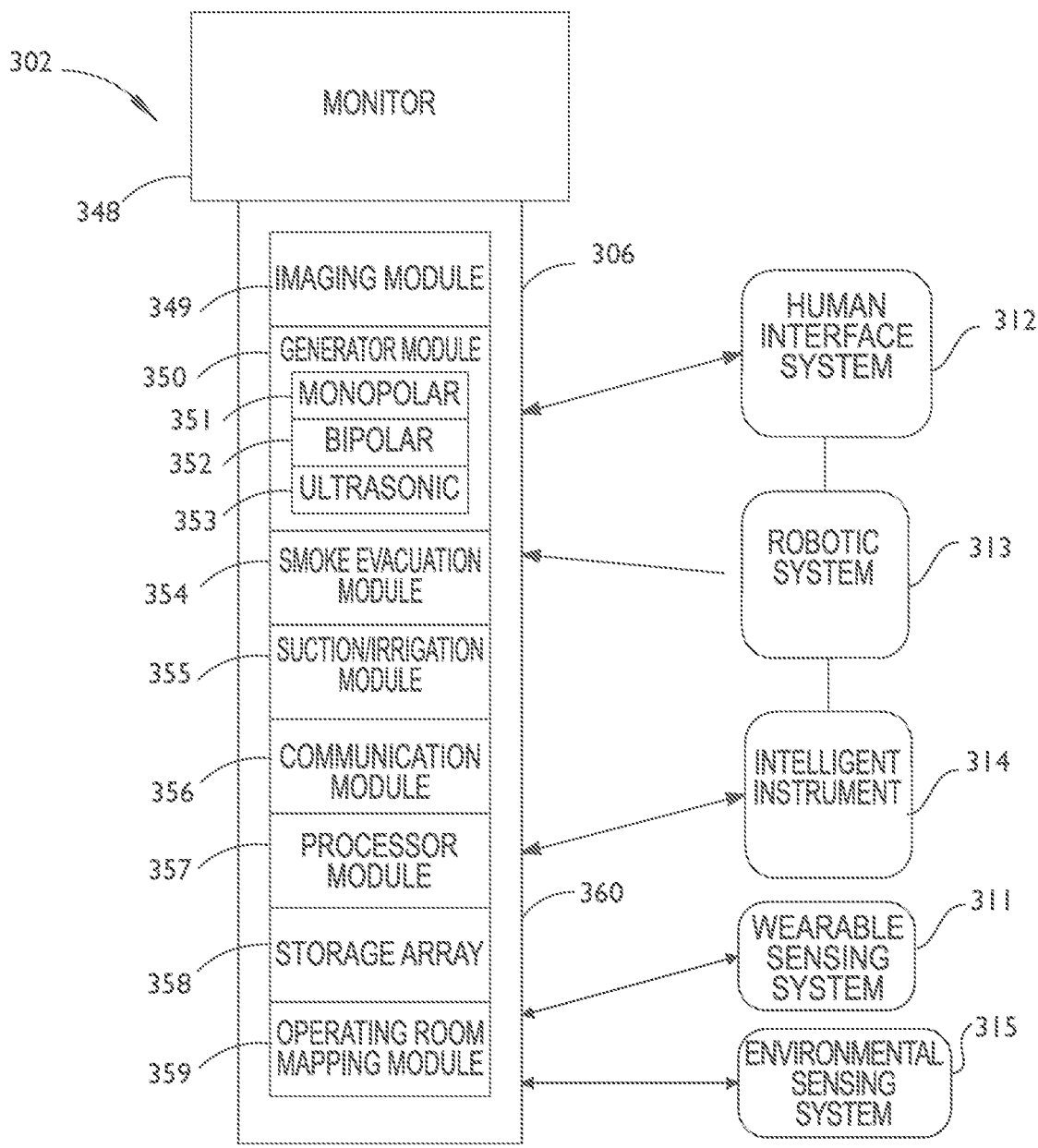
FIG. 3 illustrates an example surgical hub paired with various systems.

FIG. 3 shows an example surgical system 302 with a surgical hub 306. The surgical hub 306 may be paired with, via a modular control, a wearable sensing system 311, an environmental sensing system 315, a human interface system 312, a robotic system 313, and an intelligent instrument 314. The hub 306 includes a display 348, an imaging module 349, a generator module 350, a communication module 356, a processor module 357, a storage array 358, and an operating-room mapping module 359. In certain aspects, as illustrated in FIG. 3, the hub 306 further includes a smoke evacuation module 354 and/or a suction/irrigation module 355. The various modules and systems may be connected to the modular control either directly via a router or via the communication module 356. The operating theater devices may be coupled to cloud computing resources and data storage via the modular control. The human interface system 312 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 360 offers a unified environment for managing the power, data, and fluid lines, which reduces the frequency of entanglement between such lines. Aspects of the present disclosure present a surgical hub 306 for use in a surgical procedure that involves energy application to tissue at a surgical site.

The surgical hub 306 includes a hub enclosure 360 and a combo generator module slidably receivable in a docking station of the hub enclosure 360. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 355 slidably received in the hub enclosure 360. In one aspect, the hub enclosure 360 may include a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 360 is configured to accommodate different generators and facilitate an interactive communication therebetween. The hub modular enclosure 360 may enable the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 360 that allows the modular integration of a generator module 350, a smoke evacuation module 354, and a suction/irrigation module 355. The hub modular enclosure 360 further facilitates interactive communication between the modules 359, 354, and 355. The generator module 350 can be with integrated monopolar, bipolar, and ultrasonic components supported in a single housing unit slidably insertable into the hub modular enclosure 360. The generator module 350 can be configured to connect to a monopolar device 351, a bipolar device 352, and an ultrasonic device 353. Alternatively, the generator module 350 may comprise a series of monopolar, bipolar, and/or ultrasonic generator modules that interact through the hub modular enclosure 360. The hub modular enclosure 360 can be configured to facilitate the insertion of multiple generators and interactive communication between the generators docked into the hub modular enclosure 360 so that the generators would act as a single generator.

Figure 4:
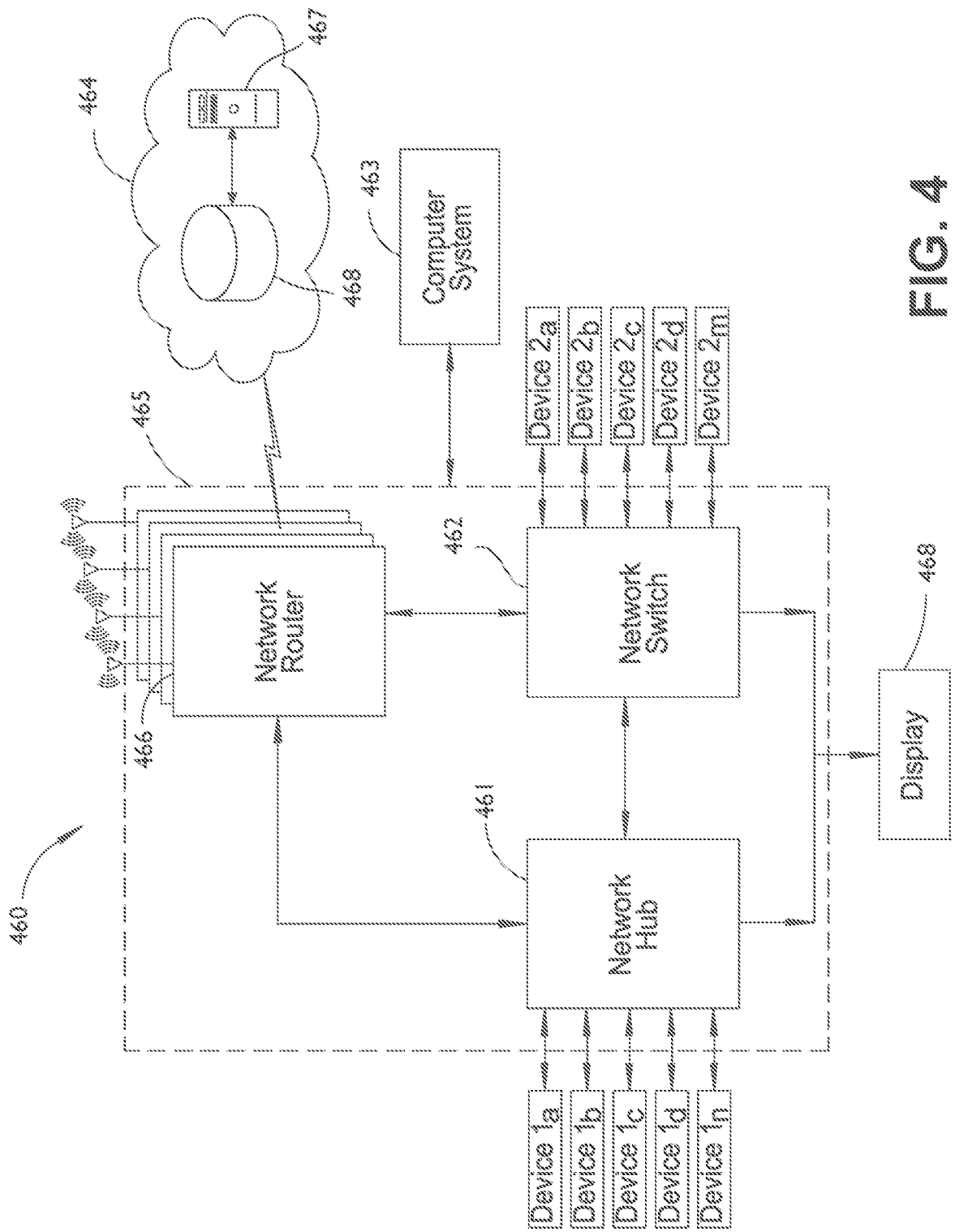
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 460 may include a modular communication hub 465 that is configured to connect modular devices located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system 463 to provide local computer processing and data manipulation.

The computer system 463 may comprise a processor and a network interface. The processor may be coupled to a communication module, storage, memory, non-volatile memory, and input/output (I/O) interface via a system bus. The system bus can be any of several types of bus structure (s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with Stellaris Ware® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 463 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 463 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system 463 and to output information from the computer system 463 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 463 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 463 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 463, it can also be external to the computer system 463. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 460 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 461 or network switch 462. An intelligent surgical data network may be referred to as a manageable hub or switch. A switching hub reads the destination address of each packet and then forwards the packet to the correct port.

Modular devices 1a-1n located in the operating theater may be coupled to the modular communication hub 465. The network hub 461 and/or the network switch 462 may be coupled to a network router 466 to connect the devices 1a-1n to the cloud computing system 464 or the local computer system 463. Data associated with the devices 1a-1n may be transferred to cloud-based computers via the router for remote data processing and manipulation. Data associated with the devices 1a-1n may also be transferred to the local computer system 463 for local data processing and manipulation. Modular devices 2a-2m located in the same operating theater also may be coupled to a network switch 462. The network switch 462 may be coupled to the network hub 461 and/or the network router 466 to connect the devices 2a-2m to the cloud 464. Data associated with the devices 2a-2m may be transferred to the cloud computing system 464 via the network router 466 for data processing and manipulation. Data associated with the devices 2a-2m may also be transferred to the local computer system 463 for local data processing and manipulation.

As illustrated in FIG. 4 a computing system, such as a surgical hub system 460, may include a modular communication hub 465 that is configured to connect modular devices (e.g., surgical devices) located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system 463 (e.g., a computing device) to provide local computer processing and data manipulation.

Figure 5:
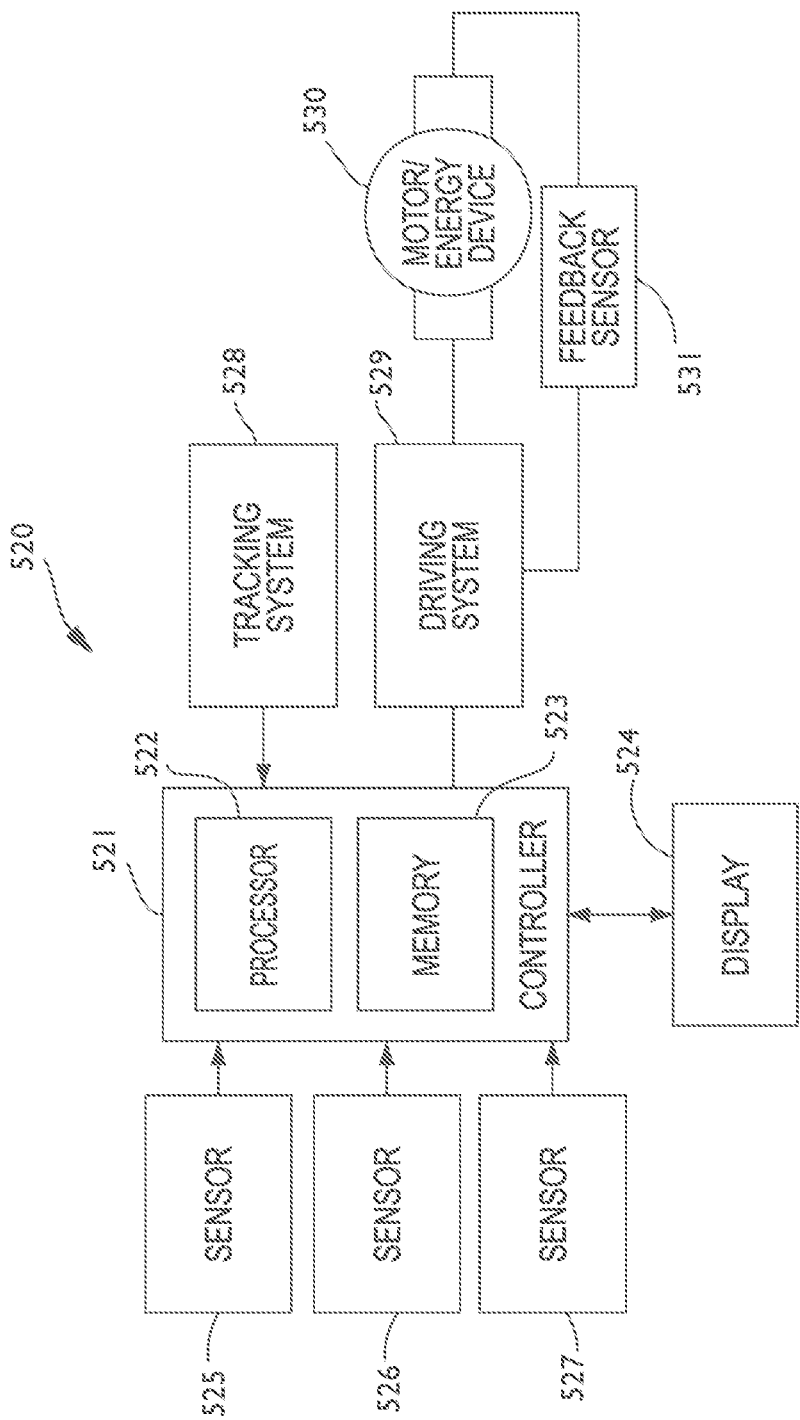
FIG. 5 illustrates a logic diagram of a control system of a surgical instrument.

FIG. 5 illustrates a logical diagram of a control system 520 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 520 may comprise a control circuit. The control circuit may include a microcontroller 521 comprising a processor 522 and a memory 523. One or more of sensors 525, 526, 527, for example, provide real-time feedback to the processor 522. A motor 530, driven by a motor driver 529, operably couples a longitudinally movable displacement member to drive the I-beam knife element. A tracking system 528 may be configured to determine the position of the longitudinally movable displacement member. The position information may be provided to the processor 522, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 524 may display a variety of operating conditions of the instruments and may include touch screen functionality for data input. Information displayed on the display 524 may be overlaid with images acquired via endoscopic imaging modules.

The microcontroller 521 may be any single-core or multicore processor such as those known under the trade name ARM Cortex by Texas Instruments. In one aspect, the main microcontroller 521 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle SRAM, and internal ROM loaded with Stellaris Ware® software, a 2 KB EEPROM, one or more PWM modules, one or more QEI analogs, and/or one or more 12-bit ADCs with 12 analog input channels, details of which are available for the product datasheet.

The microcontroller 521 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 521 may be programmed to perform various functions such as precise control over the speed and position of the knife and articulation systems. In one aspect, the microcontroller 521 may include a processor 522 and a memory 523. The electric motor 530 may be a brushed direct current (DC) motor with a gearbox and mechanical links to an articulation or knife system. In one aspect, a motor driver 529 may be an A3941 available from Allegro Microsystems, Inc. Other motor drivers may be readily substituted for use in the tracking system 528 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 521 may be programmed to provide precise control over the speed and position of displacement members and articulation systems. The microcontroller 521 may be configured to compute a response in the software of the microcontroller 521. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 530 may be controlled by the motor driver 529 and can be employed by the firing system of the surgical instrument or tool. In various forms, the motor 530 may be a brushed DC driving motor having a maximum rotational speed of approximately 25,000 RPM. In some examples, the motor 530 may include a brushless motor, a cordless motor, a synchronous motor, a stepper motor, or any other suitable electric motor. The motor driver 529 may comprise an H-bridge driver comprising field-effect transistors (FETs), for example. The motor 530 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 529 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 529 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 528 comprising an absolute positioning system.

The tracking system 528 may comprise a controlled motor drive circuit arrangement comprising a position sensor 525 according to one aspect of this disclosure. The position sensor 525 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 525 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 530 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 525 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 525 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 525 completing one or more revolutions for the full stroke of the displacement member. The position sensor 525 may complete multiple revolutions for the full stroke of the displacement member.

A series of switches, where n is an integer greater than one, may be employed alone or in combination with a gear reduction to provide a unique position signal for more than one revolution of the position sensor 525. The state of the switches may be fed back to the microcontroller 521 that applies logic to determine a unique position signal corresponding to the longitudinal linear displacement d1+d2+ . . . dn of the displacement member. The output of the position sensor 525 is provided to the microcontroller 521. The position sensor 525 of the sensor arrangement may comprise a magnetic sensor, an analog rotary sensor like a potentiometer, or an array of analog Hall-effect elements, which output a unique combination of position signals or values.

The position sensor 525 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 525 for the tracking system 528 comprising an absolute positioning system may comprise a magnetic rotary absolute positioning system. The position sensor 525 may be implemented as an AS5055EQFT single-chip magnetic rotary position sensor available from Austria Microsystems, AG. The position sensor 525 is interfaced with the microcontroller 521 to provide an absolute positioning system. The position sensor 525 may be a low-voltage and low-power component and may include four Hall-effect elements in an area of the position sensor 525 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 521. The position sensor 525 may provide 12 or 14 bits of resolution. The position sensor 525 may be an AS5055 chip provided in a small QFN 16-pin 4×4×0.85 mm package.

The tracking system 528 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 525. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 530 has taken to infer the position of a device actuator, drive bar, knife, or the like.

A sensor 526, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 522. Alternatively, or in addition to the sensor 526, a sensor 527, such as, for example, a load sensor, can measure the closure force applied by the closure drive system to the anvil. The sensor 527, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 531 can be employed to measure the current drawn by the motor 530. The force required to advance the firing member can correspond to the current drawn by the motor 530, for example. The measured force may be converted to a digital signal and provided to the processor 522.

For example, the strain gauge sensor 526 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 526, such as, for example, a micro-strain gauge, that can be configured to measure one or more parameters of the end effector, for example. In one aspect, the strain gauge sensor 526 can measure the amplitude or magnitude of the strain exerted on a jaw member of an end effector during a clamping operation, which can be indicative of the tissue compression. The measured strain can be converted to a digital signal and provided to a processor 522 of the microcontroller 521. A load sensor 527 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 522.

The measurements of the tissue compression, the tissue thickness, and/or the force required to close the end effector on the tissue, as respectively measured by the sensors 526, 527, can be used by the microcontroller 521 to characterize the selected position of the firing member and/or the corresponding value of the speed of the firing member. In one instance, a memory 523 may store a technique, an equation, and/or a lookup table which can be employed by the microcontroller 521 in the assessment.

The control system 520 of the surgical instrument or tool also may comprise wired or wireless communication circuits to communicate with a surgical hub, such as surgical hub 460 for example, as shown in FIG. 4.

Figure 6:
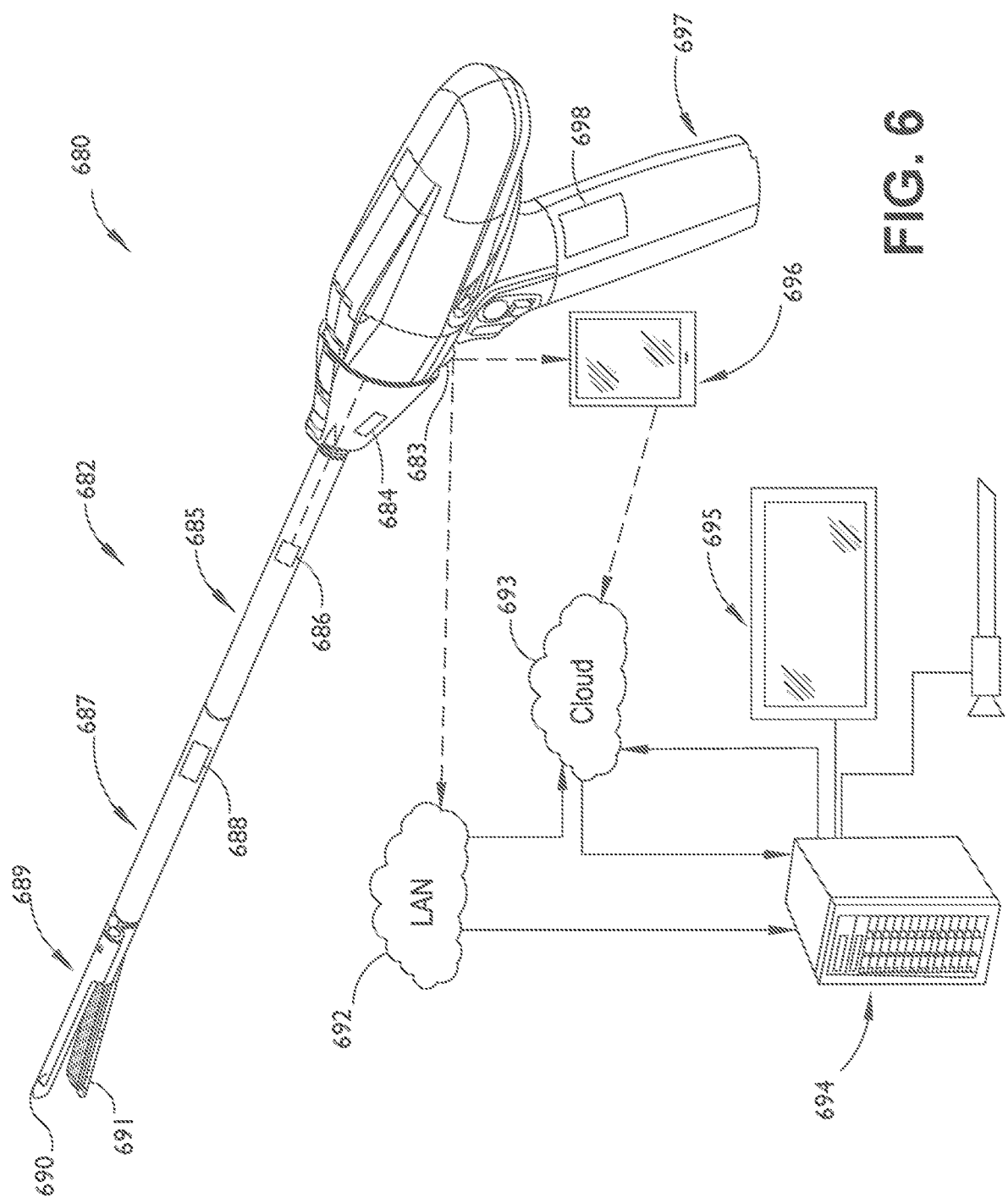
FIG. 6 shows an example surgical system that includes a handle having a controller and a motor, an adapter releasably coupled to the handle, and a loading unit releasably coupled to the adapter.

FIG. 6 illustrates an example surgical system 680 in accordance with the present disclosure and may include a surgical instrument 682 that can be in communication with a console 694 or a portable device 696 through a local area network 692 and/or a cloud network 693 via a wired and/or wireless connection. The console 694 and the portable device 696 may be any suitable computing device. The surgical instrument 682 may include a handle 697, an adapter 685, and a loading unit 687. The adapter 685 releasably couples to the handle 697 and the loading unit 687 releasably couples to the adapter 685 such that the adapter 685 transmits a force from a drive shaft to the loading unit 687. The adapter 685 or the loading unit 687 may include a force gauge (not explicitly shown) disposed therein to measure a force exerted on the loading unit 687. The loading unit 687 may include an end effector 689 having a first jaw 691 and a second jaw 690. The loading unit 687 may be an in-situ loaded or multi-firing loading unit (MFLU) that allows a clinician to fire a plurality of fasteners multiple times without requiring the loading unit 687 to be removed from a surgical site to reload the loading unit 687.

The first and second jaws 691, 690 may be configured to clamp tissue therebetween, fire fasteners through the clamped tissue, and sever the clamped tissue. The first jaw 691 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 690 may include an anvil that deforms or otherwise secures the fasteners, as the fasteners are ejected from the multi-fire fastener cartridge.

The handle 697 may include a motor that is coupled to the drive shaft to affect rotation of the drive shaft. The handle 697 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 697 may be in communication with a controller 698 of the handle 697 to selectively activate the motor to affect rotation of the drive shafts. The controller 698 may be disposed within the handle 697 and may be configured to receive input from the control interface and adapter data from the adapter 685 or loading unit data from the loading unit 687. The controller 698 may analyze the input from the control interface and the data received from the adapter 685 and/or loading unit 687 to selectively activate the motor. The handle 697 may also include a display that is viewable by a clinician during use of the handle 697. The display may be configured to display portions of the adapter or loading unit data before, during, or after firing of the instrument 682.

The adapter 685 may include an adapter identification device 684 disposed therein and the loading unit 687 may include a loading unit identification device 688 disposed therein. The adapter identification device 684 may be in communication with the controller 698, and the loading unit identification device 688 may be in communication with the controller 698. It will be appreciated that the loading unit identification device 688 may be in communication with the adapter identification device 684, which relays or passes communication from the loading unit identification device 688 to the controller 698.

The adapter 685 may also include a plurality of sensors 686 (one shown) disposed thereabout to detect various conditions of the adapter 685 or of the environment (e.g., if the adapter 685 is connected to a loading unit, if the adapter 685 is connected to a handle, if the drive shafts are rotating, the torque of the drive shafts, the strain of the drive shafts, the temperature within the adapter 685, a number of firings of the adapter 685, a peak force of the adapter 685 during firing, a total amount of force applied to the adapter 685, a peak retraction force of the adapter 685, a number of pauses of the adapter 685 during firing, etc.). The plurality of sensors 686 may provide an input to the adapter identification device 684 in the form of data signals. The data signals of the plurality of sensors 686 may be stored within or be used to update the adapter data stored within the adapter identification device 684. The data signals of the plurality of sensors 686 may be analog or digital. The plurality of sensors 686 may include a force gauge to measure a force exerted on the loading unit 687 during firing.

The handle 697 and the adapter 685 can be configured to interconnect the adapter identification device 684 and the loading unit identification device 688 with the controller 698 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 684 and the controller 698 may be in wireless communication with one another via a wireless connection separate from the electrical interface.

The handle 697 may include a transceiver 683 that is configured to transmit instrument data from the controller 698 to other components of the system 680 (e.g., the LAN 20292, the cloud 693, the console 694, or the portable device 696). The controller 698 may also transmit instrument data and/or measurement data associated with one or more sensors 686 to a surgical hub. The transceiver 683 may receive data (e.g., cartridge data, loading unit data, adapter data, or other notifications) from the surgical hub 670. The transceiver 683 may receive data (e.g., cartridge data, loading unit data, or adapter data) from the other components of the system 680. For example, the controller 698 may transmit instrument data including a serial number of an attached adapter (e.g., adapter 685) attached to the handle 697, a serial number of a loading unit (e.g., loading unit 687) attached to the adapter 685, and a serial number of a multi-fire fastener cartridge loaded into the loading unit to the console 694. Thereafter, the console 694 may transmit data (e.g., cartridge data, loading unit data, or adapter data) associated with the attached cartridge, loading unit, and adapter, respectively, back to the controller 698. The controller 698 can display messages on the local instrument display or transmit the message, via transceiver 683, to the console 694 or the portable device 696 to display the message on the display 695 or portable device screen, respectively.

Figure 7A:
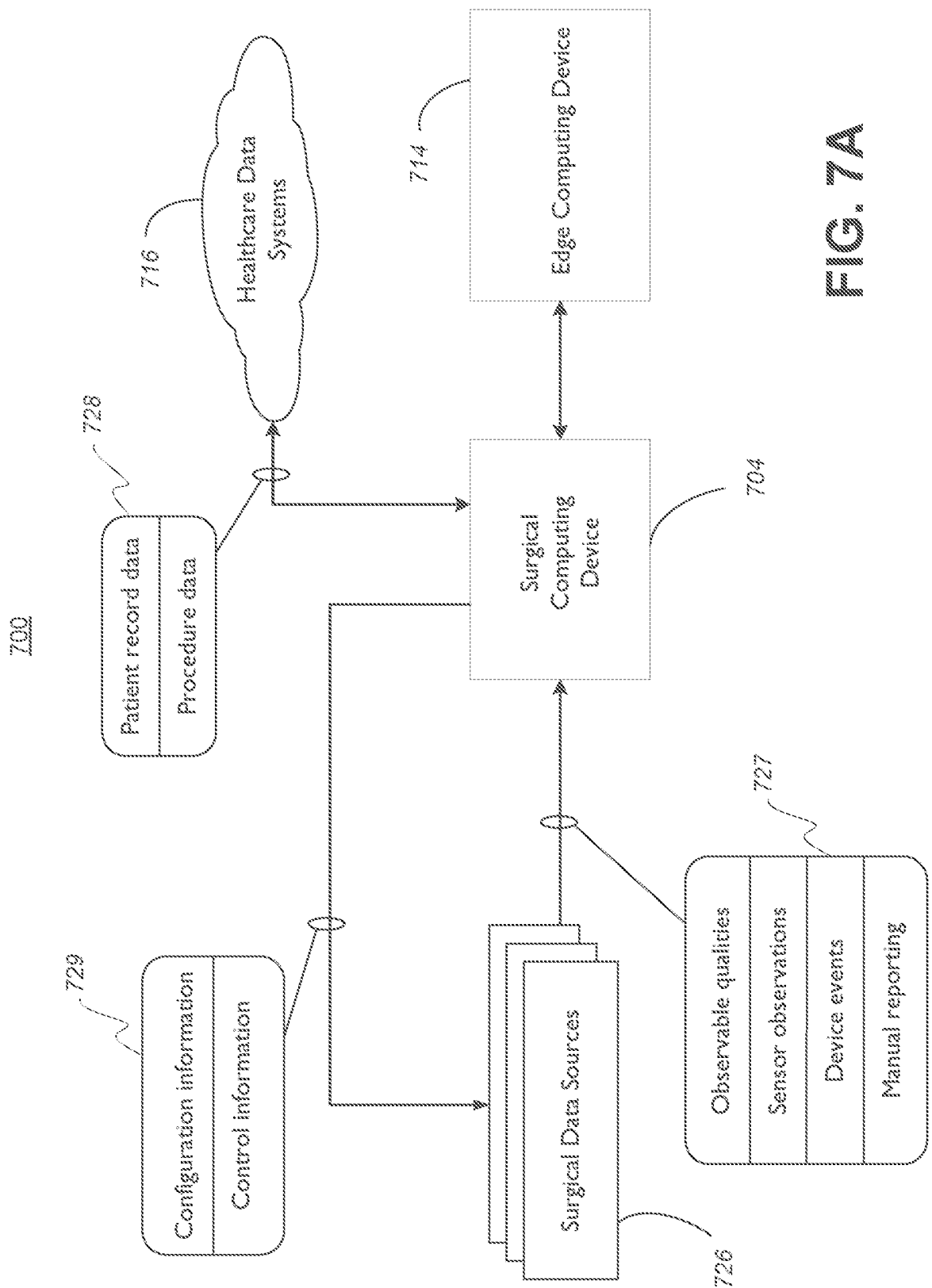
FIG. 7A-D show an example surgical system information matrix, an example information flow in a surgical system, an example information flow in a surgical system with a surgical robot, and an illustration of surgical information in the context of a procedure, respectively.

FIG. 7A illustrates a surgical system 700 that may include a matrix of surgical information. This surgical information may include any discrete atom of information relevant to surgical operation. Generally described, such surgical information may include information related to the context and scope of the surgery itself (e.g., healthcare information 728). Such information may include data such as procedure data and patient record data, for example. Procedure data and/or patient record data may be associated with a related healthcare data system 716 in communication with the surgical hub 704.

The surgical information may include information related to the configuration and/or control of devices being used in the surgery (e.g., device operational information 729). Such device operational information 729 may include information about the initial settings of surgical devices. Device operational information 729 may include information about changes to the settings of surgical devices. Device operational information 729 may include information about controls sent to the devices from the surgical hub 704 and information flows related to such controls.

The surgical information may include information generated during the surgery itself (e.g., surgery information 727). Such surgery information 727 may be include any information generated by a surgical data source 726. The data sources 726 may include any device in a surgical context that may generate useful surgery information 727. This surgery information 727 may present itself as observable qualities of the data source 726. The observable qualities may include static qualities, such as a device's model number, serial number, and the like. The observable qualities may include dynamic qualities such as the state of configurable settings of the device. The surgery information 727 may present itself as the result of sensor observations for example. Sensor observations may include those from specific sensors within the surgical theatre, sensors for monitoring conditions, such as patient condition, sensors embedded in surgical devices, and the like. The sensor observations may include information used during the surgery, such as video, audio, and the like. The surgery information 727 may present itself as a device event data. Surgical devices may generate notifications and/or may log events, and such events may be included in surgery information 727 for communication to the surgical hub 704. The surgery information 727 may present itself as the result of manual recording, for example. A healthcare professional may make a record during the surgery, such as asking that a note be taken, capturing a still image from a display, and the like The surgical data sources 726 may include modular devices (e.g., which can include sensors configured to detect parameters associated with the patient, HCPs and environment and/or the modular device itself), local databases (e.g., a local EMR database containing patient records), patient monitoring devices (e.g., a blood pressure (BP) monitor and an electrocardiography (EKG) monitor), HCP monitoring devices, environment monitoring devices, surgical instruments, surgical support equipment, and the like.

The surgical hub 704 can be configured to derive the contextual information pertaining to the surgical procedure from the data based upon, for example, the particular combination(s) of received data or the particular order in which the data is received from the data sources 726. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 704 to derive or infer information related to the surgical procedure from received data can be referred to as "situational awareness." For example, the surgical hub 704 can incorporate a situational awareness system, which is the hardware and/or programming associated with the surgical hub 704 that derives contextual information pertaining to the surgical procedure from the received data and/or a surgical plan information received from the edge computing system 714 or a healthcare data system 716 (e.g., enterprise cloud server).

In operation, this matrix of surgical information may be present as one or more information flows. For example, surgical information may flow from the surgical data sources 726 to the surgical hub 704. Surgical information may flow from the surgical hub 704 to the surgical data sources 726 (e.g., surgical devices). Surgical information may flow between the surgical hub 704 and one or more healthcare data systems 716. Surgical information may flow between the surgical hub 704 and one or more edge computing devices 714.

Surgical information, as presented in its one or more information flows, may be used in connection with one or more artificial intelligence (AI) systems to further enhance the operation of the surgical system 700. For example, a machine learning system, such as that described herein, may operate on one or more information flows to further enhance the operation of the surgical system 700.

Figure 7B:
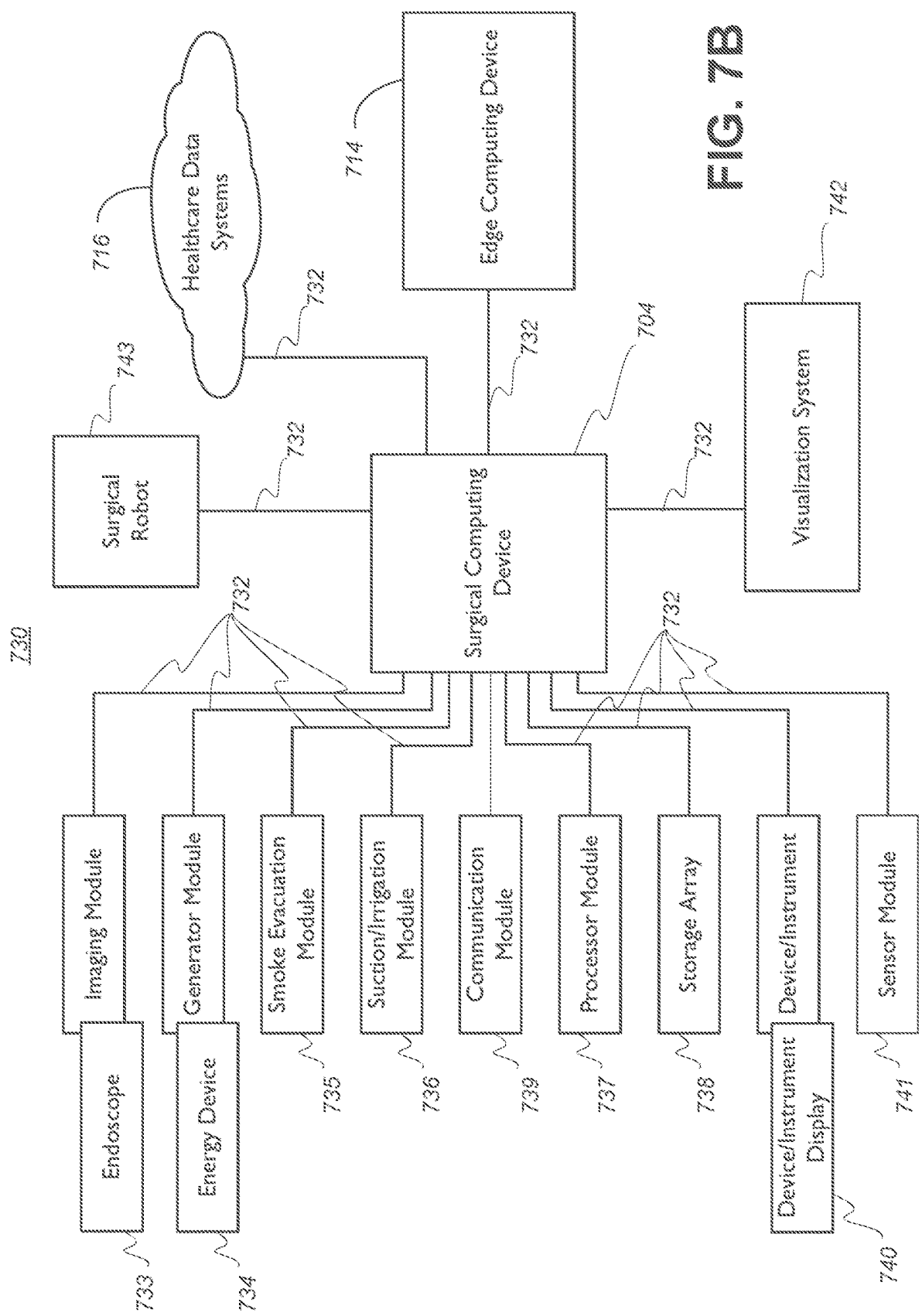

FIG. 7B shows an example computer-implement surgical system 730 with a plurality of information flows 732. A surgical computing device 704 may communication with and/or incorporate one or more surgical data sources. For example, an imaging module 733 (and endoscope) may exchange surgical information with the surgical computing device 704. Such information may include information from the imaging module 733 (and endoscope), such as video information, current settings, system status information, and the like. The imaging module 733 may receive information from the surgical computing device 704, such as control information, configuration information, operational updates (such as software/firmware), and the like.

For example, a generator module 734 (and corresponding energy device) may exchange surgical information with the surgical computing device 704. Such information may include information from the generator module 734 (and corresponding energy device), such as electrical information (e.g., current, voltage, impedance, frequency, wattage), activity state information, sensor information such as temperature, current settings, system events, active time duration, and activation timestamp, and the like. The generator module 734 may receive information from the surgical computing device 704, such as control information, configuration information, changes to the nature of the visible and audible notifications to the healthcare professional (e.g., changing the pitch, duration, and melody of audible tones), electrical application profiles and/or application logic that may instruct the generator module to provide energy with a defined characteristic curve over the application time, operational updates (such as software/firmware), and the like.

For example, a smoke evacuator 735 may exchange surgical information with the surgical computing device 704. Such information may include information from the smoke evacuator 735, such as operational information (e.g., revolutions per minute), activity state information, sensor information such as air temperature, current settings, system events, active time duration, and activation timestamp, and the like. The smoke evacuator 735 may receive information from the surgical computing device 704, such as control information, configuration information, operational updates (such as software/firmware), and the like.

For example, a suction/irrigation module 736 may exchange surgical information with the surgical computing device 704. Such information may include information from the suction/irrigation module 736, such as operational information (e.g., liters per minute), activity state information, internal sensor information, current settings, system events, active time duration, and activation timestamp, and the like. The suction/irrigation module 736 may receive information from the surgical computing device 704, such as control information, configuration information, operational updates (such as software/firmware), and the like.

For example, a communication module 739, a processor module 737, and/or a storage array 738 may exchange surgical information with the surgical computing device 704. In an example, the communication module 739, the processor module 737, and/or the storage array 738 may constitute all or part of the computing platform upon which the surgical computing device 704 runs. In an example, the communication module 739, the processor module 737, and/or the storage array 738 may provide local computing resources to other devices in the surgical system 730. Information from the communication module 739, the processor module 737, and/or the storage array 738 to the surgical computing device 704 may include logical computing-related reports, such as processing load, processing capacity, process identification, CPU %, CPU time, threads, GPU %, GPU time, memory utilization, memory thread, memory ports, energy usage, bandwidth related information, packets in, packets out, data rate, channel utilization, buffer status, packet loss information, system events, other state information, and the like. The communication module 739, the processor module 737, and/or the storage array 738 may receive information from the surgical computing device 704, such as control information, configuration information, operational updates (such as software/firmware), and the like. The communication module 739, the processor module 737, and/or the storage array 738 may also receive information from the surgical computing device 704 generated by another element or device of the surgical system 730. For example, data source information may be sent to and stored in the storage array. For example, data source information may be processed by the processor module 737.

For example, an intelligent instrument 740 (with or without a corresponding display) may exchange surgical information with the surgical computing device 704. Such information may include information from the intelligent instrument 740 relative to the instrument's operation, such as device electrical and/or mechanical information (e.g., current, voltage, impedance, frequency, wattage, torque, force, pressure, etc.), load state information (e.g., information regarding the identity, type, and/or status of reusables, such as staple cartridges), internal sensor information such as clamping force, tissue compression pressure and/or time, system events, active time duration, and activation timestamp, and the like. The intelligent instrument 740 may receive information from the surgical computing device 704, such as control information, configuration information, changes to the nature of the visible and audible notifications to the healthcare professional (e.g., changing the pitch, duration, and melody of audible tones), mechanical application profiles and/or application logic that may instruct a mechanical component of the instrument to operate with a defined characteristic (e.g., blade/anvil advance speed, mechanical advantage, firing time, etc.), operational updates (such as software/firmware), and the like.

For example, a sensor module 741 may exchange surgical information with the surgical computing device 704. Such information may include information from the sensor module 741 relative to its sensor function, such as sensor results themselves, observational frequency and/or resolution, observational type, device alerts such as alerts for sensor failure, observations exceeding a defined range, observations exceeding an observable range, and the like. The sensor module 741 may receive information from the surgical computing device 704, such as control information, configuration information, changes to the nature of observation (e.g., frequency, resolution, observational type etc.), triggers that define specific events for observation, on control, off control, data buffering, data preprocessing algorithms, operational updates (such as software/firmware), and the like.

For example, a visualization system 742 may exchange surgical information with the surgical computing device 704. Such information may include information from the visualization system 742, such visualization data itself (e.g., still image, video, advanced spectrum visualization, etc.), visualization metadata (e.g., visualization type, resolution, frame rate, encoding, bandwidth, etc.). The visualization system 742 may receive information from the surgical computing device 704, such as control information, configuration information, changes to the video settings (e.g., visualization type, resolution, frame rate, encoding, etc.), visual display overlay data, data buffering size, data preprocessing algorithms, operational updates (such as software/firmware), and the like.

For example, a surgical robot 743 may exchange surgical information with the surgical computing device 704. Information from the surgical robot 743 may include any aforementioned information as applied to robotic instruments, sensors, and devices. Information from the surgical robot 743 may also include information related to the robotic operation or control of such instruments, such as electrical/mechanical feedback of robot articulators, system events, system settings, mechanical resolution, control operation log, articulator path information, and the like. The surgical robot 743 may receive information from the surgical computing device 704, such as control information, configuration information, operational updates (such as software/firmware), and the like.

Figure 7C:
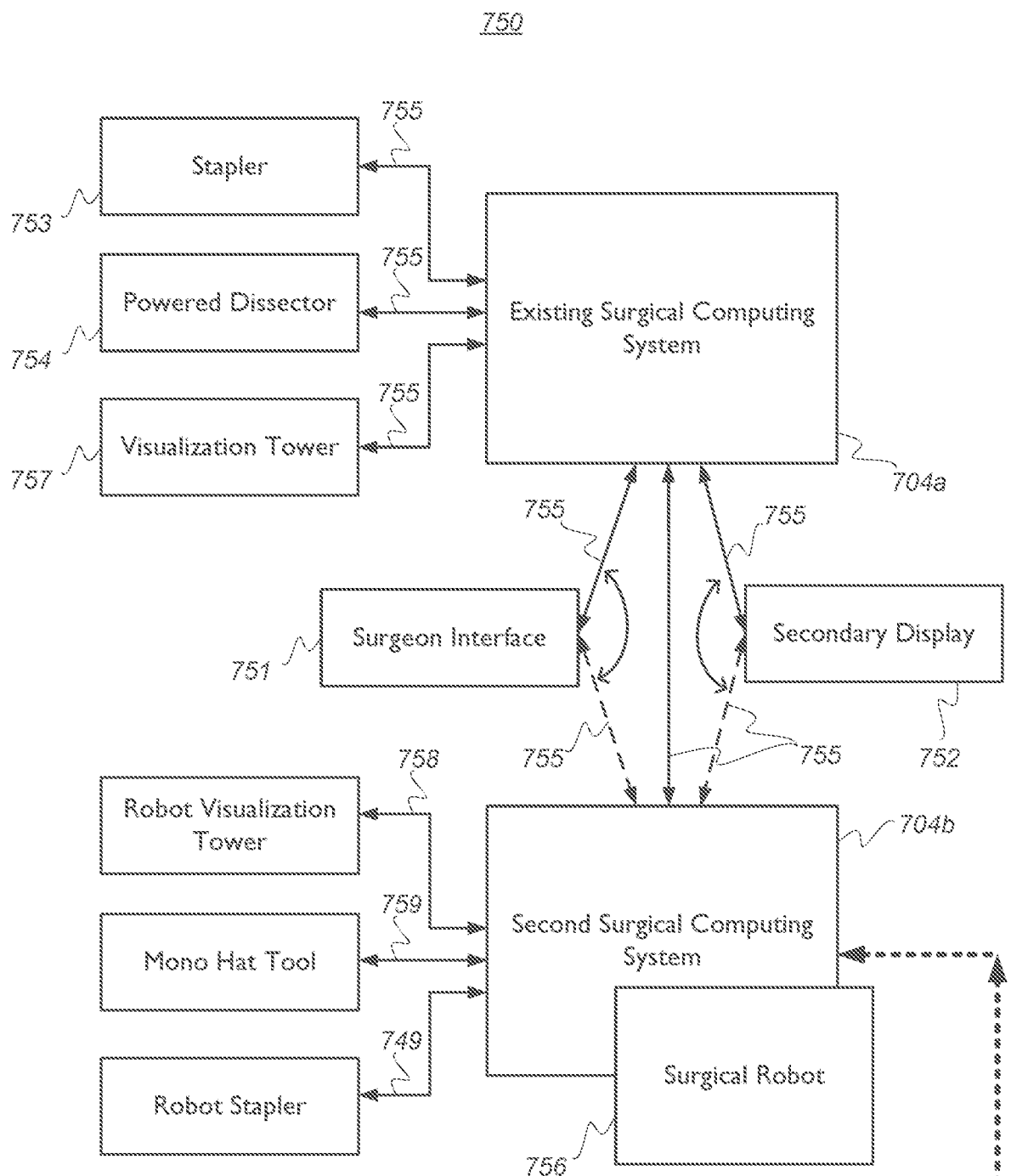

FIG. 7C illustrates an example information flow associated with a plurality of surgical computing systems 704a, 704b in a common environment. When the overall configuration of a computer-implement surgical system (e.g., computer-implement surgical system 750) changes (e.g., when data sources are added and/or removed from the surgical computing system, for example), further surgical information may be generated to reflect the changes. In this example, a second surgical computing system 704b (e.g., surgical hub) may be added (with a corresponding surgical robot) to surgical system 750 with an existing surgical computing system 704a. The messaging flow described here represents further surgical information flows 755 to be employed as disclosed herein (e.g., further consolidated, analyzed, and/or processed according to an algorithm, such as a machine learning algorithm).

Here, the two surgical computing systems 704a, 704b request permission from a surgical operator for the second surgical computing system 704b (with the corresponding surgical robot 756) to take control of the operating room from the existing surgical computing system 704a. The second surgical computing system 704b presents in the operating theater with control of the corresponding surgical robot 756, a robot visualization tower 758, a mono hat tool 759, and a robot stapler 749. The permission can be requested through a surgeon interface or console 751. Once permission is granted, the second surgical computing system 704b messages the existing surgical computing system 704a a request a transfer of control of the operating room.

In an example, the surgical computing systems 704a, 704b can negotiate the nature of their interaction without external input based on previously gathered data. For example, the surgical computing systems 704a, 704b may collectively determine that the next surgical task requires use of a robotic system. Such determination may cause the existing surgical computing system 704a to autonomously surrender control of the operating room to the second surgical computing system 704b. Upon completion of the surgical task, the second surgical computing system 704b may then autonomously return the control of the operating room to the existing surgical computing system 704a.

As illustrated in FIG. 7C, the existing surgical computing system 704a has transferred control to the second surgical computing system 704b, which has also taken control of the surgeon interface 751 and the secondary display 752. The second surgical computing system 704b assigns new identification numbers to the newly transferred devices. The existing surgical computing system 704a retains control the handheld stapler 753, the handheld powered dissector 754, and visualization tower 757. In addition, the existing surgical computing system 704a may perform a supporting role, wherein the processing and storage capabilities of the existing surgical computing system 704a are now available to the second surgical computing system 704b.

Figure 7D:
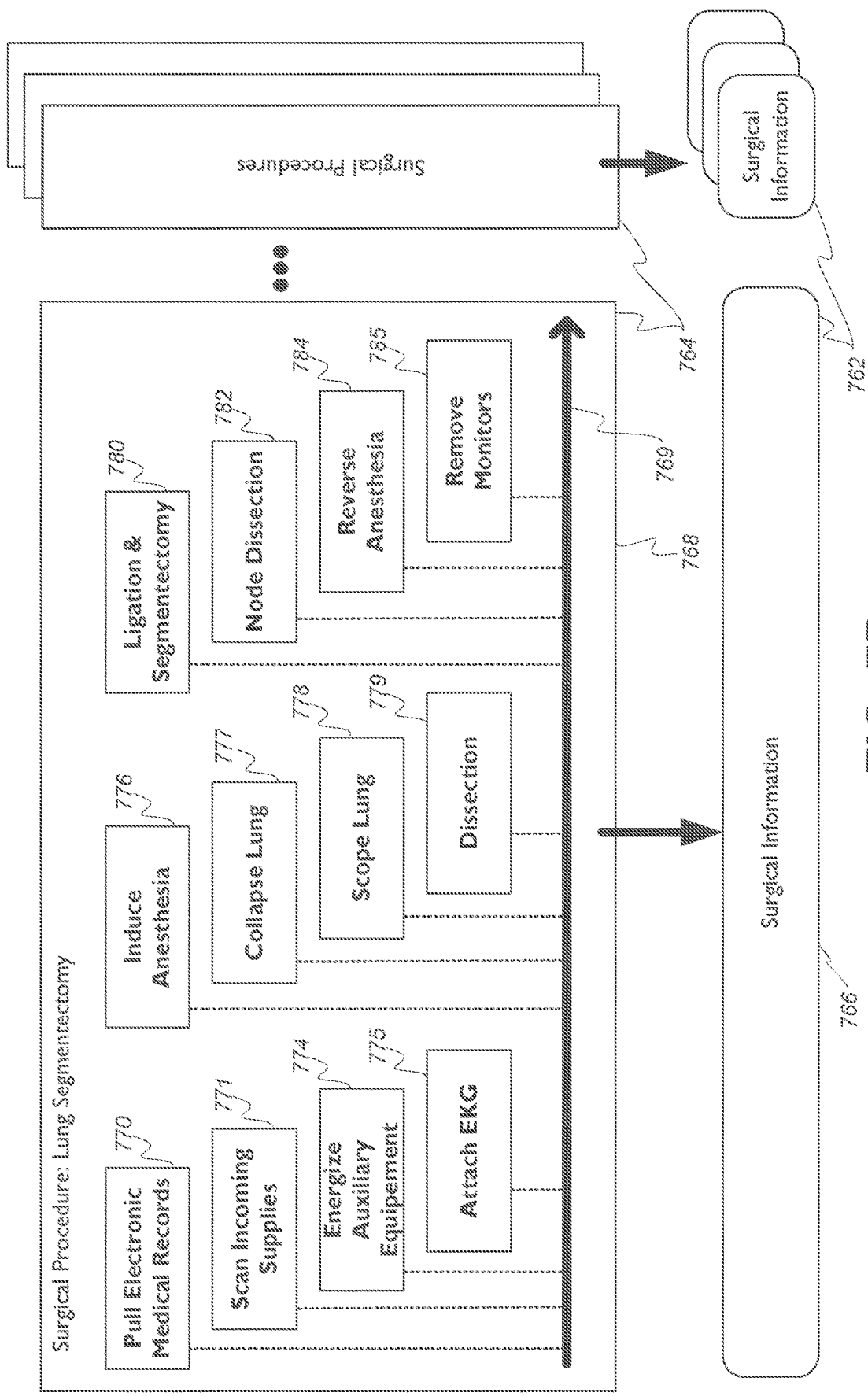

FIG. 7D illustrates an example surgical information flow in the context of a surgical procedure and a corresponding example use of the surgical information for predictive modeling. The surgical information disclosed herein may provide data regarding one or more surgical procedures, including the surgical tasks, instruments, instrument settings, operational information, procedural variations, and corresponding desirable metrics, such as improved patient outcomes, lower cost (e.g., fewer resources utilized, less surgical time, etc.). The surgical information disclosed herein (e.g., that disclosed in regard to FIGS. 7A-C) in the context of one or more surgical systems and devices disclosed herein, provides a platform upon which the specific machine learning algorithms and techniques disclosed herein may be used.

Surgical information 762 from a plurality of surgical procedures 764 (e.g., a subset of surgical information from each procedure) may be collected. The surgical information 762 may be collected from the plurality of surgical procedures 764 by collecting data represented by the one or more information flows disclosed herein, for example.

To illustrate, example instance of surgical information 766 may be generated from the example procedure 768 (e.g, a lung segmentectomy procedure as shown on a timeline 769). Surgical information 766 may be generated during the preoperative planning and may include patient record information. Surgical information 766 may be generated from the data sources (e.g., data sources 726) during the course of the surgical procedure, including data generated each time medical personnel utilize a modular device that is paired with the surgical computing system (e.g., surgical computing system 704). The surgical computing system may receive this data from the paired modular devices and other data sources The surgical computing system itself may generate surgical information as part of its operation during the procedure. For example, the surgical computing system may record information relating to configuration and control operations. The surgical computing system may record information related to situational awareness activities. For example, the surgical computing system may record the recommendations, prompts, and/or other information provided to the healthcare team (e.g., provided via a display screen) that may be pertinent for the next procedural step. For example, the surgical computing system may record configuration and control changes (e.g., the adjusting of modular devices based on the context). Such configuration and control changes may include activating monitors, adjusting the field of view (FOV) of a medical imaging device, changing the energy level of an ultrasonic surgical instrument or RF electrosurgical instrument, or the like.

At 770, the hospital staff members retrieve the patient's EMR from the hospital's EMR database. Based on select patient data in the EMR, the surgical computing system determines that the procedure to be performed is a thoracic procedure.

At 771, the staff members scan the incoming medical supplies for the procedure. The surgical computing system may cross-reference the scanned supplies with a list of supplies that are utilized in various types of procedures. The surgical computing system may confirm that the mix of supplies corresponds to a thoracic procedure. Further, the surgical computing system may determine that the procedure is not a wedge procedure (because the incoming supplies either lack certain supplies that are necessary for a thoracic wedge procedure or do not otherwise correspond to a thoracic wedge procedure). The medical personnel may also scan the patient band via a scanner that is communicably connected to the surgical computing system. The surgical computing system may confirm the patient's identity based on the scanned data.

At 774, the medical staff turns on the auxiliary equipment. The auxiliary equipment being utilized can vary according to the type of surgical procedure and the techniques to be used by the surgeon. In this example, the auxiliary equipment may include a smoke evacuator, an insufflator, and medical imaging device. When activated, the auxiliary equipment may pair with the surgical computing system. The surgical computing system may derive contextual information about the surgical procedure based on the types of paired. In this example, the surgical computing system determines that the surgical procedure is a VATS procedure based on this particular combination of paired devices. The contextual information about the surgical procedure may be confirmed by the surgical computing system via information from the patient's EMR.

The surgical computing system may retrieve the steps of the procedure to be performed. For example, the steps may be associated with a procedural plan (e.g., a procedural plan specific to this patient's surgery, a procedural plan associated with a particular surgeon, a procedural plan template for the procedure generally, or the like).

At 775, the staff members attach the EKG electrodes and other patient monitoring devices to the patient. The EKG electrodes and other patient monitoring devices pair with the surgical computing system. The surgical computing system may receive data from the patient monitoring devices.

At 776, the medical personnel induce anesthesia in the patient. The surgical computing system may record information related to this procedural step such as data from the modular devices and/or patient monitoring devices, including EKG data, blood pressure data, ventilator data, or combinations thereof, for example.

At 777, the patient's lung subject to operation is collapsed (ventilation may be switched to the contralateral lung). The surgical computing system may determine that this procedural step has commenced and may collect surgical information accordingly, including for example, ventilator data, one or more timestamps, and the like At 778, the medical imaging device (e.g., a scope) is inserted and video from the medical imaging device is initiated. The surgical computing system may receive the medical imaging device data (i.e., video or image data) through its connection to the medical imaging device. The data from the medical imaging device may include imaging data and/or imaging metadata, such as the angle at which the medical imaging device is oriented with respect to the visualization of the patient's anatomy, the number or medical imaging devices presently active, and the like. The surgical computing system may record positioning information of the medical imaging device. For example, one technique for performing a VATS lobectomy places the camera in the lower anterior corner of the patient's chest cavity above the diaphragm. Another technique for performing a VATS segmentectomy places the camera in an anterior intercostal position relative to the segmental fissure.

Using pattern recognition or machine learning techniques, for example, the surgical computing system may be trained to recognize the positioning of the medical imaging device according to the visualization of the patient's anatomy. For example, one technique for performing a VATS lobectomy utilizes a single medical imaging device. Another technique for performing a VATS segmentectomy uses multiple cameras. Yet another technique for performing a VATS segmentectomy uses an infrared light source (which may be communicably coupled to the surgical computing system as part of the visualization system).

At 779, the surgical team begins the dissection step of the procedure. The surgical computing system may collect data from the RF or ultrasonic generator indicating that an energy instrument is being fired. The surgical computing system may cross-reference the received data with the retrieved steps of the surgical procedure to determine that an energy instrument being fired at this point in the process (i.e., after the completion of the previously discussed steps of the procedure) corresponds to the dissection step. In an example, the energy instrument may be an energy tool mounted to a robotic arm of a robotic surgical system.

At 780, the surgical team proceeds to the ligation step of the procedure. The surgical computing system may collect surgical information 766 with regard to the surgeon ligating arteries and veins based on receiving data from the surgical stapling and cutting instrument indicating that such instrument is being fired. Next, the segmentectomy portion of the procedure is performed. The surgical computing system may collect information relating to the surgeon transecting the parenchyma. For example, the surgical computing system may receive surgical information 766 from the surgical stapling and cutting instrument, including data regarding its cartridge, settings, firing details, and the like.

At 782, the node dissection step is then performed. The surgical computing system may collect surgical information 766 with regard to the surgical team dissecting the node and performing a leak test. For example, the surgical computing system may collect data received from the generator indicating that an RF or ultrasonic instrument is being fired and including the electrical and status information associated with the firing. Surgeons regularly switch back and forth between surgical stapling/cutting instruments and surgical energy (i.e., RF or ultrasonic) instruments depending upon the particular step in the procedure. The surgical computing system may collect surgical information 766 in view of the particular sequence in which the stapling/cutting instruments and surgical energy instruments are used. In an example, robotic tools may be used for one or more steps in a surgical procedure. The surgeon may alternate between robotic tools and handheld surgical instruments and/or can use the devices concurrently, for example.

Next, the incisions are closed up and the post-operative portion of the procedure begins. At 784, the patient's anesthesia is reversed. The surgical computing system may collect surgical information regarding the patient emerging from the anesthesia based on ventilator data (e.g., the patient's breathing rate begins increasing), for example.

At 785, the medical personnel remove the various patient monitoring devices from the patient. The surgical computing system may collect information regarding the conclusion of the procedure. For example, the surgical computing system may collect information related to the loss of EKG, BP, and other data from the patient monitoring devices.

The surgical information 762 (including the surgical information 766) may be structured and/or labeled. The surgical computing system may provide such structure and/or labeling inherently in the data collection. For example, in surgical information 762 may be labeled according to a particular characteristic, a desired result (e.g., efficiency, patient outcome, cost, and/or a combination of the same, or the like), a certain surgical technique, an aspect of instrument use (e.g., selection, timing, and activation of a surgical instrument, the instrument's settings, the nature of the instrument's use, etc.), the identity of the health care professionals involved, a specific patient characteristic, or the like, each of which may be present in the data collection.

Surgical information (e.g., surgical information 762 collected across procedures 764) may be used in connection with one or more artificial intelligence (AI) systems. AI may be used to perform computer cognitive tasks. For example, AI may be used to perform complex tasks based on observations of data. AI may be used to enable computing systems to perform cognitive tasks and solve complex tasks. AI may include using machine learning and machine learning techniques. ML techniques may include performing complex tasks, for example, without being programmed (e.g., explicitly programmed). For example, a ML technique may improve over time based on completing tasks with different inputs. A ML process may train itself, for example using input data and/or a learning dataset.

Machine learning (ML) techniques may be employed, for example, in the medical field. For example, ML may be used on a set of data (e.g., a set of surgical data) to produce an output (e.g., reduced surgical data, processed surgical data). In examples, the output of a ML process may include identified trends or relationships of the data that were input for processing. The outputs may include verifying results and/or conclusions associated with the input data. In examples, an input to a ML process may include medical data, such as surgical images and patient scans. The ML process may output a determined medical condition based on the input surgical images and patient scans. The ML process may be used to diagnose medical conditions, for example, based on the surgical scans.

ML processes may improve themselves, for example, using the historic data that trained the ML processes and/or the input data. Therefore, ML processes may be constantly improving with added inputs and processing. The ML processes may update based on input data. For example, over time, a ML process that produces medical conclusions based on medical data may improve and become more accurate and consistent in medical diagnoses.

ML processes may be used to solve different complex tasks (e.g., medical tasks). For example, ML processes may be used for data reduction, data preparation, data processing, trend identification, conclusion determination, medical diagnoses, and/or the like. For example, ML processes may take in surgical data as an input and process the data to be used for medical analysis. The processed data may be used to determine a medical diagnosis. In the end, the ML processes may take raw surgical data and generate useful medical information (e.g., medical trends and/or diagnoses) associated with the raw surgical data.

ML processes may be combined to perform different discrete tasks on an input data set. For example, a ML process may include testing different combinations of ML sub-processes performing discrete tasks to determine which combination of ML sub-processes performs the best (e.g., competitive usage of different process/algorithm types and training to determine the best combination for a dataset). For example, the ML process may include sub-process (e.g., algorithm) control and monitoring to improve and/or verify results and/or conclusions (e.g., error bounding).

A ML process may be initialized and/or setup to perform tasks. For example, the ML process may be initialized based on initialization configuration information. The initialized ML process may be untrained and/or a base ML process for performing the task. The untrained ML process may be inaccurate in performing the designated tasks. As the ML process becomes trained, the tasks may be performed more accurately.

The initialization configuration information for a ML process may include initial settings and/or parameters. For example, the initial settings and/or parameters may include defined ranges for the ML process to employ. The ranges may include ranges for manual inputs and/or received data. The ranges may include default ranges and/or randomized ranges for variables not received, for example, which may be used to complete a dataset for processing. For example, if a dataset is missing a data range, the default data range may be used as a substitute to perform the ML process.

The initialization configuration information for a ML process may include data storage locations. For example, locations or data storages and/or databases associated with data interactions may be included. The databases associated with data interactions may be used to identify trends in datasets. The databases associated with data interactions may include mappings of data to a medical condition. For example, a database associated with data interactions may include a mapping for heart rate data to medical conditions, such as, for example, arrythmia and/or the like.

The initialization configuration information may include parameters associated with defining the system. The initialization configuration information may include instructions (e.g., methods) associated with displaying, confirming, and/or providing information to a user. For example, the initialization configuration may include instructions to the ML process to output the data in a specific format for visualization for a user.

ML techniques may be used, for example, to perform data reduction. ML techniques for data reductions may include using multiple different data reduction techniques. For example, ML techniques for data reductions may include using one or more of the following: CUR matrix decomposition; a decision tree; expectation-maximization (EM) processes (e.g., algorithms); explicit semantic analysis (ESA); exponential smoothing forecast; generalized linear model; k-means clustering (e.g., nearest neighbor); Naive Bayes; neural network processes; a multivariate analysis; an o-cluster; a singular value decomposition; Q-learning; a temporal difference (TD); deep adversarial networks; support vector machines (SVM); linear regression; reducing dimensionality; linear discriminant analysis (LDA); adaptive boosting (e.g., AdaBoost); gradient descent (e.g., Stochastic gradient descent (SGD)); outlier detection; and/or the like.

ML techniques may be used to perform data reduction, for example, using CUR matrix decompositions. A CUR matrix decomposition may include using a matrix decomposition model (e.g., process, algorithm), such as a low-rank matrix decomposition model. For example, CUR matrix decomposition may include a low-rank matrix decomposition process that is expressed (e.g., explicitly expressed) in a number (e.g., small number) of columns and/or rows of a data matrix (e.g., the CUR matrix decomposition may be interpretable). CUR matrix decomposition may include selecting columns and/or rows associated with statistical leverage and/or a large influence in the data matrix. Using CUR matrix decomposition may enable identification of attributes and/or rows in the data matrix. The simplification of a larger dataset (e.g., using CUR matrix decomposition) may enable review and interaction (e.g., with the data) by a user. CUR matrix decomposition may facilitate regression, classification, clustering, and/or the like.

ML techniques may be used to perform data reduction, for example, using decision trees (e.g., decision tree model). Decision trees may be used, for example, as a framework to quantify values of outcomes and/or the probabilities of outcomes occurring. Decision trees may be used, for example, to calculate the value of uncertain outcome nodes (e.g., in a decision tree). Decision trees may be used, for example, to calculate the value of decision nodes (e.g., in a decision tree). A decision tree may be a model to enable classification and/or regression (e.g., adaptable to classification and/or regression problems). Decision trees may be used to analyze numerical (e.g., continuous values) and/or categorical data. Decision trees may be more successful with large data sets and/or may be more efficient (e.g., as compared to other data reduction techniques).

Decision trees may be used in combination with other decision trees. For example, a random forest may refer to a collection of decision trees (e.g., ensemble of decision trees). A random forest may include a collection of decision trees whose results may be aggregated into a result. A random forest may be a supervised learning algorithm. A random forest may be trained, for example, using a bagging training process.

A random decision forest (e.g., random forest) may add randomness (e.g., additional randomness) to a model, for example, while growing the trees. A random forest may be used to search for a best feature among a random subset of features, for example, rather than searching for the most important feature (e.g., while splitting a node). Searching for the best feature among a random subset of features may result in a wide diversity that may result in a better (e.g., more efficient and/or accurate) model.

A random forest may include using parallel ensembling. Parallel ensembling may include fitting (e.g., several) decision tree classifiers in parallel, for example, on different data set sub-samples. Parallel ensembling may include using majority voting or averages for outcomes or final results. Parallel ensembling may be used to minimize overfitting and/or increase prediction accuracy and control. A random forest with multiple decision trees may (e.g., generally) be more accurate than a single decision tree-based model. A series of decision trees with controlled variation may be built, for example, by combining bootstrap aggregation (e.g., bagging) and random feature selection.

ML techniques may be used to perform data reduction, for example, using an expectation maximization (EM) model (e.g., process, algorithm). For example, an EM model may be used to find a likelihood (e.g., local maximum likelihood) parameter of a statistical model. An EM model may be used for cases where equations may not be solved directly. An EM model may consider latent variables and/or unknown parameters and known data observations. For example, the EM model may determine that missing values exist in a data set. The EM model receive configuration information indicating to assume the existence of missing (e.g., unobserved) data points in a data set.

An EM model may use component clustering. For example, component clustering may enable the grouping of EM components into high-level clusters. Components may be treated as clustered, for example, if component clustering is disabled (e.g., in an EM model).

ML techniques may be used to perform data reduction, for example, using explicit semantic analysis (ESA). ESA may be used at a level of semantics (e.g., meaning) rather than on vocabulary (e.g., surface form vocabulary) of words or a document. ESA may focus on the meaning of a set of text, for example, as a combination of the concepts found in the text. ESA may be used in document classification. ESA may be used for a semantic relatedness calculation (e.g., how similar in meaning words or pieces of text are to each other). ESA may be used for information retrieval.

ESA may be used in document classification, for example. Document classification may include tagging documents for managing and sorting. Tagging a document (e.g., with a keyword) may allow for easier searching. Keyword tagging (e.g., only using keyword tagging) may limit the accuracy and/or efficiency of document classification. For example, using keyword tagging may uncover (e.g., only uncover) documents with the keywords and not documents with words with similar meaning to the keywords. Classifying text semantically (e.g., using ESA) may improve a model's understanding of text. Classifying text semantically may include representing documents as concepts and lowering dependence on specific keywords.

ML techniques may be used to perform data reduction, for example, using an exponential smoothing forecast model. Exponential smoothing may be used to smooth time series data, for example, using an exponential window function. For example, in a moving average, past observations may be weighted equally, but exponential functions may be used to assign exponentially decreasing weights over time.

ML techniques may be used to perform data reduction, for example, using linear regression. Linear regression may be used to predict continuous outcomes. For example, linear regression may be used to predict the value of a variable (e.g., dependent variable) based on the value of a different variable (e.g., independent variable). Linear regression may apply a linear approach for modeling a relationship between a scalar response and one or more explanatory variables (e.g., dependent and/or independent variables). Simple linear regression may refer to linear regression use cases associated with one explanatory variable. Multiple linear regression may refer to linear regression use cases associated with more than one explanatory variables. Linear regression may model relationships, for example, using linear predictor functions. The linear predictor functions may estimate unknown model parameters from a data set.

For example, linear regression may be used to identify patterns within a training dataset. The identified patterns may relate to values and/or label groupings. The model may learn a relationship between the (e.g., each) label and the expected outcomes. After training, the model may be used on raw data outside the training data set (e.g., data without a mapped and/or known output). The trained model using linear regression may determine calculated predictions associated with the raw data, for example, such as identifying seasonal changes in sales data.

ML techniques may be used to perform data reduction, for example, a generalized linear model (GLM). A GLM may be used as a flexible generalization of linear regression. GLM may generalize linear regression, for example, by enabling a linear model to be related to a response variable.

ML techniques may be used to perform data reduction, for example, using k-means clustering (e.g., a nearest neighbor model). K-means clustering may be used for vector quantization. K-means clustering may be used in signal processing. K-means clustering may be aimed at partitioning n observations into k clusters, for example, where each observation is classified into a cluster with the closest mean.

K-means clustering may include K-Nearest Neighbors (KNN) learning. KNN may be an instance-based learning (e.g., non-generalized learning, lazy learning). KNN may refrain from constructing a general internal model. KNN may include storing instances corresponding to training data in an n-dimensional space. KNN may use data and classify data points, for example, based on similarity measures (e.g., Euclidean distance function). Classification may be computed, for example, based on a majority vote of the k nearest neighbors of a (e.g., each) point. KNN may be robust for noisy training data. Accuracy may depend on data quality (e.g., for KNN). KNN may include choosing a number of neighbors to be considered (e.g., optimal number of neighbors to be considered). KNN may be used for classification and/or regression.

ML techniques may be used to perform data reduction, for example, using a Naive Bayes model (e.g., process). A Naive Bayes model may be used, for example, to construct classifiers. A Naive Bayes model may be used to assign class labels to problem instances (e.g., represented as vectors of feature values). The class labels may be drawn from a set (e.g., finite set). Different processes (e.g., algorithms) may be used to train the classifiers. A family of processes (e.g., family of algorithms) may be used. The family of processes may be based on a principle where the Naive Bayes classifiers (e.g., all the Naive Bayes) classifiers assume that the value of a feature is independent of the value of a different feature (e.g., given the class variable).

ML techniques may be used to perform data reduction, for example, using a neural network. Neural networks may learn (e.g., be trained) by processing examples, for example, to perform other tasks (e.g., similar tasks). A processing example may include an input and a result (e.g., input mapped to a result). The neural network may learn by forming probability-weighted associations between the input and the result. The probability-weighted associations may be stored within a data structure of the neural network. The training of the neural network from a given example may be conducted by determining the difference between a processed output of the network (e.g., prediction) and a target output. The difference may be the error. The neural network may adjust the weighted associations (e.g., stored weighted associations), for example, according to a learning rule and the error value.

ML techniques may be used to perform data reduction, for example, using multivariate analysis. Multivariate analysis may include performing multivariate state estimation and/or non-negative matrix factorization.

ML techniques may be used to perform data reduction, for example, using support vector machines (SVMs). SVMs may be used in a multi-dimensional space (e.g., high-dimensional space, infinite-dimensional space). SVCs may be used to construct a hyper-plane (e.g., set of hyper-planes). A hyper-plane that has the greatest distance (e.g., compared to the other constructed hyper-planes) from a nearest training data point in a class (e.g., any class) may achieve a strong separation (e.g., in general, the greater the margin, the lower the classifier's generalization error). SVMs may be effective in high-dimensional spaces. SVMs may behave differently, for example, based on different mathematical functions (e.g., the kernel, kernel functions). For example, kernel functions may include one or more of the following: linear, polynomial, radial basis function (RBF), sigmoid, etc. The kernel functions may be used as a SVM classifier. SVM may be limited in use cases, for example, where a data set contains high amounts of noise (e.g., overlapping target classes).

ML techniques may be used to perform data reduction, for example, such as reducing dimensionality. Reducing dimensionality of a sample of data (e.g., unlabeled data) may help refine groups and/or clusters. Reducing a number of variables in a model may simplify data trends. Simplified data trends may enable more efficient processing. Reducing dimensionality may be used, for example, if many (e.g., too many) dimensions are clouding (e.g., negatively affecting) insights, trends, patterns, conclusions, and/or the like.

Reducing dimensionality may include using principal component analysis (PCA). PCA may be used to establish principal components that govern a relationship between data points. PCA may focus on simplifying (e.g., only simplifying) the principal components. Reducing dimensionality (e.g., PCA) may be used to maintain the variety of data grouping in a data set, but streamline the number of separate groups.

ML techniques may be used to perform data reduction, for example, linear discriminant analysis (LDA). LDA may refer to a linear decision boundary classifier, for example, that may be created by fitting class conditional densities to data (e.g., and applying Bayes' rule). LDA may include a generalization of Fisher's linear discriminant (e.g., projecting a given dataset into lower-dimensional space, for example, to reduce dimensionality and minimize complexity of a model and reduce computational costs). An LDA model (e.g., standard LDA model) may suit a class with a Gaussian density. The LDA model may assume that the classes (e.g., all classes) share a covariance matrix. LDA may be similar to analysis of variance (ANOVA) processes and/or regression analysis. For example, LDA may be used to express a dependent variable as a linear combination of other features and/or measurements.

ML techniques may be used to perform data reduction, for example, such as adaptive boosting (e.g., AdaBoost). Adaptive boosting may include creating a classifier (e.g., powerful classifier). Adaptive boosting may include creating a classier by combining multiple classifiers (e.g., poorly performing classifiers), for example, to obtain a resulting classifier with high accuracy. AdaBoost may be an adaptive classifier that improves the efficiency of a classifier. AdaBoost may trigger overfits. AdaBoost may be used (e.g., best used) to boost the performance of decision trees, base estimator(s), binary classification problems, and/or the like. AdaBoost may be sensitive to noisy data and/or outliers.

ML techniques may be used to perform data reduction, for example, such as stochastic gradient descent (SGD). SGD may include an iterative process used to optimize a function (e.g., objective function). SGD may be used to optimize an objective function, for example, with certain smoothness properties. Stochastic may refer to random probability. SGD may be used to reduce computational burden, for example, in high-dimensional optimization problems. SGD may be used to enable faster iterations, for example, while exchanging for a lower convergence rate. A gradient may refer to the slop of a function, for example, that calculates a variable's degree of change in response to another variable's changes. Gradient descent may refer to a convex function that outputs a partial derivative of a set of its input parameters. For example, $\alpha$ may be a learning rate and Ji may be a training example cost of the ith iteration. The equation may represent the stochastic gradient descent weight update method at the jth iteration. In large-scale ML and sparse ML, SGD may be applied to problems in text classification and/or natural language processing (NLP). SGD may be sensitive to feature scaling (e.g., may need to use a range of hyperparameters, for example, such as a regularization parameter and a number of iterations).

ML techniques may be used to perform data reduction, for example, such as using outlier detection. An outlier may be a data point that contains information (e.g., useful information) on an abnormal behavior of a system described by the data. Outlier detection processes may include univariate processes and multivariate processes.

ML processes may be trained, for example, using one or more training methods. For example, ML processes may be trained using one or more of the following training techniques: supervised learning, unsupervised learning, semi-supervised learning; reinforcement learning, and/or the like.

Figure 8A:
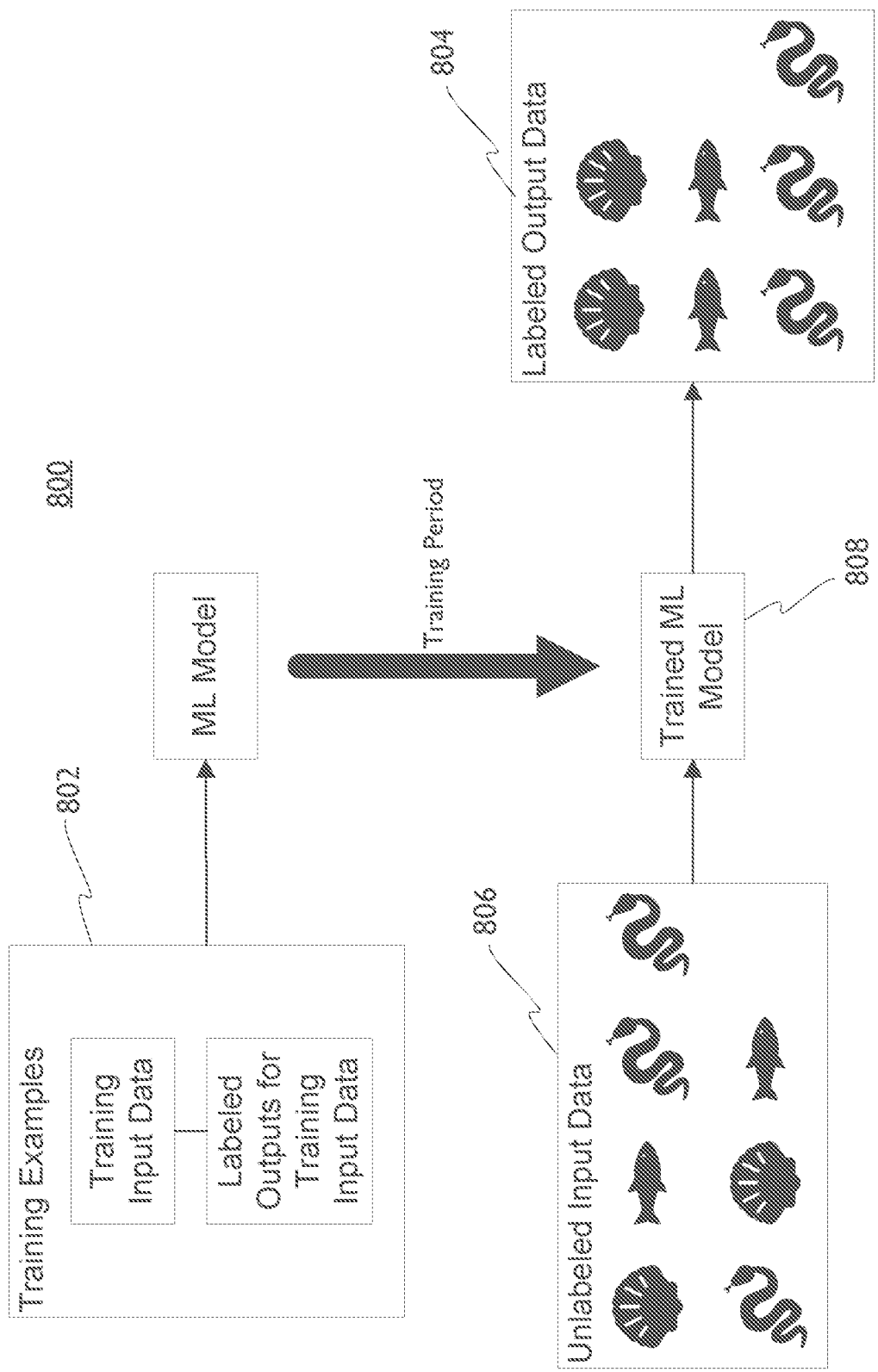
FIGS. 8A&B show an example supervised learning framework and an example unsupervised learning framework, respectively.

Machine learning may be supervised (e.g., supervised learning). A supervised learning algorithm may create a mathematical model from training a dataset (e.g., training data). FIG. 8A illustrates an example supervised learning framework 800. The training data (e.g., training examples 802, for example, as shown in FIG. 8) may consist of a set of training examples (e.g., input data mapped to labeled outputs, for example, as shown in FIG. 8). A training example 802 may include one or more inputs and one or more labeled outputs. The labeled output(s) may serve as supervisory feedback. In a mathematical model, a training example 802 may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function (e.g., a trained ML model 808) may determine the output 804 (e.g., labeled outputs) for one or more inputs 806 that may not have been a part of the training data (e.g., input data without mapped labeled outputs, for example, as shown in FIG. 8). Example algorithms may include linear regression, logistic regression, neutral network, nearest neighbor, Naive Bayes, decision trees, SVM, and/or the like. Example problems solvable by supervised learning algorithms may include classification, regression problems, and the like.

Figure 8B:
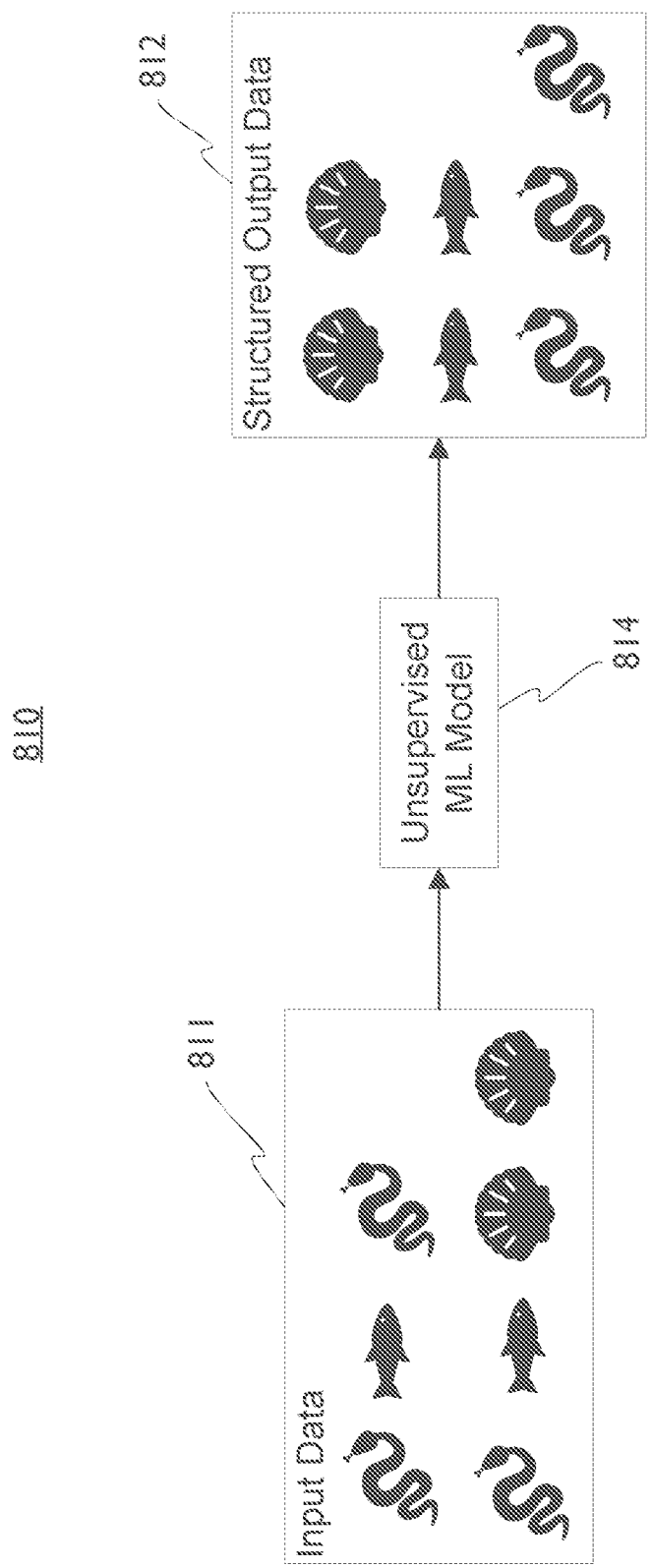

Machine learning may be unsupervised (e.g., unsupervised learning). FIG. 8B illustrates an example unsupervised learning framework 810. An unsupervised learning algorithm 814 may train on a dataset that may contain inputs 811 and may find a structure 812 (e.g., pattern detection and/or descriptive modeling) in the data. The structure 812 in the data may be similar to a grouping or clustering of data points. As such, the algorithm 814 may learn from training data that may not have been labeled. Instead of responding to supervisory feedback, an unsupervised learning algorithm may identify commonalities in training data and may react based on the presence or absence of such commonalities in each training datum. For example, the training may include operating on a training input data to generate an model and/or output with particular energy (e.g., such as a cost function), where such energy may be used to further refine the model (e.g., to define model that minimizes the cost function in view of the training input data). Example algorithms may include Apriori algorithm, K-Means, K-Nearest Neighbors (KNN), K-Medians, and the like. Example problems solvable by unsupervised learning algorithms may include clustering problems, anomaly/outlier detection problems, and the like.

Machine learning may be semi-supervised (e.g., semi-supervised learning). A semi-supervised learning algorithm may be used in scenarios where a cost to label data is high (e.g., because it requires skilled experts to label the data) and there are limited labels for the data. Semi-supervised learning models may exploit an idea that although group memberships of unlabeled data are unknown, the data still carries important information about the group parameters.

Machine learning may include reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP)) and may be used when exact models may not be feasible. Reinforcement learning algorithms may be used in autonomous vehicles or in learning to play a game against a human opponent. Examples algorithms may include Q-Learning, Temporal Difference (TD), Deep Adversarial Networks, and/or the like.

Reinforcement learning may include an algorithm (e.g., agent) continuously learning from the environment in an iterative manner. In the training process, the agent may learn from experiences of the environment until the agent explores the full range of states (e.g., possible states). Reinforcement learning may be defined by a type of problem. Solutions of reinforcement learning may be classed as reinforcement learning algorithms. In a problem, an agent may decide an action (e.g., the best action) to select based on the agent's current state. If a step if repeated, the problem may be referred to as an MDP.

For example, reinforcement learning may include operational steps. An operation step in reinforcement learning may include the agent observing an input state. An operation step in reinforcement learning may include using a decision making function to make the agent perform an action. An operation step may include (e.g., after an action is performed) the agent receiving a reward and/or reinforcement from the environment. An operation step in reinforcement learning may include storing the state-action pair information about the reward.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of machine learning's training process may be a model for predicting outcome(s) on a new dataset. For example, a linear regression learning algorithm may be a cost function that may minimize the prediction errors of a linear prediction function during the training process by adjusting the coefficients and constants of the linear prediction function. When a minimal may be reached, the linear prediction function with adjusted coefficients may be deemed trained and constitute the model the training process has produced. For example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function to minimize classification errors by adjusting the biases and weights through a process of feedforward propagation and backward propagation. When a global minimum may be reached, the optimized hypothesis function with its layers of adjusted biases and weights may be deemed trained and constitute the model the training process has produced.

Data collection may be performed for machine learning as a first stage of the machine learning lifecycle. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronic medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR.

Data preparation may be performed for machine learning as another stage of the machine learning lifecycle. Data preparation may include data preprocessing steps such as data formatting, data cleaning, and data sampling. For example, the collected data may not be in a data format suitable for training a model. Such data record may be converted to a flat file format for model training. Such data may be mapped to numeric values for model training. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated.

Model training may be another aspect of the machine learning lifecycle. The model training process as described herein may be dependent on the machine learning algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to reduce overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning lifecycle. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning cycle. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

ML techniques may be used independently of each other or in combination. Different problems and/or datasets may benefit from using different ML techniques (e.g., combinations of ML techniques). Different training types for models may be better suited for a certain problem and/or dataset. An optimal algorithm (e.g., combination of ML techniques) and/or training type may be determined for a specific usage, problem, and/or dataset. For example, a process may be performed to for one or more of the following: choose a data reduction type, choose a configuration for a model and/or algorithm, determine a location for the data reduction, choose an efficiency of the reduction and/or result, and/or the like.

For example, a ML technique and/or combination of ML techniques may be determined for a particular problem and/or use case. Multiple data reduction and/or data analysis processes may be performed to determine accuracy, efficiency, and/or compatibility associated with a dataset. For example, a first ML technique (e.g., first set of combined ML techniques) may be used on a dataset to perform data reduction and/or data analysis. The first ML technique may produce a first output. Similarly, a second ML technique (e.g., second set of combined ML techniques) may be used on the dataset (e.g., same dataset) to perform data reduction and/or data analysis. The second ML technique may produce a second output. The first output may be compared with the second output to determine which ML technique produced more desirable results (e.g., more efficient results, more accurate results). Multiple ML techniques may be compared with the same dataset to determine the optimal ML technique (s) to use on a future similar dataset and/or problem.

In examples, in a medical context, a surgeon or healthcare professional may give feedback to ML techniques and/or models used on a dataset. The surgeon may input feedback to weighted results of a ML model. The feedback may be used as an input by the model to determine a reduction method for future analyses.

In examples, a data analysis method (e.g., ML techniques to be used in the data analysis method) may be determined based on the dataset itself. For example, the origin of the data may influence the type of data analysis method to be used on the dataset. System resources available may be used to determine the data analysis method to be used on a given dataset. The data magnitude, for example, may be considered in determining a data analysis method. For example, the need for datasets exterior to the local processing level or magnitude of operational responses may be considered (e.g., small device changes may be made with local data, major device operation changes may require global compilation and verification).

Such ML techniques may be applied to surgical information (e.g., a combination of information flows of surgical information in FIG. 7) to generate useful ML models.

Figure 9:
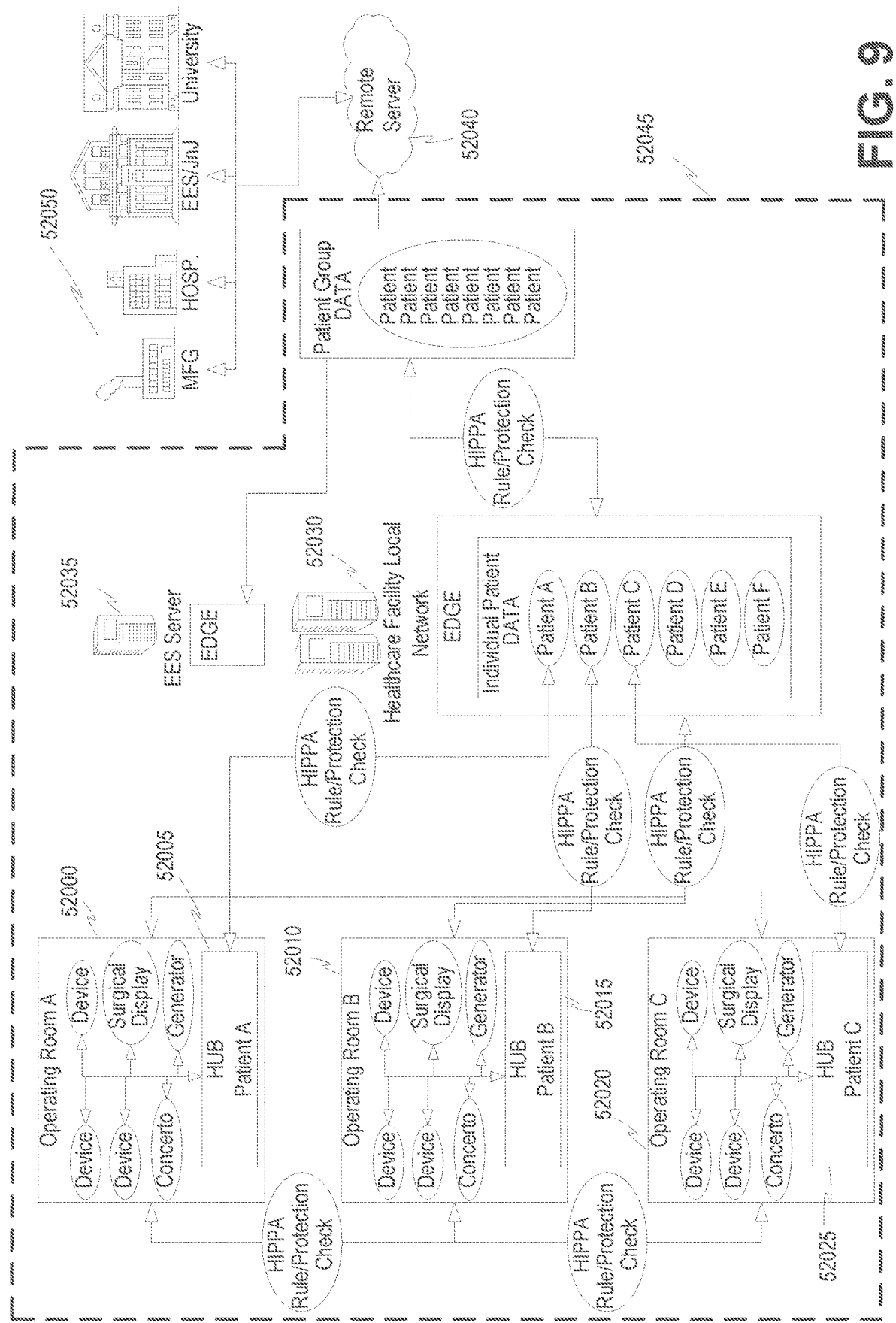
FIG. 9 is a block diagram of an example surgical system.

FIG. 9 is a block diagram of an example surgical system. The system may enable the communication of information among one or more operating rooms 52000, 52010, 52020, a corresponding hospital local network 52030, an edge server 52035, and one or more other entities 52050.

In an example, each of the operating rooms 52000, 52010, 52020 may include a respective surgical computing device (e.g., surgical hub 52005, 52015, 52025). The surgical hubs 52005, 52015, 52025, as illustrated, may include instances of the surgical computing device 704 for example, disclosed here. For example, the surgical hubs 52005, 52015, 52025 may include instances of the hub described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Each surgical hub 52005, 52015, 52025 may be associated with one or more devices to be used during a surgery, such as surgical generators, intelligent surgical instruments, surgical robots, surgical displays, sensors, and the like. Example intelligent surgical instruments may include those described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example. An example robotic system may include that described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety. Such devices may be used in a surgical procedure as part of the surgical system.

Such devices and the corresponding surgical hubs 52005, 52015, 52025 may generate, process, send, and/or receive information, such as surgical information disclosed in FIG. 7A for example. In an example, the surgical information may include that associated with one or more patient biomarkers (e.g., information disclosed U.S. patent application Ser. No. 17/156,28, filed Nov. 10, 2021, the disclosure of which is herein incorporated by reference in its entirety). This surgical information may be analyzed For example, such analysis may include that disclosed in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

A respective patient may be undergoing a surgical procedure in each of the operating rooms 52000, 52010, 52020. As illustrated, patient A may be undergoing a surgical procedure in operating room A 52000. Patient B may be undergoing a surgical procedure in operating room B 52010. And patient C may be undergoing a surgical procedure in operating room C 52020. The surgical information generated, processed, sent, an/or received by each of the hubs 52005, 52015, 52025 may be associated with the patient undergoing surgery in the corresponding operating room. Surgical information associated with different patients in a common network and/or networked devices, such as the hospital local network 52030, the edge server 52035, and/or other entities for example, may pose data privacy challenges and may promote the use of data privacy protection approaches such as those disclosed herein.

Surgical information, such as patient specific surgical information, may be communicated via a common network and/or networked devices, such as the hospital local network 52030, the edge server 52035, and/or other entities. To illustrate, surgical information associated with the surgical procedure performed on patient A in operating room A 52000 may be communicated between the surgical hub device 51005 in operating room A 52000 and the edge server 52035 via the hospital local network 52030. Similarly, surgical information associated with the surgical procedure performed on patient B in operating room B 52010 may be communicated between the surgical hub device 51015 in operating room B 52010 and the edge server 52035 via the hospital local network 52030. Likewise, surgical information associated with the surgical procedure performed on patient C in operating room C 52020 may be communicated between the surgical hub device 51025 in operating room C 52020 and the edge server 52035 via the hospital local network 52030.

Such surgical information may have the characteristic of individuality (e.g., data individuality). Data individuality or data individuality level may represent how likely the surgical information is to be linked to an individual patient. For example, surgical information with high data individuality level may have a high likelihood of being traced back to a specific patient. For example, surgical information with low data individuality level may have a low likelihood of being traced back to a specific patient. And surgical information with moderate data individuality level may have a moderate likelihood of being traced back to a specific patient.

Data individuality level may be highly correlated with particular data types. For example, biographical data (e.g., patient's name, patient ID, surgical procedure date/time, etc.) and/or surgical information tagged with biographical data may be associated with high data individuality. Likewise, data types associated with relatively generic medical data (e.g., data types with values common to many patients) may have low data individuality level. For example, patient weight may be data type with low data individuality level (because, for example, many patients may have the same body weight).

Data individuality level may be correlated with the specificity of the data taken as a whole. For example, data elements, viewed individually, may have a low data individuality to the extent that any such element taken alone would not likely reveal the patient from whom the data originated. However, such data elements, taken together as a whole, may be more likely to reveal the patient from whom the data originated. Such data elements, taken together as a whole, may exhibit high data individuality.

Data individuality level of a surgical data set associated with a patient may reflect the patient specificity of its subsets. For example, a surgical data set may have high data individuality level because most or all of its subsets may contain information that would reveal the patient source of information. In this example, a surgical data set may have high data individuality level because a small subset of the data has a relatively high likelihood of revealing the patient source of information and the remaining large complement subset of the data has a relatively low likelihood of revealing the patient source of information.

The data individuality surgical of surgical information may be changed (e.g., lowered). Anonymization techniques may be used to reduce the data individuality of surgical information. Anonymization techniques may include any logical processing of information that makes it less likely to decern its patient source. For example, anonymization techniques may include techniques such as redaction, randomization, aggregation and/or averaging, and/or the like. Redaction may include removing subsets of surgical data with high data individuality and preserving subsets of surgical data with low data individuality. In an example, redacting patient name and patient's ID from a data set may reduce the data individuality of a data set. Randomization may include modifying certain aspects of data with noise to conceal the origin of the data without significantly changing the surgical and/or analytical value of the information. For example, randomizing the time-of-day information for certain surgical information may help conceal the patient origin of such data without affecting the broader analytical value of the information in view of a larger population study. Data averaging an aggregate of common values across similarly situated patients reduces the likelihood that such an average may be traced back to a particular patient.

In a system, a desired data individuality level may be related to the data's use and/or location in the system. For example, data individuality for surgical information being analyzed within an operating room during a patient procedure may be left unchanged. Here, a reduction in data individuality may not be desired. Here, the privacy concern associated with such a high data individuality is minimal because the use and/or location of the data in the system is localized to the patient's surgical operation and operating room. For example, data individuality level for surgical information being analyzed in a university and/or academic setting may be reduced. Here, a reduction in data individuality level is desired because the privacy concern associated with such a high data individuality is greater because the use and/or location of the data in the system is distant from the patient's surgical operation and operating room.

A hierarchy may be used to determine a desired data individuality level in a system. For example, a surgical system may have one or more hierarchical levels. The levels may be logical levels, for example. The levels may be physical levels, for example. The levels may each, for example, based on the location in the hierarchy, be associated with a corresponding data individuality. In an example, uses and/or locations of surgical data that are more localized to the healthcare of a particular patient may have a level associated with a desired high data individuality. And uses and/or locations of surgical data that are distant to the healthcare of a particular patient may have a level associated with a desired low data individuality level. To illustrate, the use of data and systems when performing analytical research across many patients and/or many surgical procedures may be distant from the healthcare of any one particular patient and, therefore, may be associated with a desired low data individuality.

Data individuality level may change based on the location of a processing device in system hierarchy where the surgical information may be processed or sent for processing, as described herein. In example, data individuality level associated with surgical information may be changed from high data individuality level to low data individuality level, if/when the surgical information is sent for processing from the local entity that is located inside a protected boundary to a remote processing device that is located outside the protected boundary (e.g., a remote enterprise server). The transformation of the individuality level of the surgical information from a high data individuality level to low data individuality level may be performed using one of the anonymization techniques, as described herein.

In an example, data individuality may be transformed from high data individuality to medium data individuality, for example, if surgical information is sent from a processing (e.g., a surgical hub) located inside a protected boundary to a processing device that is located in an intermediate network with moderate protection. The intermediate hierarchical level may be located within a healthcare professional's network, but outside the protected boundary, as described in FIG. 10.

Transforming surgical information by changing its data individuality level may include anonymizing at least a portion of the surgical information or a data set. Surgical information, surgical data set, or data set may be used interchangeably herein. For example, by redacting a subset of data points of high data individuality level thereby changing the data individuality level from high data individuality to low data individuality level. In an example, changing data individuality level may include processing data sets (e.g., aggregating data sets) into a form where the data points of a data set are aggregated or pooled into one total data set. Data points in the total data set may not be tied to individual data sets.

Edge processing may balance privacy and comprehensiveness using balancing protocols to package the surgical data for sharing within differing levels of the system hierarchy. The surgical data sets may experience allometry (e.g., growth of the parts at different rates resulting in changes in proportions) of data individuality. The allometry of surgical data (e.g., growth or reduction of the size of surgical data or surgical information) may be directly proportional to the level of protection provided by a system hierarchy level. Surgical data packages (e.g., surgical data sets) may change the surgical data magnitude and the surgical data comprehensiveness as they are processed and/or passed through different levels of the system hierarchy. The growth or reduction of the surgical data or surgical data portions (e.g., separable surgical data portions) not be linear. In an example, the growth or decay of the surgical data or surgical data portions may be proportional to the protection level associated with the surgical data, for example, the protection level provided by the surgical data protection rules (e.g., HIPAA rules) or protection level associated with the networks within which the surgical data resides. In an example, the higher level of surgical data protection may result in more individuality of the surgical data points or a surgical data set.

Constitution of individual constituent data components may be based on the level of the data within the overall system hierarchy or protection level of the system. In examples, the data and/or algorithms may undergo assimilation and/or aggregation as the data is pushed down from higher levels of the system hierarchy (e.g., a remote server) to a lower levels of the system hierarchy (e.g., the surgical hub).

In an example, as illustrated in FIG. 9, the data may maintain the same data individuality level (e.g., high data individuality level which may include each of the data points within a data set) if it is sent to a processing device, for example, an edge server 52035 that is located within the hospital local network 52030, where the network is within a protected boundary 52045 (e.g., health insurance portability and accountability act (HIPAA) protection boundary). In such a case, data with high individuality level may be allowed since the data is less vulnerable to be traced back to a patient.

In an example, a local processing device may determine that instead of processing the data at an edge server 52035 that is located within a protected boundary of a hospital local network 52030, the data should be processed on a processing device that is located outside the protected boundary of the healthcare facility's network. Data individuality level of surgical information in such a case may be reduced (e.g., from high data individuality level to low data individuality level) before the surgical information is sent from a processing device (e.g., edge server 52035) that is located inside the protected boundary 52045 of a healthcare facility to a processing device (e.g., remote sever 52040) that is located outside the protected boundary 52045 of the healthcare facility.

Determining the individuality of the data as it passes through different levels of the system hierarchy may be determined based on a rule check (e.g., HIPAA rule check located within the analysis subsystem of the surgical hub/edge device). The rule check may be implemented as a check whether surgical information or a portion of surgical information is associated with a patient and/or the surgical information can be traced back to the patient. In an example, the rule check may be implemented using a machine learning model that may be trained to generate a data individuality based on an analysis and/or comparison of the data points within a surgical data set. The machine learning technique utilized may be based on a supervised learning framework, for example, as described in FIG. 8A. In such a case, the training data (e.g., training examples 802, as illustrated in FIG. 8A) may consist of a set of training examples (e.g., input data mapped to labeled outputs, for example, as shown in FIG. 8A). The training data used in training the local machine learning model 52090 may include surgical data sets gathered from previous surgical procedures, surgical parameters associated with those surgical procedures and/or simulated surgical procedures. The training data may include resource availability (e.g., memory and/or processing capacity availability) of various processing devices from previous surgical procedures, control algorithms associated with the surgical instruments (e.g., stored locally or received from other entities, e.g., a remote server).

In an example, machine learning utilized may be unsupervised (e.g., unsupervised learning), as described in FIG. 8B. As illustrated in FIG. 8B, in an unsupervised learning framework-based machine learning model may train on a dataset that may contain inputs and may find a structure or a pattern in the data. For example, the inputs may include parameters associated with data set to be processed (e.g., size of the data set, acceptable latency values, etc.), a rule set (e.g., based on the local privacy laws where the surgical procedure is performed), and parameters associated with various potential processing devices where the data set may be sent for processing. The outcome may be identification of one or more processing devices and/or system hierarchy levels where the data set may be sent for processing and/or the data individuality level that may be applied to the data set before sending it to the selected processing device. The data individuality level may be selected based on where the data set is sent for processing.

In an example, a machine learning algorithm may be trained to determine the individuality level of the data. For example, a histogram (or other method of estimate a probability distribution) may be generated to work out the standard deviation of the historical data. The deviation from the mean of a given data point can then be compared to the standard deviation or other predetermined range to classify the data point with a predetermined data individuality level.

In an example, the machine learning model may assign risks to each of the data points of the dataset based on previous data a machine learning model may have been trained with. The model may suggest a total data individuality level to be applied the dataset, for example, based on the accumulation of the risks of the data points within the data set. This individuality may be compared with the local applicable rule set to identify: (1) the system hierarchy level and/or the processing device the dataset may be sent for processing, (2) the data individuality level that may be applied to the data set (e.g., before sending it out from processing). The rule set may be derived from the protection rules (e.g., HIPAA rules) the healthcare facility where the surgical procedure is being performed may have to adhere to.

In an example, a surgical hub/edge device may identify the processing device and/or the system hierarchy level where a surgical data set may be sent for processing. The processing device and/or the system hierarchy level may be identified based on, for example, the surgical data set magnitude (e.g., size of the surgical data set), capabilities of the processing server, performance metrics associated with the data set, etc. Capabilities and characteristics may be used interchangeably herein. In an example, a surgical hub/edge device, for example, based at least on the size of a surgical data set to be processed, may determine that the surgical data set should be processed at a remote server with a processing power that is higher than the processing power of the surgical hub or the edge server. In such a case, the surgical hub/edge device may send the surgical data set to a remote server. Based on the identification of the processing device and/or the system hierarchy level, the surgical hub/edge device may perform a rule check to determine the data individuality level at which the data set should be sent to the processing device.

In an example, a surgical hub/edge device may identify the processing device and/or the system hierarchy level based on at least one of the capabilities of the processing device, the data magnitude of the surgical data, the sensitivity to latency in processing the surgical data, the data individuality level of the surgical data, or the intended use of the surgical data. Identifying the processing device may be performed using one or more look-up tables which may be combined, with optional prioritization between the look-up tables. For example, a look-up table may associate data magnitude with processing device capabilities to identify a suitable processing device for a given data magnitude. Similarly, intended use of data could be associated with the capabilities of the processing devices, e.g., if the intended use is for treatment of the patient this may be associated with a processing device with lower capability, whereas the intended use being analysis of data alongside other similar data for trend or correlation analysis, may be associated with a processing device of higher capability. Another look-up table may associate data individuality level with the location of the processing device. For example, a processing device located inside a protected boundary may have higher individuality level associated with it than a processing device that is located outside the protected boundary.

Combining the look-up tables, data with an intended use associated with a lower capability and lower individuality level may be sent to a processing device of higher capability if the data magnitude requires it. The processing device may be located outside a protected boundary. The capabilities of the processing devices may increase when moving from the operating room, e.g., with the operating room processing device (e.g., the surgical hub) having a lower capability than a hospital processor, which has a lower capability than a hospital network processing device, which has a lower capability than a remote processing device.

In an example, performance metrics (e.g., along with the rule set) may be considered by the surgical hub/edge device to determine the processing device and/or system hierarchy level where the data may be sent for processing. Determining the performance metrics for the data may involve using simulations which may output approximations for performance metrics associated with the data. Simulation framework may be described in "Method for Surgical Simulation" in U.S. patent application Ser. No. 17/332,593, filed May 27, 2021, the disclosure of which is herein incorporated by reference in its entirety. In an example, based on a determination whether or not the data set to be processed is sensitive to latency (e.g., the processing/transit delays), the data set may be sent for processing to an edge server that may be located within a healthcare's providers local network and therefore associated with lower latency level or to a remote server that may be associated with a higher latency level as is described herein.

In an example, a surgical data set may be prepared to be sent for processing to a processing device with the result to be utilized for a post-surgical follow-ups, recovery, monitoring etc. of the patient. In such a case, the latency or time taken for processing the data set may not be of importance. The surgical hub/edge device in such a case, based on at least the latency not being a factor and/or the benefit the diverse data set at a remote server (e.g., a centrally located server) may determine to send the surgical data set for processing to a remote server.

In an example, data magnitude of a surgical data set may be associated with a data individuality level. Data magnitude may be used in determining a data individuality level that may be applied to the surgical data set before sending it for processing to a processing device. In an example, a surgical data set of high data magnitude may be associated with high data individuality level, and low data magnitude may be associated with low data individuality level.

Transforming a data individuality level from one level to another may include anonymizing (e.g., redacting, randomizing, averaging, etc.) at least a portion of a surgical data set. Anonymizing a surgical data set may result in the surgical data set being less likely or impossible to be traced back to an individual patient. In an example, a local hub may determine to send a surgical data set associated with a surgical procedure to a remote server 52040 based on the remote server 52040 being the best candidate for processing the data, as described herein. Based on this determination, the local hub may anonymize (e.g., redact, randomize, average, etc.) the data. For example, data associated with patient A 52005 may be randomized, in a manner that the randomized data cannot be traced back to patient A 52005.

As described herein, anonymization techniques such as redaction, summarization, and/or compilation of data may be used on the surgical data set as the surgical data set is pushed up to a higher system hierarchy level (e.g., a cloud server), where there may be decreasing levels of protectivity of the privacy of the data. In an example, as the surgical data set is prepared to be sent to and/or shared with a processing device located in a higher system hierarchy level, the security of the data may be considered by the machine learning algorithm, for example. In an example, one or more parameters associated with the surgical data set may be categorized with respect to their relevance or need to have individual aspects viewable. In such a case, the system may combine specific individual surgical data points of a surgical data set and average or summarize surgical data points together within the surgical data set (e.g., data structure), which may result in not losing the trends and preventing individualization of datasets from specific patients. As described herein, portions of the data may be summarized and/or aggregated to produce pools of data that may be mixed, homogenized and/or aggregated, and may allow them to convey the same average result while preventing the individual constituent parts of a surgical data set to be separated.

In an example, encryption (e.g., a high-grade encryption) may be used to secure surgical data associated with a patent. The level of encryption used may depend on whether or not a surgical data set is being sent for processing to device that is located within a healthcare provider's protected boundary.

Determining where to process a surgical data set associated with a patient and/or a healthcare professional may be based on the degree of advantage the surgical data set may obtain from being processed at a certain hierarchical level. For example, a centrally located remote server 52040 may have access to diverse data sets it may have received from multiple locations of same or different healthcare providers. The level of the diversity of data may be proportional to the degree of advantage it may provide while processing a data set. In an example, a remote server may be capable of analyzing certain surgical data sets within a specific time frame. In an example, determining where to process a surgical data set may be based on the speed at which the surgical data set can be processed at a processing device that is located at certain level of the system hierarchy (e.g., data sent to a remote server 52040 may be processed faster than data sent locally).

Data individuality level may change based on anonymization of some or all of the data points within a surgical data set. Anonymization may include removing or altering one or more data points from a surgical data set, as described herein with respect to FIG. 10. The anonymization of the surgical data points that may be anonymized may be associated with an assigned high risk, for example, as determined by the machine learning model located in the surgical hub. For example, an identifying characteristic data point may be associated with a high risk and, therefore, may be anonymized from the surgical data set before sending the transformed surgical data set to a processing device (e.g., a remote server). In an example, the same data point may be included in a surgical data set if the surgical data set is sent to a processing device (e.g., an edge server 52035) that is located within a hospital's local network 52030 that is within the protective boundary 52045.

In an example, the surgical hub may weigh individualized surgical data set against privacy risks associated with the surgical data set, when determining the system hierarchy level that may be selected for sending the surgical data set for processing. Privacy risks may be pre-configured and/or may be a part of a machine learning model. In an example, the magnitude of a surgical data set may be derived based on the level of data individuality applied to that surgical data set.

In an example, a surgical data set that is generated within a healthcare facility's network (e.g., locally within the operating rooms of a healthcare facility) may allow for the surgical data set to be checked based on a protection rule (e.g., HIPAA rule). A surgical data set sent from a healthcare facility's edge network to a remote server (e.g., cloud server) may combine each of the surgical data points into one output. In such a case, the surgical data set sent may combine the distribution of all the patients' surgical data in a manner such that it may not be tied or tracked back to a particular patient.

In an example, during a surgical procedure, a surgical data set may be collected on each of the patient biometrics, supplies used, complications, and/or outcomes (e.g., locally within a healthcare facility for any follow-ups, recovery, and/or monitoring). If the information is to be sent outside the healthcare facility, the data may be combined into one combined surgical data set and sent to the remote server (e.g., cloud or any edge network that may not be a part of the healthcare facility). The information may be sent outside the healthcare facility using a distribution, a range, a minimum and a maximum value, so that the combined surgical data set may not be tied back to an individual patient.

Figure 10:
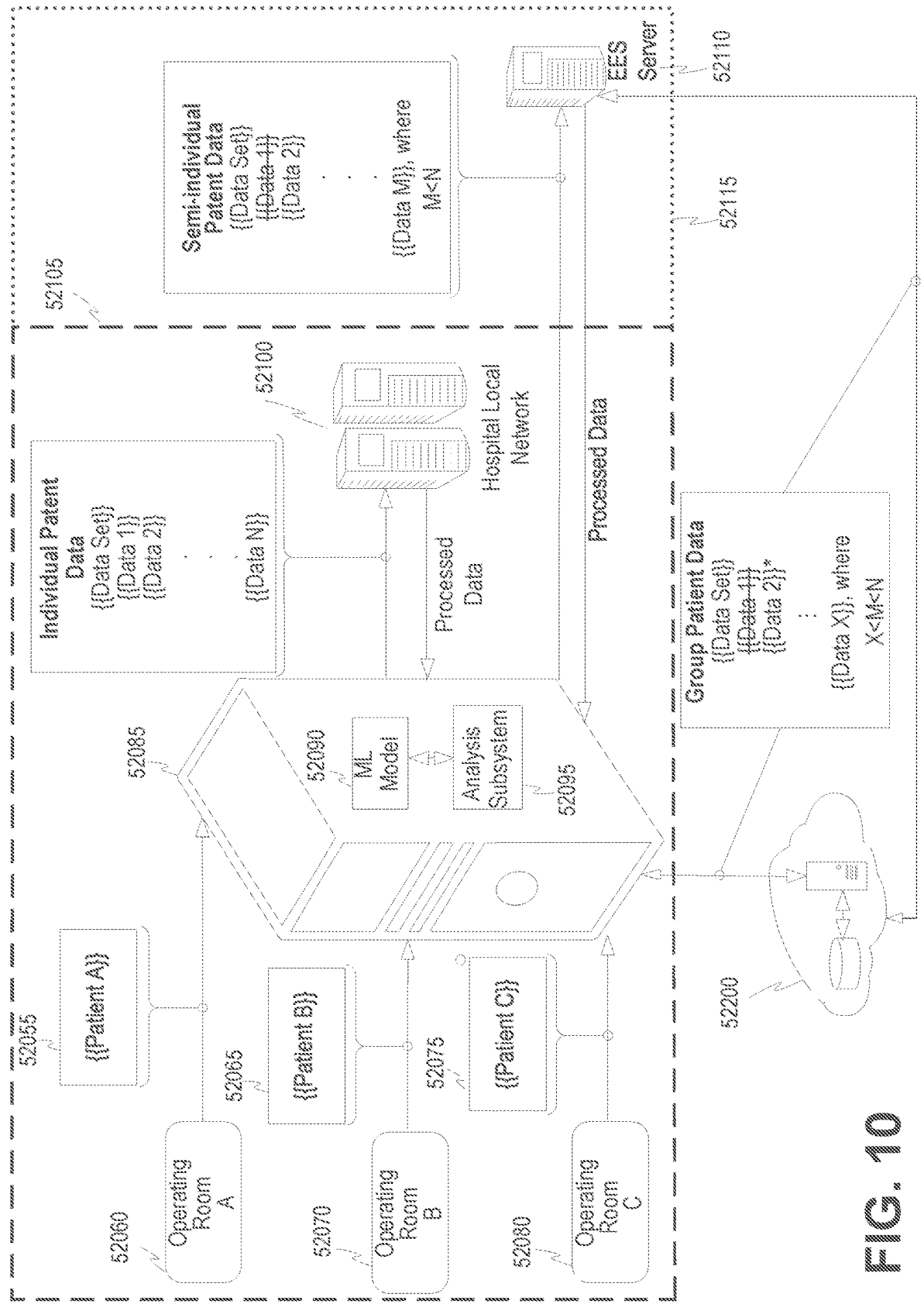
FIG. 10 illustrates an example of determining data individuality level based on a system hierarchy level where the surgical data may be sent for processing.

FIG. 10 illustrates an example of determining data individuality level based on a system hierarchy level where the surgical data may be sent for processing. As shown in FIG. 10, surgical data may be associated with patient A 52055 having a surgical procedure being performed on the patient in operating room A 52060, associated with patient B 52065 having a surgical procedure being performed in operating room B 52070, and/or associated with patient C 52075 having a surgical procedure being performed in operating room C 52080. The surgical data may be sent (e.g., sent via messages) to a local surgical hub/edge device 52085. The surgical data may be generated from one or more surgical instruments located in each of the operating rooms. The surgical data may be generated based on measurements taken using sensors, actuators, robotic movements, biomarkers, surgeon biomarkers, visual aids, billing, and/or the like. In an example, surgical data to be processed may be generated based on a visual tracking system located within each of the operating rooms. For example, the visual tracking system may include facial recognition system, which may produce data related to the status of the patient and/or surgeon during the surgical procedure.

The surgical data sent from the surgical instruments in the operating rooms to respective local surgical hubs may be in raw form (e.g., without any processing done to it). The raw measurement data may be converted by the local surgical hub into data points. A machine learning model 52090 and/or the analysis subsystem 52095 that are a part of the local surgical hub/edge device 52085, may be used to predict the location of a processing device (e.g., a processing device in a system hierarchy level) where the surgical data may be sent for processing. For example, the local hub 52085 may determine to send the surgical data to a processing device (e.g., an edge server 52100) that is located within the hospital's local network. The hospital's local network may be a part of a protected boundary 52105. In such a case, the local hub 52085 may send the surgical data with high data individuality and data magnitude to the server 52100 located with the protected boundary 52105.

As described with respect to FIG. 10, data sent from the surgical hub/edge device 52085 to the edge server 52100 may be organized into one or more surgical data sets. A surgical data set may include surgical data points (e.g., parameters associated with a patient, healthcare provider, and/or a surgical instrument) 1, 2, . . . N, where N is a finite number. Surgical data points 1 through N may be associated with patients A 52055, B 52065, and/or C 52075. In an example, a surgical data set with surgical data points 1 through N may be associated with a high data individuality due to surgical data points 1 and 2 having a high risk of being linked back to patient A 52055. As illustrated in FIG. 10, in a case where the surgical data is being sent to a processing device located within the protected boundary 52105 (e.g., an edge server 52100), surgical data points 1 and 2 may be included in that surgical data set. In an example, surgical data points 11 through 20 may be associated with patient B 52065 and surgical data points 19 and 20 may be of type that may have a risk of being traced to patient B. Since the surgical data is being sent within the protective boundary 52105, the surgical data may be included within the surgical data set. In an example, surgical data points 30 through 40 may be associated with patient C 52075. Surgical data points 35 and 36 may be traced to patient C 52075. Since this surgical data is being sent within the protected boundary 52105, it may be included in the data set that may be sent to the edge server 52100.

In an example, the local surgical hub/edge device 52085 may determine that a surgical data set, for example, surgical data set associated with patient A 52055, patient B 52065 and/or patient C 52075 may be sent for processing to a processing device (e.g., server 52110) that may be located within an intermediate system hierarchy level. The intermediate system hierarchy level 52110 may be associated with a semi-protected boundary 52115. Server located at the intermediate system hierarchy level 52110 may have moderate processing power when compared to local servers 52100 (e.g., has least processing power) and remote servers 52200 (e.g., most processing power). In an example, the server may be located within an extended healthcare facility network. For example, the healthcare facility may have an agreement with some partner healthcare facilities about sharing the patient data. In such a case, the network shared by these hospitals may be considered within the semi-protected boundary 52115. Surgical data set sent to server(s) within this network may adhere to a moderate data individuality level. Surgical data set with moderate individuality level may have less individuality than the surgical data set that is located within a healthcare facility's protective boundary and more individuality than the surgical data set that may be sent outside of the protected/intermediate boundary. The different individuality levels may be achieved by anonymizing the data (e.g., redacting, randomizing, averaging, etc.), as described herein.

As shown in FIG. 10, the surgical data set sent to the intermediate system hierarchy level 52110, for example, may include M out of N surgical data points, where M is less than N (e.g., N is the total number of surgical data points that were generated within a healthcare facility's protective boundary 52105). The surgical data points that were removed or anonymized may be the surgical data points that may have high risk of being traced to an individual patient. Surgical data form and surgical data individuality may be used interchangeably herein.

In an example, as illustrated in FIG. 10, out of the surgical data points 1 through N associated with patient A 52055, surgical data points 1 and 2 may have high individuality and may reveal information that may trace it back to patient A 52055. In an example, surgical data point 1 may be the patient's name, patient ID, identification of the surgical procedure performed in the patient, etc. In such a case, because of the high individuality level, the surgical data point 1 may be redacted before a surgical data set it is a part of is sent for processing to any of the processing devices that are located outside the protected boundary 52105. In an example, surgical data point 2 may be associated with patient's physical features, for example, height, weight, etc. In such a case, surgical data point 2 may be deemed as not as likely to be traced back to patient A 52055 and may be sent in non-anonymized form to a device located in an intermediate hierarchical level, for example, within a healthcare facility's network 52115, but outside the protected boundary 52105. As illustrated in FIG. 10, in this case, the data magnitude M comprising the number of surgical data points M (data points N minus data point 1 that was anonymized and therefore not available for the processing device for analysis) may be less than the number of data magnitude N.

In an example, the data magnitude and/or the data individuality level associated with a hierarchical level may be related to the proportion of algorithm that may be utilized to process the data at that hierarchical level. For example, the proportion of algorithm used for processing surgical data points 1 through N of higher data individuality at the surgical hub/edge device 52085 may be higher than the proportion of algorithm used for processing surgical data points 1 through M (where M<N) at the server 52115 that is located within an intermediate hierarchical level, for example, within a healthcare facility's network 52115, but outside the protected boundary 52105.

In an example, the surgical hub/edge device may determine to send a surgical data set to a remote server 52200 located outside of the protective boundary 52105 and intermediate boundary 52115. The local surgical hub/edge device 52085 may identify the processing device using the machine learning model 52090 and/or analysis subsystem 52095 as described herein. For example, the machine learning model may identify a remote server 52200 based at least on the diversity of data sets available on the remote server 52200, performance metrics associated with the data, etc., as described herein. In such a case, in addition to anonymizing the surgical data point 1, the surgical hub/edge device 52085 may also anonymize the surgical data point 2 before sending both the surgical points for processing to the remote server 52200. As illustrated in FIG. 10, in this case, the data magnitude N' comprising the number of surgical data points N (data points N minus 2) may be less than the data magnitude M (N minus 1), which may be lesser than the data magnitude N. As illustrated in FIG. 10, as the surgical data set associated with a patient may be sent to various processing devices for processing, the data magnitude may grow or shrink based on the protection level provided by the hierarchical level where the processing device is located, or the data individuality level associated with that hierarchical level.

In an example, as described here, the surgical hub/edge device 52085 may send a surgical data set of magnitude M (N minus 1) to the processing device (server 52110) that is located in the intermedia hierarchical level and/or associated with an intermediate individuality level. The server may send the surgical data for further processing to the remote server 52200. In such a case, the server 52110 may further anonymize the surgical data set by, for example, randomizing data point 2 before sending the surgical data set of magnitude X (N minus 2, and where X<M<N) to the remote server 52200. In this case, the proportion of algorithm used for processing surgical data points 1 through \' (e.g., at remote server 52200) of lower data individuality may be lower than the proportion of algorithm used for processing surgical data points 1 through M (where X<M<N) at the server 52115 that is located within an intermediate hierarchical level, for example.

In an example, surgical data points 1 through 10 may be associated with patient A 52055 with surgical data point 1 and surgical data point 2 being traceable back to patient A 52055. In an example, the surgical data point 1 may be removed and data point 2 may be anonymized. In an example, these surgical data points may be fully anonymized (e.g., fully redacted, randomized, averaged, etc.) to where they are unable to be traced back to patient A 52055. In examples, the surgical data points of dataset X may be aggregated to a level where the surgical data cannot be traced back to any of patient A 52055, B 52065 and/or C 52075. In an example, surgical data points 10 through 20 may be associated with patient B 52065 and surgical data points 19 and 20 may be specific to B 52065 and may be traced back to patient B 52065. Both the surgical data points 19 and 20 may be redacted. In an example, the surgical data point 20 may be sent for processing in the surgical data set after being fully anonymized. Surgical data points 30 to 40 may be associated with patient C 52075. Surgical data points 35 and 36 may be specific to patient C 52075 and may be traced back to patient C 52075. Both data points may be removed (e.g., redacted). In such a case, the transformed surgical data may be associated with low data individuality and low data magnitude.

In an example a mathematical operation may be used to manipulate surgical data to change data individuality (e.g., remove any risk of the surgical data being associated or linked back to the patient). For example, an average and/or median may be taken among the surgical data points. Some of the surgical data points within the surgical data set may be manipulated to where they cannot be linked back to an individual patient, while other surgical data points within the surgical data set may be left unaltered. This may reduce the data individuality associated with the surgical data set while allowing the surgical data set to be sent to either the intermediate system hierarchy level 52110 or the remote level 52200.

Figure 11:
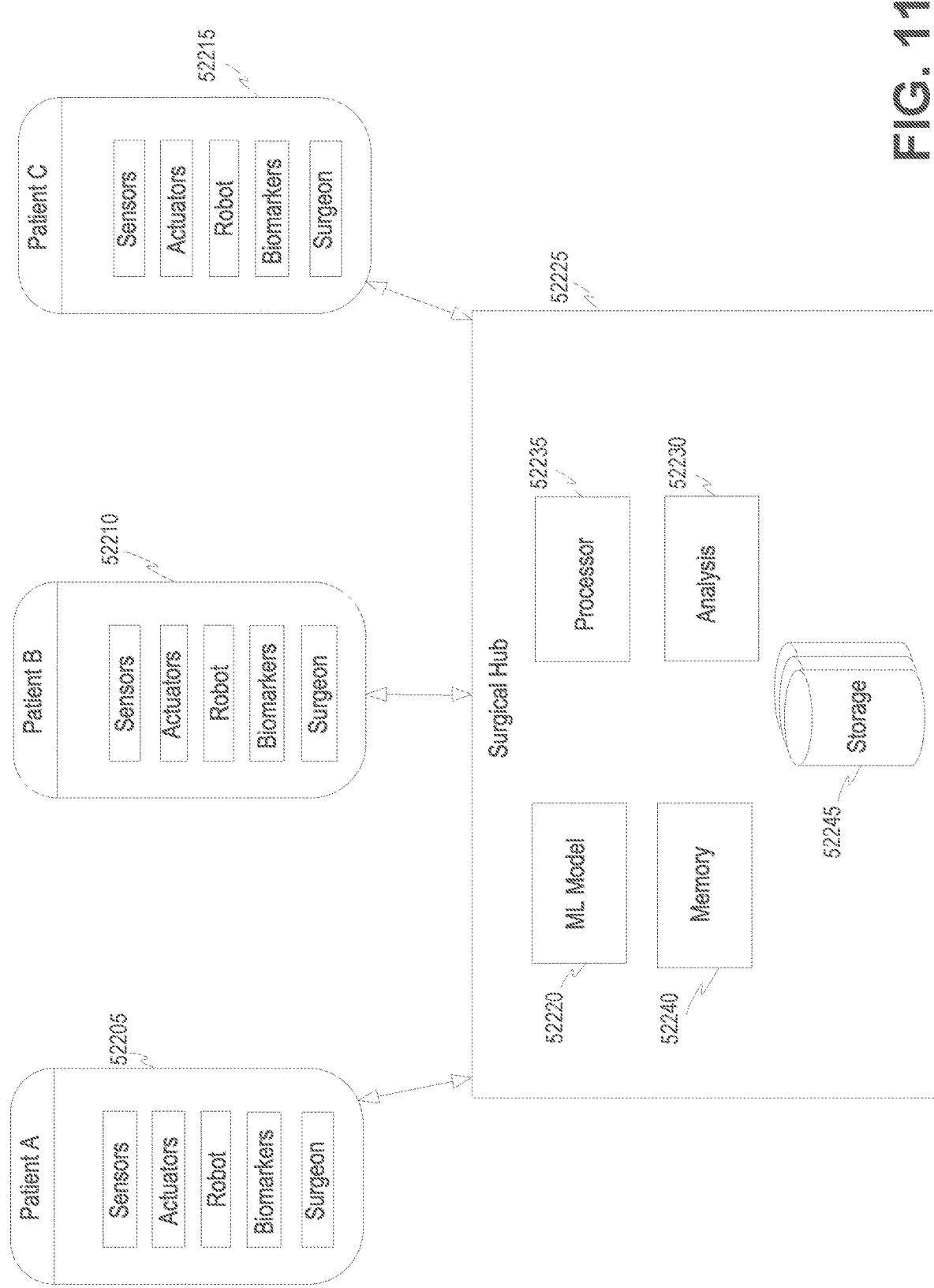
FIG. 11 illustrates an example of a surgical system where measurements taken within in operating rooms are received for processing by one or more respective the surgical hub/edge devices.

FIG. 11 illustrates an example of a surgical system where measurements taken within in operating rooms are received for processing by one or more respective the surgical hub/edge devices. As illustrated in FIG. 11, a surgical hub 52225 may include a processor 52235, a memory 52240) (e.g., a non-removable memory and/or a removable memory), an analysis subsystem 52230, a machine learning model 52220, and/or a storage subsystem 52245, among others. It will be appreciated that a surgical hub 52225 may include any sub-combination of the foregoing elements/subsystems while remaining consistent with an embodiment.

The processor 52235 in the surgical hub 52225 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52235 may perform data processing of surgical information it may receive from various surgical device and instruments attached to the surgical hub. The processor 52235 may perform data processing, authentication, input/output processing, and/or any other functionality that may enable the surgical hub 52225 to operate in an environment that is suitable for performing surgical procedures. The processor 52235 in the surgical hub 52225 may be coupled with a transceiver (not shown). The processor 52235 in the surgical hub 52225 may use the transceiver to communicate with other edge servers and/or remote servers, as described with respect to FIG. 9 and FIG. 10.

The processor 52235 in the surgical hub 52225 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52235 in the surgical hub 52225 may access information from, and store data in an extended storage 52245. (e.g., a non-removable memory and/or the removable memory). In an example, the processor 52235 in the surgical hub 52225 may process data points associated with a patient and determine a risk level associated with the data points and apply an individuality level associate with the risk level and/or a hierarchical level where the data points may be sent for further processing.

As described with respect to FIG. 10, a surgical data set may include multiple surgical data points. Surgical data points may be obtained from measurement data associated with a patients, a healthcare professional, etc. For example, a surgical data point may be associated with a measurements taken from a sensor, an actuators, a robotic movement, a patient biomarkers, a surgeon biomarker, a visual aid, and/or the like. Wearable devices could be used for those measurements. The wearable devices or wearables are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety. Each surgical data point may have a data individuality level associated with it. The data individuality level may be associated with a risk level. The risk level may indicate whether or not a surgical data point can be traced or linked back to the patient. An overall risk level may be attributed to the surgical data set. The overall risk level, among other things, may be based on the aggregation of the risk levels of each of the surgical data points within a surgical data set.

In an example, the measurements may be associated with one of more actuators located within the operating room. For example, measurements may be generated based on potentiometer readings located on a surgical instrument used by a surgeon operating on the patient, for example, patient A 52205, patient B 52210, and/or patient C 52215 located within respective operating rooms as shown in FIG. 11. The potentiator readings received by the local surgical hub/edge device 52225 may be then provided to the machine learning model 52220 located in the local surgical hub/edge device 52225. The machine learning model 52220 may be trained to associate a potentiometer reading with a risk level (e.g., a low risk level). For example, the machine learning model 52220 may determine that the potentiometer readings are unlikely to be linked back to an individual patient, and therefore can be associated with low risk level. Accordingly, a surgical data set that includes potentiometer readings, for example, may be associated with an overall low risk level and may be sent by the local surgical hub/edge device 52225 to an intermediate system hierarchy level or a remote server for further processing.

In an example, one of a surgical data points of a surgical data set may be a cortisol level of a patient. The surgical data point may be generated or calculated based on measurements taken from a wearable that may be worn by the patient during a surgical procedure. For example, the patient may wear a wristwatch which may determine the cortisol level of the patient based on a reading of the sweat produced by the patient. The data point may be generated by the surgical instrument or the local surgical hub/edge device 52225. The local surgical hub/edge device 52225 may determine that the cortisol level may uniquely identify the patient and may assign a risk level (e.g., a high risk level) with the surgical data point. The local surgical hub/edge device 52225 may utilize machine learning model 52220) to assign a risk level to a surgical data point. The machine learning model 52220 may recommend to remove or anonymize the cortisol data point before sending it to a device that may be located outside the protected boundary. The input to the machine learning model may be the surgical data points that may be generated within an operating room, and the output of the machine learning model may be identification of a processing device and/or the system hierarchy level where a surgical data point or a surgical data set containing that surgical data point may be sent for processing.

Figure 12:
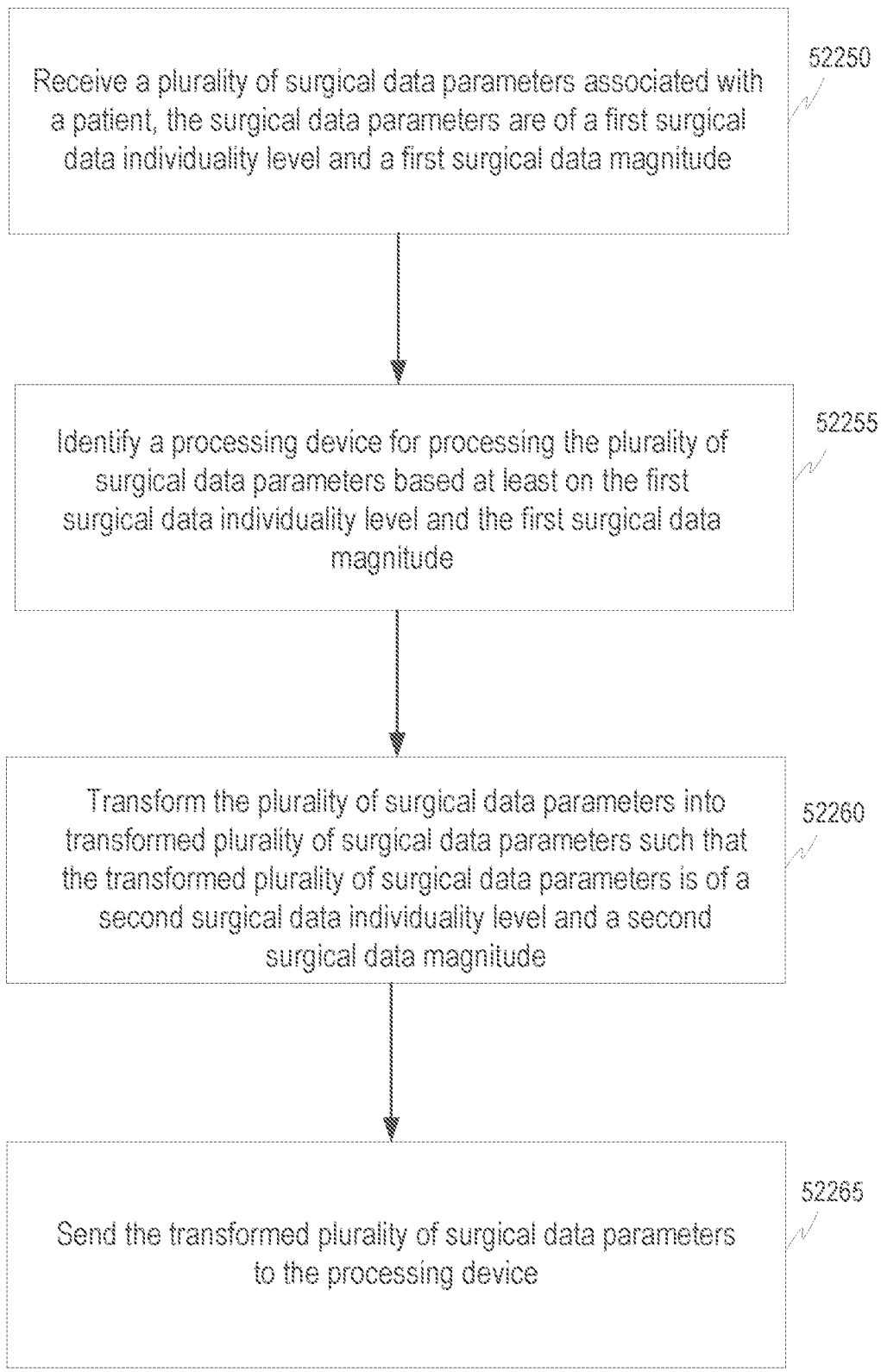
FIG. 12 illustrates an example of transformation of surgical data parameters associated with a patient based on data individuality and the system hierarchy level.

FIG. 12 illustrates an example of transformation of surgical data parameters associated with a patient based on data individuality and the system hierarchy level. At 52250, a surgical device (e.g., a surgical hub) may receive a plurality of surgical data parameters associated with a patient. The plurality of surgical data parameters may be of a first data magnitude (e.g., data size) and of a first data individuality level.

At 52255, the surgical device may identify a processing device for processing the plurality of surgical data parameters. The processing device may be identified based on one or more of: a the first surgical data individuality level, a first surgical data magnitude, a sensitivity to latency in processing the surgical data parameters, the intended use of the first surgical data parameters, characteristics of the first processing server, or a rule set.

At 52260, the surgical device may transform the plurality of surgical data parameters into a transformed plurality of surgical data parameters such that the transformed plurality of surgical data parameters is of a second surgical data individuality level and a second surgical data magnitude. In an example. the second surgical data individuality level may be lower than the first surgical data individuality level. The transformation of the first plurality of surgical data parameters may include anonymization or anonymization of a subset of the plurality of surgical data parameters. The anonymization may include at least one of redaction, randomization, aggregation, setting a range, or averaging.

At 52265, the transformed plurality of surgical data parameters are sent for processing to the processing device identified at 52250

Figure 13:
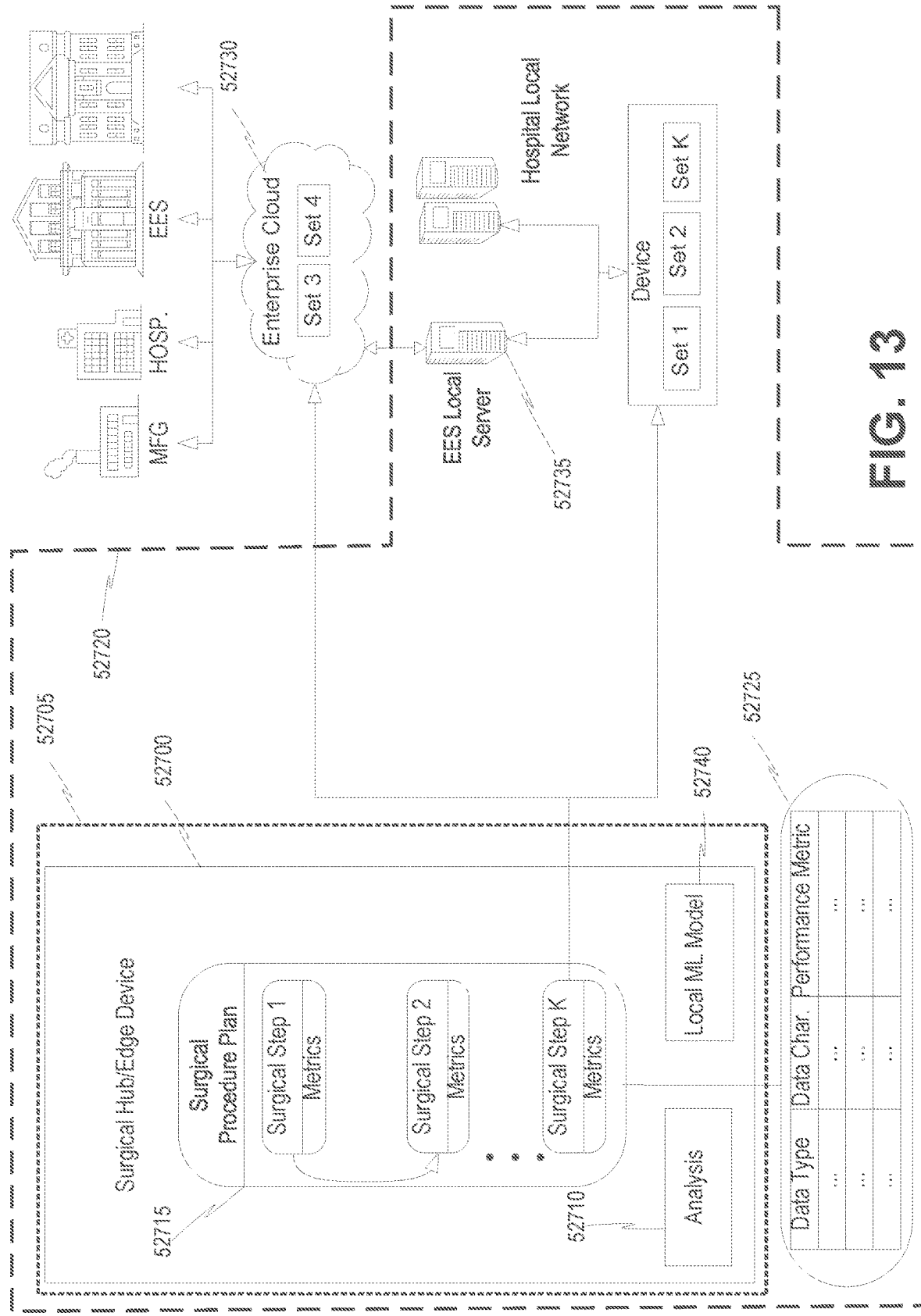
FIG. 13 shows an example of an overview of sending data to multiple system hierarchical levels.

Referring to FIG. 13, an overview of the surgical system may be provided. Surgical instruments may be used in a surgical procedure as part of the surgical system. The surgical hub/edge device may be configured to coordinate information flow to a surgical instrument (e.g., the display of the surgical instrument). For example, the surgical hub/edge device may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Example surgical instruments that are suitable for use with the surgical system are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 13 shows an example of an overview of sending data to multiple system hierarchical levels. The surgical hub/edge device 52700 may be used to perform a surgical procedure on a patient within a surgical operating room 52705. A robotic system may be used in the surgical procedure as a part of the surgical system. For example, the robotic system may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. The robotic hub may be used to process the images of the surgical site for subsequent display to the surgeon through the surgeon's console.

Other types of robotic systems may be readily adapted for use with the surgical system. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, an imaging device may be used in the surgical system and may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device may be configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device and its attachments and components. It will be appreciated that the sterile field may be considered a specified area, such as within a tray or on a sterile towel that is considered free of microorganisms, or the sterile field may be considered an area, immediately around a patient, who has been prepared for a surgical procedure. The sterile field may include the scrubbed team members, who are properly attired, and all furniture and fixtures in the area.

As shown in FIG. 13, a surgical hub/edge device 52700 may be associated with and/or located in a surgical operating room 52705. The operating room(s) 52705 other than a surgical hub may also include one or more surgical instruments and surgical devices. The surgical instruments and surgical devices may be used (e.g., autonomously or manually by the surgeon) to perform the surgery on the patient. For example, the surgical device may be an endocutter. The surgical device may be in communication with the surgical hub/edge device 52700 that may be located within or close to the operating room 52705. The surgical hub/edge device 52700 may instruct the surgical device about information related to the surgery being performed on the patient. In examples, the surgical hub/edge device 52700 may set a settings parameter to a surgical instrument or surgical device by sending a message to the surgical instrument or the surgical device. For example, the surgical hub/edge device 52700 may send the surgical device information indicative of a firing rate for the endocutter to be set at or during a stage of the surgery. The message may be sent to the surgical instrument in response to the surgical instrument sending a request message to the surgical hub/edge device 52700 for the instrument.

Surgical information related to the surgery may be generated. For example, the information may be based on the performance of the surgical instrument. For example, the data may be associated with physical measurement physiological measurements, and/or the like. The measurements are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

Surgical information associated with a surgical procedure being performed in an operating room may be sent to the local surgical hub/edge device 52700. In an example, surgical information associated with measurement(s) taken during a surgical procedure from a surgical display may be sent to the surgical hub/edge device 52700 where it may be further analyzed (e.g., analyzed by the analysis subsystem 52710).

As shown in FIG. 13, a surgical hub/edge device 52700 may track a progression of surgical steps in a surgical procedure and may coordinate functioning of surgical instruments based on such progression as indicated by a surgical procedure plan 52715. The surgical hub/edge device 52700 may determine the surgical steps (e.g., surgical steps 1, 2, through K) associated with the surgical procedure plan 52715. In an example, the surgical procedure tracked by the surgical hub/edge device 52700 may be a colectomy. The surgical procedure plan 52715 for the colectomy may include various surgical steps including, for example, mobilization of the colon. The surgical procedure plan 52715 may be obtained by the surgical hub/edge device or manually entered by a healthcare provider, such as the surgeon. The surgical steps associated with colectomy may be performed by one or more surgical instruments associated with the surgical hub/edge device 52700 and located in the operating room 52705. In an example, each of the surgical instruments may perform respective tasks associated with a surgical step. Surgical instruments may perform the surgical step autonomously. How the surgical instruments operate autonomously is described in greater detail under the heading "METHOD OF CONTROLLING AUTONOMOUS OPERATIONS IN A SURGICAL SYSTEM" in U.S. patent application Ser. No. 17/747,806, filed May 18, 2022, the disclosure of which is herein incorporated by reference in its entirety.

A surgical instrument involved in executing a surgical step may generate surgical data or surgical information associated with a surgical step. The terms data, surgical data, surgical data set, surgical information, surgical metrics set may be used interchangeably herein. Data or surgical data may include the data associated with the surgical hub/edge device 52700, a surgical instrument, data associated with a patient or a healthcare professional, and/or performance of the surgical step, for example as described herein. The surgical information or surgical data may be described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety. The surgical data may include a data type, data characteristics, and a performance metric. A surgical data characteristic may be associated with how sensitive the data (e.g., data form and/or individuality) is (e.g., in other words, what is the risk that the data be traced back to an individual patient). For example, surgical data that is highly sensitive may be likely to be tied back to an individual patient. Such surgical data may not be sent outside of a protected boundary 52720.

Health data is a special category of personal data which is subject to a higher level of protection (see Art. 9 GDPR or the HIPAA Privacy Rule), requiring heightened security considerations due to its cognitive content. Breaches of sensitive personal data can result in the accidental or unlawful destruction, loss, alternation, unauthorized disclosure of, or access to, sensitive data, which can have significant human consequences. For example, the permanent deletion of medical records of a person potentially has significant and long-lasting consequences for the health of said person.

Surgical data processing may be hybridized based on location, for example the location where the data is generated. Hybridization of data may include processing portions of surgical data locally (e.g., on a surgical hub/edge device 52700 or a local network processing), using one or more fog computing devices, and/or using cloud processing. The cloud processing may include analysis of surgical data sets that may be larger than the data sets that are analyzed by, for example, an edge server.

Figure 14A:
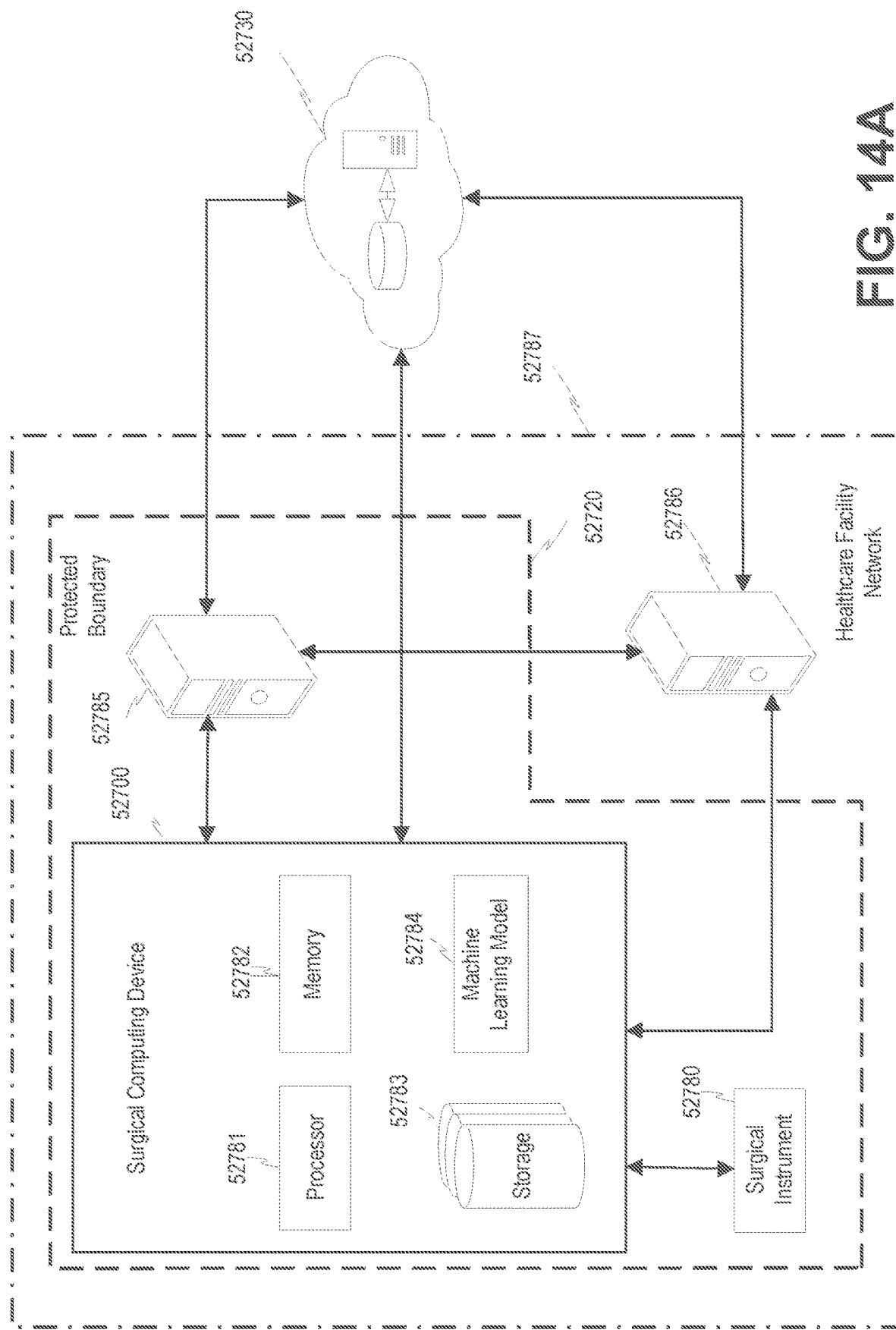
FIG. 14A shows an example of different system hierarchical levels.

Surgical data may be sent (e.g., in surgical data sets) to entities (e.g., entities with processors) located at different system hierarchical levels, as further described with respect to FIG. 13 and FIG. 14A. The systems and/or subsystems at various hierarchical levels may be divided based on one or more of the following: the location (e.g., whether the system or the subsystem is inside or outside the protected boundary 52720), the processing capability (e.g., processing power), the available memory (e.g., size and/or type of the memory), etc. Various hierarchical levels may include: (1) the surgical hub system; (2) the edge or the fog networking system; (3) and/or the cloud enterprise server system. In an example, the surgical hub system and the edge system may be located in the same hierarchical level. The surgical hub/edge device system including the surgical hub/edge device 52700, surgical devices and/or surgical instruments, etc. may be located in an operating room 52705. The edge or the fog networking system may include edge servers. The edge or the fog networking system may include server systems that may be co-located within a healthcare facility and/or distributed within a healthcare facility's network. As illustrated in FIG. 13, the surgical hub/edge device system and the edge or fog networking system may be located within a protected boundary 52720, for example, protected boundary based on the HIPAA rules. The enterprise cloud server system 52730 may include one or more enterprises cloud servers.

The surgical hub/edge device 52700 may determine a processing device in a system hierarchical level that may be suitable for processing the surgical data set or a portion or subblock of the surgical data set. The surgical hub/edge device 52700 may send the surgical data set to the determined processing device. For example, the surgical data set 52725 may be sent locally for processing, for example, to an edge server 52735 that is located within the protected boundary 52720. In an example, the surgical data set 52725 may be sent to an enterprise cloud server 52730 that may be located outside of the protected boundary 52720. In an example, the surgical data set 52725 may be sent to a server located within an intermediate system hierarchical level. For example, the intermediate system hierarchical level may be a location that is within a hospital network but is not within the protected boundary 52720.

The proportion of processing the surgical data at different hierarchical levels may be determined using system aspects, a parameter associated with the surgical data to be processed, and/or a result associated with the surgical data. System aspects, for example, inherent system aspects or the patterns needed may be utilized to determine the location where the surgical data may be processed or sent for processing. The system aspects and/or the patterns may be utilized to determine the extent the surgical data should be processed at different hierarchical levels of a system. For example, a high frequency surgical data set may be modified (e.g., decimated) to send (e.g., only send) a portion (e.g., a useful portion) of the surgical data for processing at different system levels of hierarchy of a system. In an example, the portions of subblocks of the surgical dataset may include calculated impedance spectrum instead of the complete set of voltage and current samples.

In an example, the parameters (e.g., only the parameters) of the algorithms may be transferred back to the main repository. The parameters may be used by ML models 52740 to enhance tissue characterization and performance. The ML models 52740 may be run inside a smart device (e.g., a smart instrument or a smart surgical hub/edge device 52700), an edge computing device, or a fog computing device (not shown) that may be located within the protected boundary 52720 of a healthcare facility. In an example, the processing capability of an edge or a fog computing device may be lower than a cloud-based server or an enterprise server.

In an example, ML models, e.g., light version of a local ML model may be used on a smart surgical hub/edge device 52700 or a fog or edge computing device. The local ML model may be utilized to calculate a smaller number and/or simpler calculations using, for example, devices with lower processor power than the cloud-based server devices. For example, gradient-enhanced kriging surrogate modeling may be utilized to provide a low computational cost mechanism of evaluating processor intensive functions. Gradient-enhanced kriging models may be utilized to reduce the number of function evaluations for the desired accuracy when efficient gradient computation, such as an adjoint method, is available. Such gradient-enhanced kriging models may be run on a smart surgical instrument itself to predict an output. In an example, the gradient-enhanced kriging models may be run on a smart surgical hub/edge device 52700 or a fog computing device.

In an example, a machine learning model and/or a trained machine learning model may be utilized as part of a supervised learning framework. Supervised learning model is described herein in FIG. 8A. The training data (e.g., training examples 802, as illustrated in FIG. 8A) may consist of a set of training examples (e.g., input data mapped to labeled outputs, for example, as shown in FIG. 8A). The training data used in training the local machine learning model 52515 may include data gathered from previous surgical procedures and/or simulated surgical procedures. The training data may include attributes or parameters associated with a patient and/or parameters associated with surgical instrument(s). In an example, the local ML model as an output may provide measurable outcomes associates with a surgical procedure. For example, a ML model may be utilized to detect low risk interpretations including, for example, a prediction that hemostat may be required during a colorectal surgical procedure, prediction of post-operative leaks after a surgical procedure (e.g., colorectal surgical procedure), prediction of post-operative air leaks after a thoracic surgical procedure, etc. These predictions may be made based on various surgical data inputs including, for example whether the patent was irradiated before the surgical procedure and/or whether the patient consumed a certain type of drug. One or more of the attributes associated with a patient may be redacted before sending the surgical data for further processing to an enterprise cloud server location. In an example, the attributes selected for redaction may be performed in a manner to have minimum impact on a measured outcome.

In an example, a condensed parameterization mechanism may be utilized by a system (e.g., a system located in lower hierarchical level hierarchy) to filter out, condense interrelated data, or filter data that may have less significant probabilities of impacting a measured outcome. The lower hierarchical level system or a device located at a lower hierarchical level may perform condensed parameterization of surgical data, for example, before sending it to a higher level for further processing. The condensed parameterization of surgical data may be performed based on one or more of the following: limitations in communication, memory storage, processing resources by one or more higher level systems, etc.

In an example, surgical data collected in a device or a system that is located at a lower hierarchical level may be reduced before transferring it to the next hierarchical level (e.g., higher). For example, as illustrated in FIG. 14A, surgical data collected at the surgical instrument 52780 or processed at the surgical computing device 52700 or an edge server 52785 located within the protected boundary 52720 may be reduced before sending it to next hierarchical level (e.g., an enterprise cloud server 52730 located outside the protected boundary 52720).

The locally compiled parameterization, signal processing, and/or data reduction may be performed at a lower (e.g., lowest) branch of a hierarchical tree (e.g., the collection device or a smart instrument). The lower branch may be a smart surgical instrument 52780 or the surgical computing device 52700. The selective data parameterization, signal processing, and/or surgical data reduction may be performed based on at least one of the following: the processing limitations of the next hierarchical level, importance of surgical data, surgical data that may have minimal or no effect on a measured outcome or result, risk or severity of the surgical data or its implications, time relative to an event (e.g., failure, technical irregularity, communication issue, etc.).

In an example, a surgical instrument 52780 or a surgical subsystem that is located at a lower level in the computational hierarchy may perform decimation of data before transferring the surgical data to a device or a subsystem that is located at a next or higher level in the computational hierarchy, for example, the surgical computing device 52700 or an edge server 52785. In an example, data decimation may include removal of every tenth data point in the surgical data set. In the case of signal processing, decimation by a factor (e.g., a factor of 10) may include saving/keeping every tenth sample. Specialized, purpose-built and/or customized processing units (e.g., an application specific integrated circuit (ASIC) based processing unit or a reduced instruction-set computing (RISC) based processing unit) may be used in such devices (e.g., an end effector, shaft or handle of the instrument) to decimate the surgical data and/or process/condition signals so that the output from such computing devices (e.g., only the output from such devices)

may be handled by another computing device that is located at a higher level in the computational hierarchy.

A mid-level device or a system may reduce and/or limit transferred data up the computational hierarchical levels based on the communication parameters, network conditions to the next node in the computational hierarchy (e.g., the next higher node in computational hierarchical levels), and/or processing capabilities of the system located higher in the computational hierarchy. For example, the surgical computing device 52700 may reduce and/or limit transferred surgical data to the enterprise cloud server 52730) based on the link condition between the surgical computing device 52700 and the enterprise cloud server 52730. The reduction and/or limitation of data at a mid-level computational hierarchical system may provide combined parameters or parameter data by eliminating or limiting the surgical data or a portion of the surgical data that may have a minimal or no impact on the measured outcome. The reduction and/or limitation of data may be performed based on the directionality of decomposition of the data with leading trending but inconclusive results. This may result in finding high signal patterns or relationships among data (e.g., by sacrificing more detailed interactions) in order to maximize benefit of cost, time, bandwidth, and/or processing resources.

In an example, edge computing processes running on an edge device 52785 or a fog computing device residing in healthcare facility's network 52720 may be utilized for providing edge processing of data locally, for example, using artificial intelligence. In an example, federated learning may be utilized to enable collaborative training of machine learning models on the edge device. Edge computing may process data away from centralized storage or a cloud server 52730 and may keep information on the local parts of the network edge devices 52785. Surgical data sent to an edge device 52785, or a fog computing device may be processed directly on the device, for example, without sending it to a centralized enterprise cloud server 52730. Processing of surgical data on an edge server device 52785 or a fog computing device may mean minimal or no delays in data processing. The data may be stored on the edge of a network, for example, an Internet of Things (IOT) network and may be processed immediately.

In an example, an edge device 52785 or a fog computing device may be utilized for performing real-time data analysis on data that the edge device 52785 or the fog computing device may receive from a smart device or a smart surgical instrument that is located lower in computational hierarchy or a device or a system that is located higher in computational hierarchy than the edge device 52785 or the fog computing device. The edge device 52785 or the fog computing device may be utilized to process substantial amounts of data, it may receive form a smart computing device or a smart surgical instrument that is located lower in computational hierarchy or a device or a system that is located higher in computational hierarchy than the edge device 52785 or the fog computing device. The edge device 52785 or the fog computing device may have capability of processing data immediately.

In an example, the network congestion between a surgical computing device 52700 or a surgical instrument 52780 that is located lower in a computational hierarchy than an enterprise server 52730 may be minimal. Such an edge device 52785 or a fog computing device may be utilized (e.g., utilized first) to process data locally (e.g., at the edge device 52785 or the fog computing device) and send the processed data to the main storage (e.g., storage at the enterprise server 52730). In an example, various prioritized data types may be sent for processing to the edge device or the fog computing device in order, for example, based on a priority value associated with each of the data types.

In an example, a device or a surgical instrument 52780 (e.g., with limited resources and/or higher down time) that is located lower in the computational hierarchy than the edge device 52785 or the fog computing device may utilize the edge device 52785 or the fog device to pre-process or completely process its data. The edge device 52785 or the fog computing device may send results (e.g., results in simpler conclusion form) back to the surgical device or surgical instrument 52780 that is located lower in the computational hierarchy than the edge device 52785 or the fog computational device. The edge device 52785 or the fog computational device may send the results through a link that may be experiencing network congestion.

Utilizing the edge device 52785 or the fog computational device for data management and/or data processing may result in reduced operating costs. Data management takes less time and computing power because the operation may have a single destination, for example, instead of circling from the center to local drives.

A device, for example, a smart surgical hub/edge device 52700 may consider one or more of the following to determine where to send surgical data for processing and/or to what extent to process the surgical data: the surgical data type, portion of surgical data to be processed, surgical data characteristics (e.g., surgical data form, surgical data magnitude, etc.), the performance metric, the processor's capabilities, network characteristics (e.g., congestion in the network), etc., as described herein. For example, one of the surgical data characteristics associated with a surgical data set 52725 may be that the surgical data set 52725 includes surgical data that is highly likely to be traced back to an individual patient. In such a case, the surgical data may be processed locally within the protected boundary 52720) and may not be sent to the enterprise cloud server 52730.

In an example, a smart surgical hub/edge device 52700, for example, based on a processor's and/or a processor device's capabilities, may determine that a surgical data set 52725 is to be processed at an enterprise cloud server 52730 that is located outside the protected boundary 52720. If the surgical data set 52725 includes surgical data that is highly sensitive, the surgical hub/edge device 52700 may anonymize the surgical data set 52725 or a portion of the surgical data set 52725, for example, using one or more of the anonymization mechanisms (e.g., redaction, randomization, aggregation, etc.). The surgical data set 52725 or a portion of the surgical data set 52725 may be anonymized in order to reduce the likelihood of the surgical data set being traced back to a patient, as described herein.

A mix of a centralized data storage system and cloud computing may be provided. Computing may be performed at local networks (e.g., although servers themselves may be decentralized). In such a case, the surgical data may be accessed offline, for example, because some portions of the surgical data may also be stored locally. Fog computing and cloud computing may be provided. Low latency may be associated with the fog network, where large volumes of data may be processed with little-to-no delay. Because a significant amount of data may be stored locally, the computing may be performed faster. Better data control may be associated with cloud computing. In cloud computing, third-party servers may be fully disconnected from local networks, leaving little to no control over data. In fog computing, users may manage surgical information locally and rely on their security measures. A flexible storage system may be associated with fog computing. For example, fog computing may not use (e.g., require) constant online access. The data may be stored locally or pulled up from local drives. The storage may combine online and offline access. Connecting centralized and decentralized storage may be described herein. Fog computing may build a bridge between local drives and third-party cloud services, allowing a smooth transition to fully decentralized data storage.

Referring to FIG. 13, the location where a surgical data set 52725 is sent for processing and/or the extent of surgical data set 52725 to be sent for processing may be determined based on a metric (e.g., performance metric) associated with the surgical data set 52725, such as latency, network congestion, etc. In an example, a system may weigh urgency of the need of the surgical data results against the magnitude of the surgical data and compare it with the capabilities within the system's local protected network to determine where and how the data may be sent for processing. For example, a surgical data set 52725 associated with a low latency metric may indicate its timeliness or criticality. Such surgical data may be sent for processing with the least latency (e.g., in order to perform the next surgical step in time). In such a case, the surgical hub/edge device 52700) may determine to send the surgical data locally to a processor or processing device that may process the surgical data in timely fashion with low latency (e.g., rather than sending the data to enterprise cloud server 52730). For example, the surgical data set 52725 may be sent to an edge network comprising an edge device 52735 or a fog computing device (not shown in the figure). The edge device 52735 or the fog computing device may be located within a protected boundary 52720. The edge device may, therefore, process large volumes of data within an acceptable time interval. In examples, if the surgical data set 52725 is associated with a high latency performance metric, the server hub 52700 may send the surgical data for processing to an enterprise cloud server 52730 that is located outside the protected boundary 52720. The surgical data or a portion of the surgical data may be anonymized before being sent to the enterprise cloud server for processing, as described herein.

In examples, the edge device 52275 after performing analysis on the surgical data may further anonymize the surgical data (e.g., as described in FIG. 10) send it for further comprehensive processing to the enterprise server 52730 that is located outside the protected boundary 52720.

In an example, results and/or conclusions associated with surgical data obtained within a local healthcare facility network may be sent to an enterprise cloud server for further processing. A portion of the surgical data may be sent to the enterprise cloud server in clear and/or redacted form, as described herein. The results and/or conclusions associated with the surgical data, for example, with other portions of the surgical data may be utilized to determine relationships with one or more measured outcomes. For example, in prolonged air leak (PAL) a section of a lung is removed. After the surgical procedure, there may be an air leak that may stop in a few days. A lung collapse may occur if the chest cavity is filled up. PAL may depend on one or more of the following pieces of surgical data: the transection device that was used during lobectomy, location the removed lobe, artifact of the patient (e.g., state and/or stage of the disease that calcified the lung, whether the patient was exposed to irradiated or experienced chemo therapy before the surgical procedure, and/or whether the patient was taking any medication, which may cause air leaks or enhance healing), kind of surgical procedure and/or risk associated with the surgical procedure (e.g., whether a small or a big piece of lung was removed). When the surgical data associated with a thoracic surgical procedure, for example, is sent from a device within the protected boundary to the enterprise cloud server, a portion of the surgical data associated with the patient may be anonymized before sending it to the enterprise cloud server. The portion of surgical data may include, for example, stage of the disease of the calcified lung, whether the patient was irradiated or experienced chemotherapy before the surgical procedure, and/or whether the patient was taking any medication. Other portions of the surgical data may be sent in non-anonymized form.

In an example, a measured outcome may be characterization of a disease state. Such a measured outcome may be determined by eliminating a portion of personal data associated with a patient. The selection of the data portion to be eliminated or redacted may be based on the relevance of the data portion in determining the measured outcome.

Variance analysis may be conducted, for example, to compare, an actual outcome of a surgical procedure with an expected or standard outcome. The differences may be investigated, for example, in order to address the performance inefficiencies. In an example, variance analysis may be conducted using a decision model. Variances may be identified that are statistically significant and require further investigation.

In an example, surgical data associated with a surgical procedure may be transferred (e.g., automatically transferred from a surgical hub/edge device 52700 to an enterprise cloud server 52730) (e.g., an enterprise server). The enterprise server may collect surgical data from various healthcare facilities of diverse geographical locations. In an example, the surgical hub/edge device 52700 may send surgical data periodically to an enterprise cloud server 52730. In an example, the surgical data may be sent aperioidcally, for example, based on the surgical hub/edge device 52700 receiving a request from the enterprise cloud server 52730.

In an example, a surgical hub/edge device 52700 may determine the system hierarchical level where the surgical data may be sent for processing. The system hierarchical level where the surgical data may be sent for processing may be determined by using a machine learning model 52740) (e.g., which may be located in the surgical hub/edge device 52700). In an example, a machine learning model and/or a trained machine learning model may be utilized as part of a supervised learning framework, for example, as described herein in FIG. 8A. The training data (e.g., training examples 802, as illustrated in FIG. 8A) may include a set of training examples (e.g., input data mapped to labeled outputs, for example, as shown in FIG. 8A). The training data used in training the local machine learning model 52515 may include data type associated with surgical data, characteristics and at least one of performance metrics, processor capabilities, etc. associated with a particular target processing device where the surgical data may be sent for processing. The output may include a hierarchical level that may be suitable for processing the surgical data. The output may also include identification of a server and/or location of the server where the surgical data may be sent for processing.

As described with respect to FIG. 13 and FIG. 14A, the surgical data set 52725 may be divided into data chunks portions or subblocks and sent to different levels of the system hierarchy. Surgical data chunks or surgical data portions or surgical data subblocks may be used interchangeably herein. The surgical data subblocks may be sent to various processing devices in parallel at the same time interval or in series at different time intervals. In an example, a machine learning model 52740 may be used to predict how the surgical data set 52725 may be divided into data subblocks. The machine learning model 52740 may also be used to predict where and when the divided data subblocks (e.g., each of the data subblocks) may be sent for processing. In an example, a machine learning model 52740 may predict how to divide the surgical data set 52725 in a way that results in a data subblocks without highly sensitive data. The machine learning model 52740 may predict where to send each of the data subblocks for further processing. For example, the machine learning model 52740 may predict that a first data subblock comprising non-sensitive data may be sent to enterprise cloud server 52730 for processing. The machine learning model 52740 may also predict that data subblock that comprises highly sensitive data may be sent locally to an edge server that is located within the protected boundary 52720.

The surgical hub/edge device 52700 may consider a potential benefit of sending the data to a particular system hierarchical level when determining where to send it. For example, the surgical hub 52700 may assess that a surgical data set 52725 may benefit from being processed at an enterprise cloud server 52730 rather than locally (e.g., based on the enterprise cloud server 52730 having access to a more diverse data pool than a local edge server). The surgical hub/edge device 52700 may determine to send the surgical data set 52725 to the enterprise cloud server 52730. Accordingly, surgical hub/edge device 52705 may send the surgical data set 52725 to the enterprise cloud server 52730 or a local edge server.

In an example, the surgical hub/edge device 52700 may consider the capabilities of the processors located at the different system hierarchical levels when determining where to send the surgical data set 52725. For example, the enterprise cloud server 52730 may have a capability of having higher processing power as compared to processing power of a local surgical hub or even an edge server. A surgical data set 52725 may have high data magnitude (e.g., included in the data characteristics). In such a case, surgical hub/edge device 52700 may determine that the surgical data set 52725 is to be processed at the enterprise cloud server 52730, which has a more power. In examples, the surgical data set 52725 may be of smaller data magnitude. In such a case, the surgical hub/edge device 52700 may send the surgical data set 52725 locally (e.g., to one of the local servers with less processing power than the enterprise cloud server).

In an example, the surgical hub/edge device 52700 (e.g., via the machine learning model 52740) may consider surgical data granularity (e.g., included in the data characteristics) when determining where to send the surgical data set 52725. Surgical data granularity may be associated with a measure of comprehensiveness or a degree of the surgical data set 52725 (e.g., all of the relevant data points versus a subset of the relevant data points). The surgical hub/edge device 52700 may determine that for a particular surgical data set 52725, data granularity may be given more importance than data diversity. In such a case, the surgical hub/edge device 52700 may send the surgical data or a portion of the surgical data to a local server for processing (e.g., if none of the data points of the surgical data set need to be anonymized such as redacted, resulting in the surgical data set 52725 having higher data granularity). In examples, the surgical hub/edge device 52700 may determine that for a particular surgical data set 52725, data diversity may be give higher importance than data granularity. In such a case, the surgical hub/edge device 52700 may send the surgical data set 52725 to an enterprise cloud server 52730 located outside of the protected boundary 52720 (e.g., where the data granularity (e.g., the amount of the data that may be included with the request) is lower and data diversity is higher than that of the surgical hub/local edge device).

As illustrated in FIG. 13, the surgical hub/edge device 52700 may send surgical data sets three and four to the enterprise cloud server 52730. These surgical data sets may be less granular than surgical data sets one, two and/or K. The surgical hub/edge device 52700 may send data sets one, two and/or K to a local server 52735 located within the protected boundary 52720.

A feedback mechanism may be used to evaluate the machine learning model's predictions or decision-making. For example, a score may be generated based on a surgical instrument's performance, for example, when the machine learning model selects a local server 52735 over an enterprise cloud server 52730 for data processing. The score may be used to improve the machine learning model's predictions or decision making when it determines where to send the surgical data sets 52735 for processing.

As described herein, capabilities of the processors (e.g., each of the processors) may be considered by the surgical hub/edge device 52700) when determining where to send the surgical data sets 52725 for processing. Data individuality level may also considered by the surgical hub/edge device 52700, as described herein. For example, the surgical hub/edge device 52700 may be aware of the processors' capabilities (e.g., each of the processors' capabilities). The surgical hub/edge device 52700 may be configured with capabilities, for example, as part of a surgical procedure plan 52715 or prior to initiating a surgical procedure. For example, the surgical hub/edge device 52700 may determine that the processing power of a remote cloud server 52730 is more than the processing power of a surgical hub 52700 or a local edge server 52735. The surgical hub/edge device 52700 may also consider the data individuality level associated with the device where the surgical data 52725 may be sent for processing. These factors may be used as input by the machine learning model 52740 when determining where to send the surgical data set 52725 for processing. In an example, the capabilities of various devices (e.g., an edge server located inside a protected boundary, an edge server located within a healthcare facility's network, or an enterprise cloud server located centrally at a global or a regional level) may be determined by exchanging discovery request/response messages.

The network traffic may be considered when determining where to send the surgical data set 52725. For example, the surgical hub/edge device 52700 may send a test signal through the network to each of the processors that are a part of servers or devices located at different system hierarchical levels. The test signal may be utilized for requesting an acknowledgement message (e.g., an ACK message). Based on the latency of the ACK message, the surgical hub/edge device 52700) may determine and assign a network quality score to each of the processing devices located across various system hierarchical levels. The network quality score may then be utilized by the machine learning model 52740 in predicting where to send the surgical data set for processing.

In an example, a simulation may be generated by the surgical hub/edge device 52700. The simulation may be used (e.g., in combination with the machine learning model 52740) to determine the device or the processor associated with a device where surgical data set 52725 may be sent for processing. A simulation may be used to determine the threshold (e.g., an ideal threshold). Simulation framework may be described in "Method for Surgical Simulation" in U.S. patent application Ser. No. 17/332,593, filed May 27, 2021, the disclosure of which is herein incorporated by reference in its entirety. The simulation may output a score associated with sending the data to each of the processing servers. The surgical hub/edge device 52700, based on the simulations, may choose the processing device for surgical data processing in a manner to maximize the score. The simulations with a score less than the determined threshold may be excluded from considering the simulation as a candidate for choosing a processing device.

In an example, a surgical data set's property to be controlled may be considered by the machine learning model 52740 when determining where to send the surgical data for processing. For example, if the surgical data set 52725 is sent to an enterprise cloud server 52730, the surgical hub/edge device 52700 may have little control or no control of managing the data. The surgical hub/edge device 52700 may be able to manage and control the surgical data, for example, if the surgical data set 52725 is sent to a local server 52735.

Figure 14B:
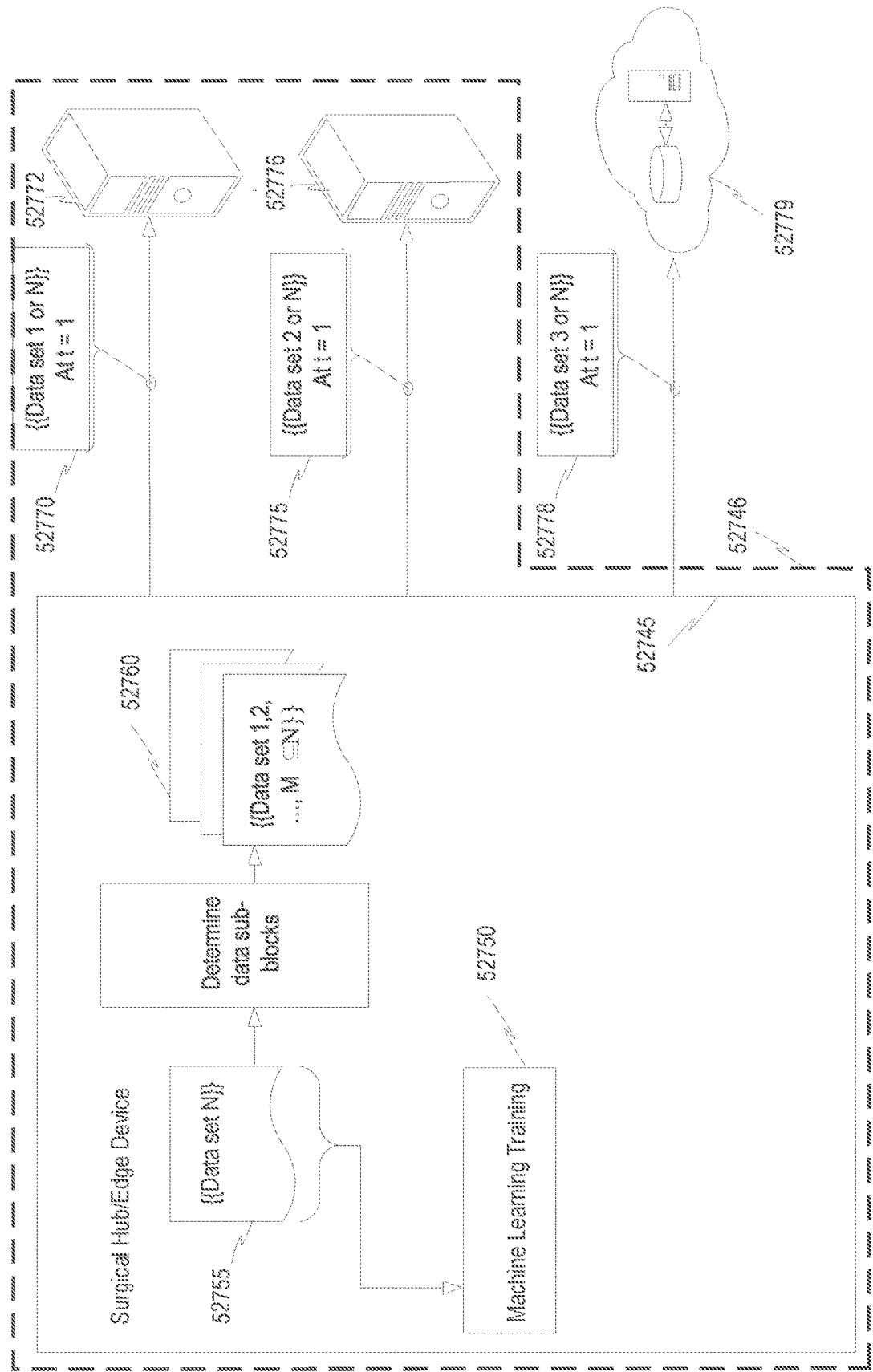
FIG. 14B shows an example of dividing the surgical data sets and sending the divided surgical data sets to different system hierarchical levels.

FIG. 14B shows an example of a surgical hub/edge device 52745 dividing surgical data sets 52755 in various surgical data subsets and sending the divided surgical data subsets to different system hierarchical levels. In an example, a machine learning model 52750 may be used to adjust the surgical data set 52755 before sending it for processing. For example, the surgical hub/edge device 52745 may determine that a given surgical dataset 52755, such as surgical dataset N, should be adjusted and/or manipulated and split into data subblocks 52760) (e.g., as illustrated in FIG. 14B) before sending it out for processing. The surgical hub/edge device 52745 may run a simulation with different combinations of dividing the surgical dataset 52755 into data subblocks. The surgical hub/edge device 52745 may then obtain how the surgical data set 52755 may be split and determine how the surgical data sets 52755 may be divided.

In an example, the machine learning model 52750 may be trained to take a surgical data set 52755 as an input and a combination of multiple data sub blocks 52760 as an output. In an example, a machine learning model and/or a trained machine learning model may be utilized as part of a supervised learning framework, for example, as described herein in FIG. 8A. The training data (e.g., training examples 802, as illustrated in FIG. 8A) may include a set of training examples (e.g., input data mapped to labeled outputs, for example, as shown in FIG. 8A). The training data used in training the local machine learning model 52515 may include surgical dataset(s). The output may include data subblocks, and an indication of where, when, and to what extent the data subblocks should be processed or sent for processing.

In an example, the machine learning model 52750 may predict and indicate that surgical data set N 52755 is to be divided into surgical data subsets one, two, through M (e.g., wherein each of the surgical data sets may include a number of the data points originally in dataset N). As illustrated in FIG. 14B, the machine learning model 52750 may be utilized to indicate that at time T equal to 1, the surgical data subset one 52770 and the surgical data subset two 52775 are to be processed locally, while the surgical data subset three 52778 is to be sent remotely to an enterprise cloud server.

In an example, the processing of the surgical data subset one 52770, the surgical data subset two 52775, and the surgical data subset three 52778 may occur in parallel. In such a case, the surgical data subsets may be sent for processing to various processors or processing devices in parallel, e.g., at the same time interval.

In an example, a machine learning model may be used to predict sending various surgical data subsets or subblocks (e.g., subblocks associated with a surgical dataset) to the same processor such as a local processor. The machine learning model may also predict the time intervals (e.g., different time intervals) at which the data subsets or subblocks may be processed by the processors or the processing devices.

Referring to FIG. 14B, the surgical hub/edge device 52745 may determine that at least because of the sensitivity associated with the surgical data subsets 52770 and 52775, they may not be sent to an enterprise cloud server for processing. In such a case, the surgical hub/edge device 52745 (e.g., using the machine learning model 52750) after splitting or dividing the surgical data sets 52755 into multiple surgical data subsets or subblocks may be processed locally either by the surgical hub/edge device 52745 or sent for processing to the edge servers 52772 and 52776, or at least one fog computing device (not shown in FIG. 14B). The surgical hub/edge device 52745, edge servers 52772 and 52776, and the fog computing device(s) may be located within the protected boundary 52746. In an example, the two surgical data subsets or subblocks may be sent for processing to the same edge server or a fog computing device that is located within the protected boundary 52746.

In an example, the surgical hub/edge device 52745, based at least on a performance metric associated with the surgical data subset or a surgical data subblock, may determine the manner in which the surgical data subblocks may be processed. For example, surgical data subset one 52770 may be associated with a low latency and surgical data subset three 52778 may be associated with a high latency. In such a case, surgical data subset one 52770 may be sent to a local server capable of processing the data with low latency, while surgical data subset three 52778 may be sent to an enterprise cloud server 52779.

In an example, location (e.g., level in computational hierarchy) of a device or a processor where surgical data may be sent for processing may be determined based on various surgical data characteristics, for example, intended utilization of results associated with surgical data, or the type of metadata associated with the surgical data. For example, a local device (e.g., a surgical hub/edge device 52745 or a smart surgical instrument) may be utilized for interactive or repetitive accessing, updating, or aggregation surgical data processing. In such a case, the surgical data may be added or extracted repeatedly. Accordingly, the conclusions or results may be updated (e.g., updated periodically). The conclusions or results may be updated, for example, after each surgical data addition or extraction. The portion of the surgical data processing algorithm that processes such repeated operations may reside on a device or a smart surgical instrument that is located within a protected boundary or a healthcare facility's premises or network.

In an example, surgical hub/edge device 52745 may use metadata or portions of metadata associated with surgical data to determine the location where the surgical data may be sent for processing, stored, and/or utilized. Metadata or a portion of metadata may indicate the network where the data was collected or stored (e.g., in a hospital network level micro-cloud network.) The network may retain control of the confidential patient information. Patient specific information may be utilized to train a new control algorithm. The training of a control algorithm may be conducted from a base surgical data set (e.g., acting as a seed surgical data set) or using data that is collected in the hospital network.

In an example, a metadata or a portion of metadata may include sensitivity of surgical data, for example, a confidentiality flag or an identifier of the surgical data designating the confidentiality level of the data. Such metadata or portion of metadata may be used to determine or control the level of surgical data processing.

In an example, surgical hub/edge device 52745 may use the amount of redaction of surgical data as a factor to control the level within a system where certain type of analysis of the surgical data may be performed. For example, low level analyses that may benefit from all the interrelated but identifiable personal surgical data may be performed within a protected boundary 52746 of a healthcare providers network. In an example, high level analyses that may performed with a portion of underlying surgical data anonymized may be performed by an enterprise cloud server 52779 that is located outside the protected boundary 52746.

In an example, higher level aggregations of regional or world-wide surgical procedure outcomes and/or surgical procedure step data may be performed on enterprise cloud servers. The enterprise cloud servers may be located outside the protected healthcare facility's network. Such enterprise cloud servers may have capability of processing large amounts of data. The data that may be processed at the enterprise cloud servers may be of type where personal biomarker data may not be needed. The data to be processed may be redacted before transferring it out from the protected network to other storage locations.

In an example, one or more of resources available in a processing device, system or a network, risk associated with surgical data, and a need for processing surgical data within a protected network may be utilized to determine priority, processing depth, and/or storage of the data and/or algorithmic results.

Figure 15:
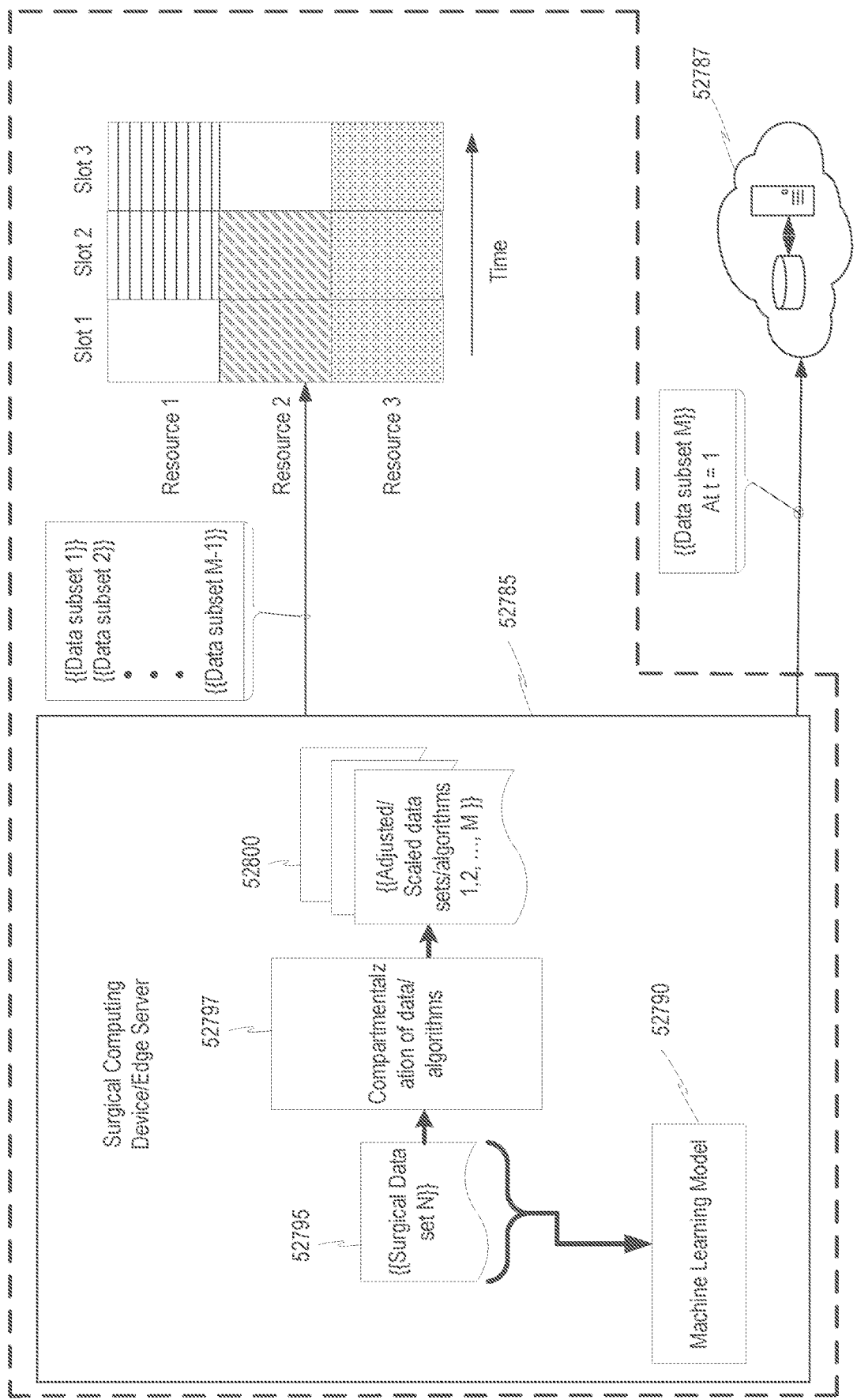
FIG. 15 illustrates compartmentalization of data and/or algorithms.

As described with respect to FIG. 15, a priority may be assigned to the surgical data subsets or subblocks (e.g., each of the surgical data subblocks) to determine the time and/or the resource that may be used for processing a particular surgical data subset or a subblock. The availability of at least one resources may be used in determining the resource that may be a particular data subset or a subblock of a particular priority level, as described herein.

FIG. 15 illustrates compartmentalization of surgical data and/or algorithms. Machine learning (ML) model 52790 may be utilized to process surgical data at local devices/systems and/or cloud servers. Compartmentalization (e.g., selective compartmentalization) of ML algorithm processing of local surgical data may be performed.

In an example, adjustment/scaling of the breadth, depth, and/or reduction of local surgical data may be performed on a local surgical computing device (e.g., a surgical hub) or an edge server based on the local available resource-time dependency relationship. Adjustments/scaling may include adjustment/scaling of the one or more of the following: amount of data or the variables that may be processed, the frequency or accuracy level of the surgical data, the algorithm type, the tolerable error of the algorithm, stacking levels of the algorithm, or validation (e.g., verification and/or checking) of a measured outcome or result.

As illustrated in FIG. 15, various resources of a processing device (e.g., a surgical hub or an edge server device) may have varied availability. For example, Resources 1 and 2 may be available for only two time out of three time slots (e.g., time slot 2 and 3 for Resource 1 and time slots 1 and 2 for Resource 2), and Resource 3 may be available in all the three slots. In such a case, compartmentalization and scaling may be performed in a such a way that the breadth and/or depth of surgical data subsets or subblocks to be processed by Resources 1 and 2 may the ones that need lesser resources (e.g., lesser amount of data, lesser number of variables, etc.) than the surgical data subset or subblock to be processed by Resource 3.

In an example, as illustrated in FIG. 15, local surgical data (e.g., surgical data set 52795) may be adjusted and/or scaled 52800 based on at least one of the following: timeliness of the needed result, processing and memory available, network bandwidth or communication parameters (e.g., throughput, latency, etc.), risk level of functioning without the answer, importance of the data or task, availability of other surgical data to be used in substitution. In an example, if a surgical data set 52795 to be analyzed is associated with timeliness of the needed result, the compartmentalization may be performed in a way that the time sensitive surgical data is scaled to be processed by Resources 2 and 3 (e.g., with all three time slots available for processing) and not Resource 1 (with the first time slot not being available for processing immediate or in slot 1). In an example, scaling of the breadth, depth, and/or reduction of local surgical data may be performed to balance the level of results achieved within a time interval and the resources that may be needed.

In an example, as illustrated in FIG. 15, surgical data or ML algorithms may be compartmentalized or clustered 52927. ML algorithms may be compartmentalized into smaller portions, for example, based on magnitude or level of processing. In an example, complexity of an ML algorithm may be determined based on the available local computing resource levels. A ML algorithm may be utilized between a cloud and edge processing networks. An algorithm pre-processing component may use a system and its resources on which it resides as a means for determining the following: the factors to be considered for diversity of a surgical dataset, a level of compartmentalization of surgical data, and/or analyses of surgical data.

ML algorithms used for analyzing surgical data may be scaled based on the computing resources (e.g., computational power, size of memory of the computing resource) associated with the surgical system 52785, on which the ML algorithm is running, the competing processing needs associated with various processes running on the surgical system 52785, and/or the breadth of the surgical dataset 52795. The computing resources associated with the surgical system, the competing processing needs by various processes running on the system, and/or the breadth of the surgical dataset may vary based on time, as illustrated in FIG. 15.

In an example, in a surgical computing device (e.g., a surgical hub) where the computing resources are being utilized for processing and/or analyzing surgical data received from various surgical devices (e.g., including video feeds from various cameras in an operating theater), the surgical device may scale an ML algorithm based on the level of the computing resources available (e.g., available during a time slot).

In an example, in a surgical computing device where availability of the computing resources of the surgical computing device are being utilized for processing surgical data received from various surgical devices may vary with time. The scaling of the ML algorithm may change dynamically (e.g., change dynamically with time) based on the resources available on the surgical computing device where the ML algorithm resides and/or us running.

As illustrated in FIG. 15, in time slot 1, only computing resource 1 and computing resource 2 may be available to be utilized by a ML algorithm, whereas in time slot 2, all the three computing resources 1, 2, and 3 may be available. only for time slots. Based on the availability of computing resources, the surgical device may scale the ML algorithm accordingly. For example, in time slot 1, the ML algorithm may be scaled down (e.g., simplified by ignoring, removing, or combining certain surgical data aspects). This may be done to accommodate the non-availability of computing resource 1, which, for example, may be processing critical piece of surgical data. And, as an example, in time slot 2 with all the three resources being available, the ML algorithm may be scaled up (e.g., by using a more comprehensive surgical dataset and/or performing more complex and comprehensive analyses of surgical dataset).

As described herein, various types of ML algorithms may include supervised algorithms, unsupervised learning algorithms, semi-supervised learning algorithms, reinforcement learning algorithms, etc. Some of the specific types of ML algorithms may include a linear regression, a logistic regression, a decision tree, an SVM algorithm, a Naive Bayes algorithm, an KNN algorithm, a K-means, etc. A respective algorithm complexity level may be associated with each of the ML algorithms. For example, the KNN algorithm may be computationally more complex and, therefore, may have higher algorithm complexity level than the decision tree algorithm.

An ML algorithm complexity level may be associated with the computing resources available. In an example, an ML algorithm of higher computational complexity may be utilized on an edge processing device, or a cloud-based enterprise server with higher computational/processing power and/or memory resources. In another example, an ML algorithm of lower computational complexity may be utilized on a device (e.g., a surgical hub) with lower computational/processing power and/or memory resources.

One or more of the scaling of ML algorithm complexity, the ML algorithm method or processing method applied, and/or the magnitude of the dataset on which the ML algorithm is applied may be determined based on the resources (e.g., computational resources, network resources, etc.) that are available on a surgical system or a surgical computing device, where the ML algorithm may reside and/or one or more attributes of the dataset. The attributes of the dataset may include size of the dataset, complexity of the dataset, depth at which the dataset may be processed, etc.

In an example, an ML algorithm may be compartmentalized into various parts that may be processed on an edge processing device (e.g., and edge processing device within a protected network) and a cloud-based enterprise server (e.g., an enterprise server located outside the protected network). In an example, an algorithm on a computing device (e.g., a pre-processing component of an algorithm) may consider at least the resources associated with the computing device to determine the factors that may be used to obtain magnitude of a dataset that may be analyzed by an ML algorithm. The resources associated with the computing device may include computational/processing power and/or memory resources.

In an example, ML algorithm scaling on a surgical computing system or a surgical computing device may be based on at least one of: the total amount of the surgical data to be analyzed, the depth at which the computing system compiles the surgical data, the serialization of the different processing stages (e.g., which may provide an indication of how long it may take to process the surgical data), or the simplicity of the surgical data or surgical data compilation. The scaling may ignore surgical data aspects, remove or combine categories, or aggregate datasets before removing individual paired comparisons.

In an example, scaling of an ML algorithm may result in simplifying the analysis to be performed on a surgical data. The simplification of the analysis may be performed, for example, by excluding certain surgical data aspects, or anonymizing, removing, or combining certain surgical data categories.

In an example, scaling of local analyses may be performed. As illustrated in FIG. 15, additional processing of surgical data or a surgical data subset or subblock (e.g., data subset M) may be performed on one or more enterprise cloud servers 52787. The enterprise cloud servers 52787 may be co-located or geographically separated. In another example, additional surgical data processing may be performed later in time or in combination with the current surgical data processing.

A device or a system may be configured to prioritize local sub-processing. The local sub-processing may process the part of the surgical data that may be personalized data. The non-personalized portion of surgical data may be processed on remote systems or servers. The non-personalized portion of surgical data may be processed simultaneously with local processing of the personalized portion of surgical data or in sequence.

In an example, a device or a system (e.g., a system located within a healthcare facility) may scale the analyses associated with time dependent aspects of the surgical data that may require immediate returned results within a surgical procedure. The surgical device may perform a more complete or thorough processing of the complete surgical dataset 52795 offline to the procedure. The offline processing may be performed by the device or the system or by a remote cloud-based server or service.

In an example, dynamic reallocation of ML compartments may be performed. For example, in case of a disconnected device or a disconnected element in the computing chain dynamic, reallocation of ML compartments may occur based on reallocation of processing resources. For example, if a communication channel is disrupted due to a failure in the chain (e.g., power interruption, disconnected or damaged instrument or cable during surgery or other hardware/software failure), one of the other surgical computing devices or computing elements may be configured to share the load associated with the failed surgical computing device or computing element. A notification, for example, a warning notification may be sent to a healthcare provider or a user indicating the failure of the device or the computing element and/or an indication that the processing of surgical data may be slowed down.

In an example, the compartmentalization of the ML algorithm may be dynamically scaled or adjusted with the resource availability. One or more ML compartments may be designated as related. In an example, such a relationship may be dynamic and may be updated (e.g., periodically updated). In an example, such a relationship may be defined prior to the surgical data processing, enabling the system to combine or separate the related ML aspects, as needed.

In an example, breadth and/or depth of surgical data on a surgical computing device (e.g., a surgical hub) may be altered or reduced, and at least one surgical data attribute to be analyzed by a ML algorithm may be scaled or adjusted. The alteration or reduction of surgical data and adjusting/scaling of at least one surgical data attribute to be analyzed by a ML algorithm may be based on availability of resource-time availability of the surgical computing device.

The availability of the resource-time relationship on a surgical computing device may be determined based on at least one of timeliness of a needed result, computational processing level associated with the surgical computing device or a computational memory associated with the surgical computing device, a network bandwidth between the surgical computing device and where the needed result it to be sent, one or more communication parameters (e.g., a throughput rate at the surgical computing device or a latency experienced by the surgical computing device), a risk level of functioning without obtaining the needed result, importance level of the surgical data or a surgical task associated with the surgical task, and/or availability of other data that may be used as a substitution.

The alteration or reduction of surgical data and adjusting/scaling of at least one surgical data attribute may be performed on the surgical computing device, for example, to balance the level of results achieved within a time slot and the resources the surgical computing device may make available, for example, within a time slot, as described herein.

The surgical computing device may scale at least one attribute associated with the ML algorithm based on balance of a level of a needed result, a time associated with the needed result, and availability of the computing resource within the time associated with the needed result. The at least one attribute may include a size of the surgical data, a number of surgical data variables, a frequency associated with the surgical data, an accuracy level associated with the surgical data, an ML algorithm type, a tolerable error associated with the ML algorithm, a number of stacking levels associated with the ML algorithm, and/or verification or checking of results.

In an example, the ML algorithm on a surgical computing device may be compartmentalized or clustered into a plurality of portions or parts. A magnitude and/or level of processing required may be determined for each of the small portions or parts of the ML algorithm.

Figure 16:
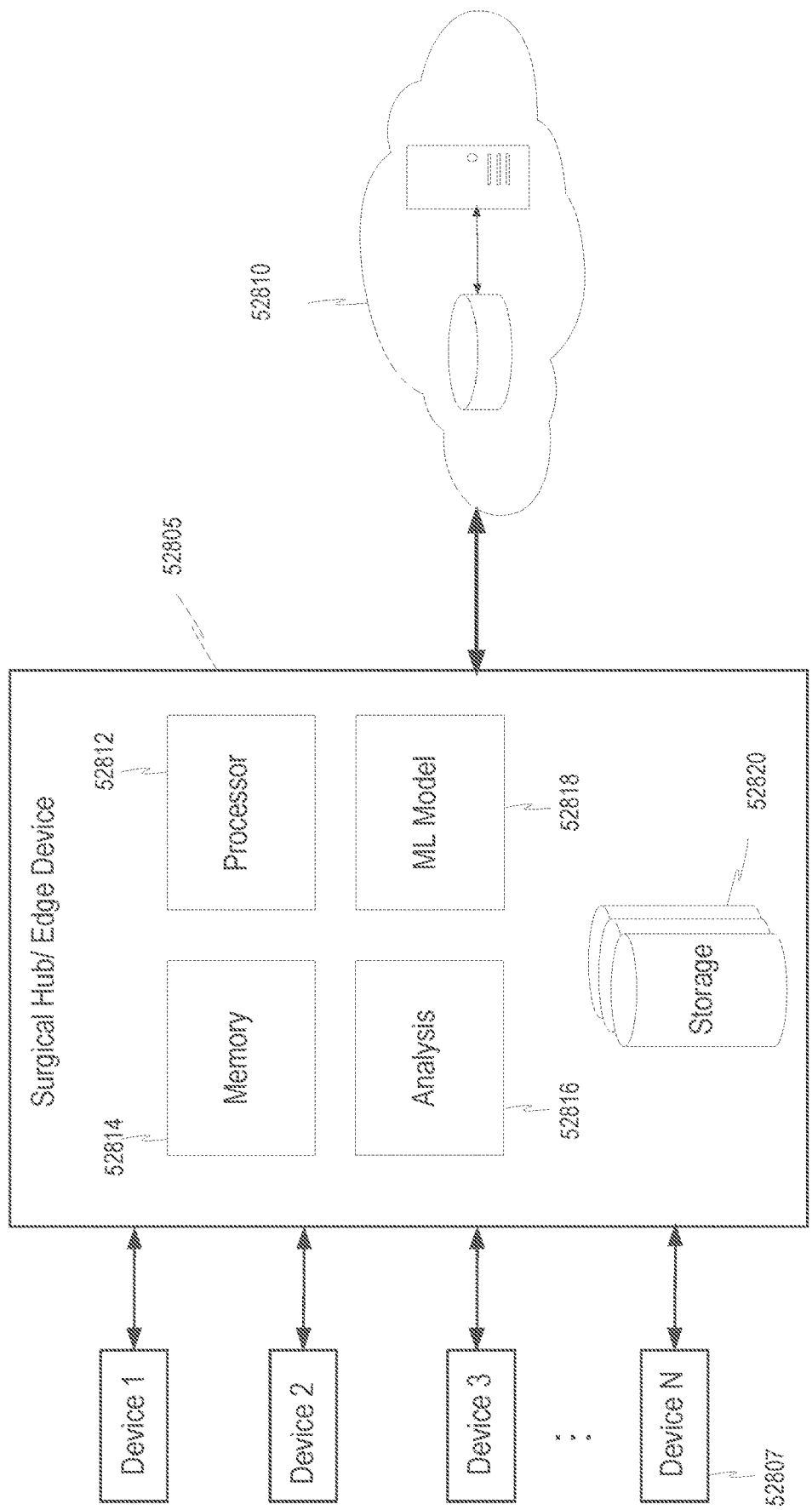
FIG. 16 shows an example of the surgical hub/edge device/edge device and the enterprise cloud server.

FIG. 16 illustrates an example of connectivity between the surgical computing device/edge computing device 52805 and the enterprise cloud server 52810 (e.g., enterprise cloud server). As illustrated in FIG. 16, the surgical computing device/edge computing device 52805 may include a processor 52812, a memory 52814 (e.g., a non-removable memory and/or a removable memory), an analysis subsystem 52816, a local machine learning model 52818, and/or a local storage subsystem 52820, among others. It will be appreciated that the surgical computing device/edge computing device 52805 may include any sub-combination of the foregoing elements/subsystems while remaining consistent with an embodiment.

The processor 52812 in the surgical computing device/edge computing device 52805 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52812 may perform data processing, authentication, input/output processing, and/or any other functionality that may enable surgical computing device/edge computing device 52805 to operate in an environment that is suitable for performing surgical procedures. The processor 52812 may be coupled with a transceiver (not shown). The processor 52812 may use the transceiver (not shown in the figure) to communicate with the enterprise cloud server 52810.

The memory 52814 in the surgical hub/edge device 52805 may be used to store where data was sent. For example, the memory may be used to recall that data was sent to an enterprise cloud server 52810. The memory may include a database and/or lookup table. The memory may include virtual memory which may be linked to servers located within the protected network.

The processor 52812 in the surgical computing device/edge computing device 52805 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52812 in the surgical computing device/edge computing device 52805 may access information from, and store data in an extended storage 52820. (e.g., a non-removable memory and/or the removable memory). In an example, the processor 52812 may access information from, and store data in, memory that is not physically located on the surgical computing device/edge computing device 52805, such as on a server or a secondary edge computing system (not shown).

An enterprise cloud server 52810 may include a processor, a memory (e.g., a non-removable memory and/or a removable memory), and/or a storage subsystem, among others. It will be appreciated that the enterprise cloud server 52810 may include any sub-combination of the foregoing elements/subsystems while remaining consistent with an embodiment.

The analysis module 52816 in the surgical hub/edge device 52805 may be used to determine when and where to send surgical data for processing, as described herein with respect to FIGS. 13, 14A, 14B, and 15. The analysis module 52816 may be used to determine when and how to perform compartmentalization of surgical data and ML algorithms, as described here with respect to FIG. 16.

Storage 52820 used in the surgical hub/edge device 52805 may be used to archive the results of what happened when data was sent to a particular processor. The storage 52820 may be a module included in the surgical hub/edge device 52805. In examples, the storage may be hardware (e.g., off-disk storage) accessible by the surgical hub/edge device 52805.

The local machine learning model 52818 in the surgical hub/edge device 52805 may be trained to determine where to send the data (e.g., to which processor) and/or how to divide the data for processing, as described with respect to FIGS. 13, 14A, and 15.

As illustrated in FIG. 16, Surgical hub/edge device 52805 may send data to and/or receive surgical data from the enterprise cloud server 52810. Surgical data may be based on measurements taken from sensors, actuators, robotic movements, biomarkers, surgeon biomarkers, visual aids, and/or the like. The wearables are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The measurements may be associated with one of more actuators located within the operating room. For example, measurements may be generated based on potentiometer readings located on a surgical instrument used as described with respect to FIG. 14B. Surgical data may relate to the cortisol level of surgeon. Surgical data may be collected based on these measurements and may help define the power, force, functional operation or behavior of a surgical instrument such as a smart hand-held stapler, which may be described in greater detail under the heading "Techniques for adaptive control of motor velocity of a surgical stapling and cutting instrument" in U.S. Pat. No. 10,881,399, filed Jun. 20, 2017, the disclosure of which is herein incorporated by reference in its entirety. The data may be used to provide situation awareness to a smart instrument such as a smart energy device, which may be described in greater detail under the heading "Method for smart energy device infrastructure" in U.S. patent Ser. No. 16/209,458, filed Dec. 4, 2018, the disclosure of which is herein incorporated by reference in its entirety.

For example, the surgeon may wear a sensing device (e.g., a wristwatch) that may determine the cortisol level of the surgeon based on a reading of the sweat produced by the surgeon. Such data may be anonymized (e.g., redacted, randomized, summarized, averaged, etc.) from being sent to the remove server.

Smart interconnected systems may be provided to define their relationship, cooperative behavior, or monitoring/storage of procedure details or the data described herein, which may be aggregated to develop better algorithms, trends, or procedure adaption based on the comparison of the outcomes with the choices. Such techniques may be described in greater detail under the heading "Method of hub communication, processing, display, and cloud analytics" in U.S. patent Ser. No. 16/209,416, filed Dec. 4, 2018, the disclosure of which is herein incorporated by reference in its entirety.

Figure 17:
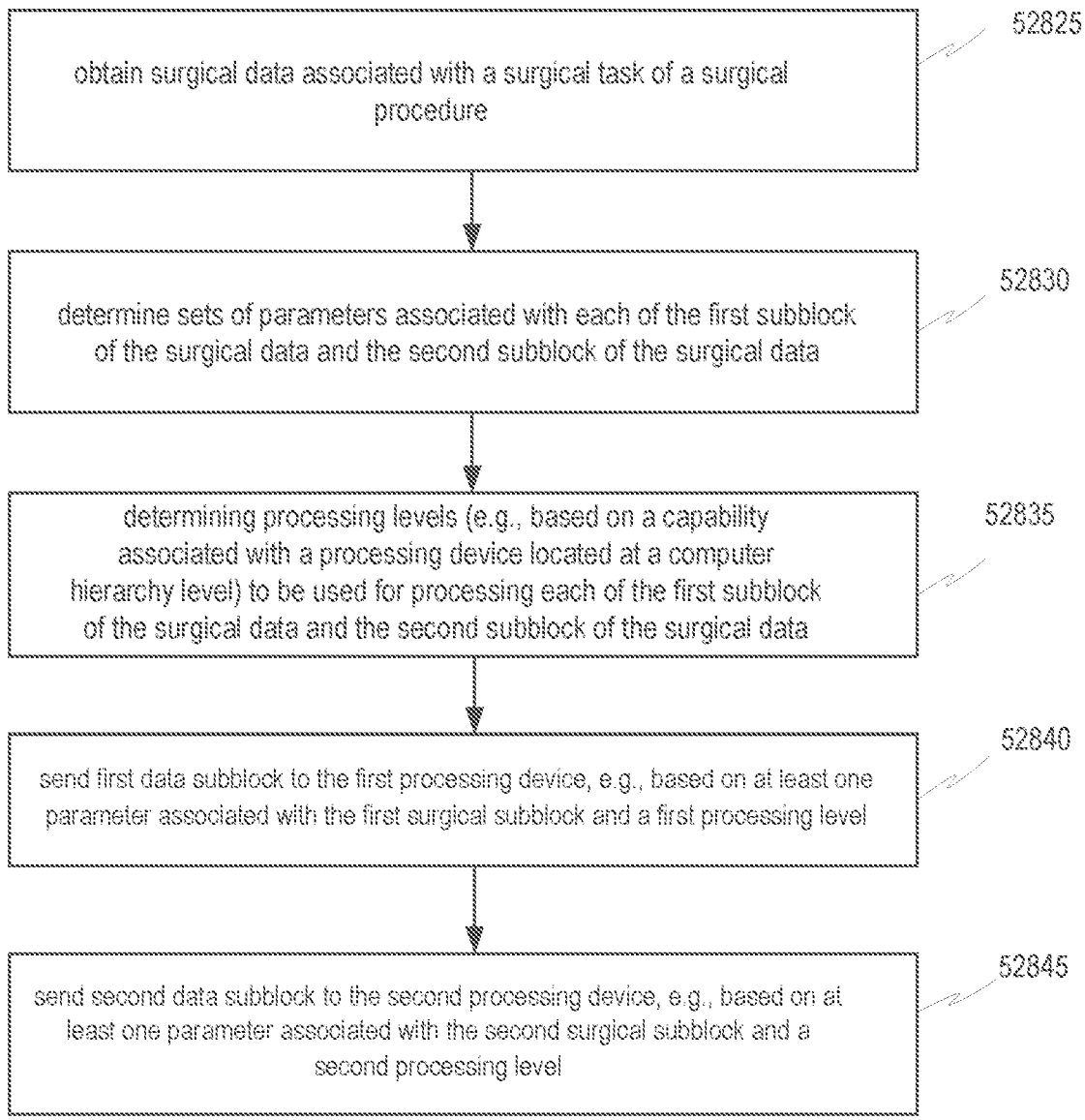
FIG. 17 shows an example of a flow chart of determining where to process data.

FIG. 17 shows an example of a flow chart for determining the location where surgical data may be sent for processing. At 52825, a device (e.g., a surgical hub, an edge server, a fog computing device, etc.) may obtain surgical data associated with a surgical task. The surgical data may be of a surgical data magnitude and a surgical data individuality level. The surgical data magnitude may be the extent the surgical data may be processed. The surgical data individuality level may be the individuality level of the surgical data to be processed.

At 52830, the surgical hub/edge device may determine sets of parameters associated with a first surgical data subblock of the surgical data and a second surgical subblock of the surgical data. For example, the surgical hub/edge device may determine a first set of parameters associated with a first surgical data subblock of the surgical data and a second set of parameters associated with a second surgical data subblock of the surgical data.

At 52835, the surgical hub/edge device may determine processing levels to be used for processing each of the first subblock of the surgical data and the second subblock of the surgical data. For example, the surgical hub/edge device may determine a first processing level to be used for processing the first surgical data subblock. The first processing level may be obtained based on a first capability associated with a first processing device located in a first computational hierarchal level of a healthcare provider's network. The surgical hub/edge device may also determine a second processing level to be used for processing the second surgical data subblock. The second processing level may be obtained based on a second capability associated with a second processing device located in a second computational hierarchy of the healthcare provider's network.

At 52840, the surgical hub/edge device may send the first surgical data subblock to the first processing device, for example, based on at least one of the first set of parameters associated with the first surgical data subblock and the first processing level. The first set of parameters associated with the first surgical data subblock may include, for example, a first surgical data magnitude associated with the first surgical data subblock, a first data granularity associated with the first surgical data subblock, a timeliness of a result associated with the first surgical data subblock.

At 52845, the surgical hub/edge device may send the second subblock to the second processing device, for example, based on at least one of the second set of parameters associated with the second surgical data subblock and second first processing level. The second set of parameters associated with the second surgical data subblock may include, for example, a second surgical data magnitude associated with the second surgical data subblock, a second data granularity associated with the second surgical data subblock, a timeliness of a result associated with the second surgical data subblock.

Figure 18:
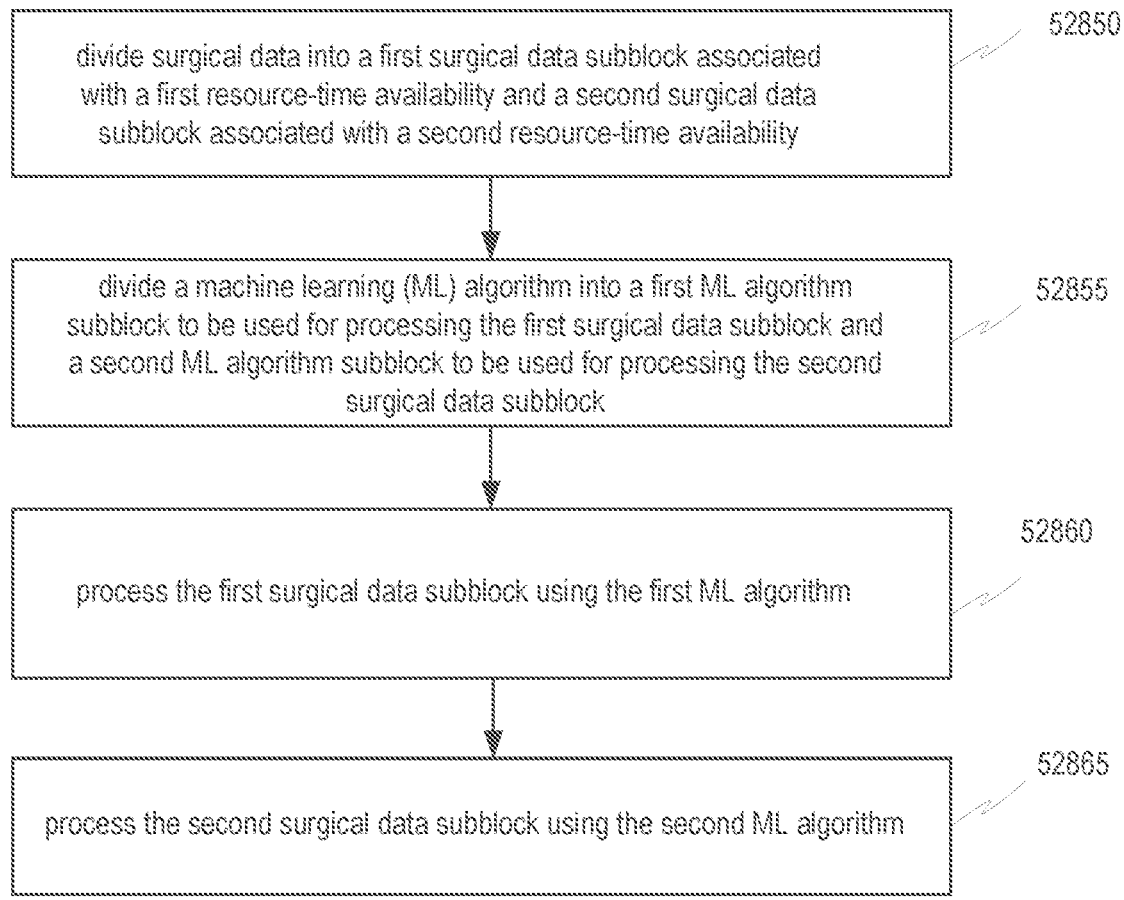
FIG. 18 shows an example of a flow chart of dividing ML algorithm into various subblocks for processing various parts of a dataset.

FIG. 18 shows an example of a flow chart of dividing ML algorithm into various subblocks for processing various parts of a dataset. At 52850, surgical data may be divided into a first surgical data subblock and a second surgical data subblock. The first portion of the surgical data may be associated with a first resource-time availability of a first device. The second portion of the surgical data may be associated with a second resource-time availability of a second device.

At 52855, a machine learning (ML) algorithm may be divided into a first ML algorithm subblock and a second ML algorithm subblock. The first portion of the ML algorithm may be used for processing the first portion of surgical data in accordance with the first resource-time availability. The second portion of the ML algorithm may be used for processing the second portion of surgical data in accordance with the second resource-time availability.

At 52860, the first portion of the surgical data may be processed using the first portion of the ML algorithm. At 52860, the second portion of the surgical data may be processed using the second portion of the ML algorithm.

Figure 19:
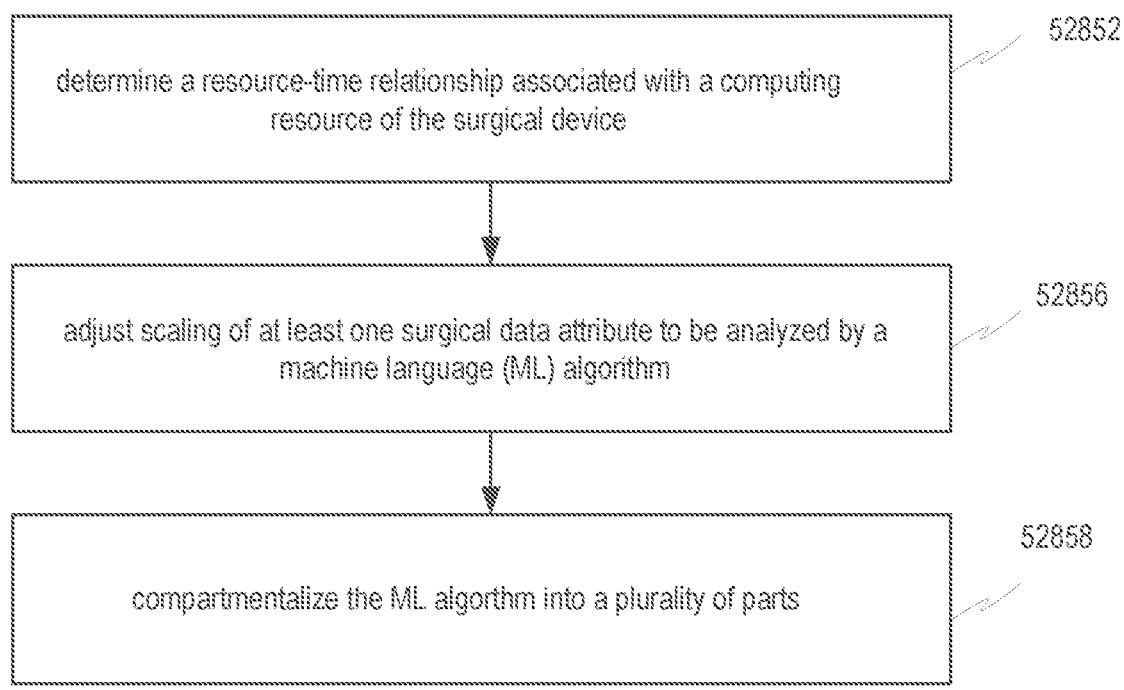
FIG. 19 shows an example of a flow chart of compartmentalization of ML algorithm processing of local data.

FIG. 19 shows an example of a flow chart of compartmentalization of ML algorithm processing of local data. At 52852, a surgical device may determine a resource-time relationship associated with a computing resource of the surgical device. The availability of the resource-time relationship on a surgical computing device may be determined based on at least one of timeliness of a needed result, computational processing level associated with the surgical computing device or a computational memory associated with the surgical computing device, a network bandwidth between the surgical computing device and where the needed result it to be sent, one or more communication parameters (e.g., a throughput rate at the surgical computing device or a latency experienced by the surgical computing device), a risk level of functioning without obtaining the needed result, importance level of the surgical data or a surgical task associated with the surgical task, and/or availability of other data that may be used as a substitution.

At 52856, the surgical device may adjust scaling of at least one data attribute to be analyzed by a machine language (ML) algorithm. The adjusting scaling of at least one surgical data attribute may be performed on the surgical computing device, for example, to balance the level of results achieved within a time slot and the resources the surgical computing device may make available, for example, within a time slot.

At 52858, the surgical computing device may compartmentalize the ML algorithm into a plurality of parts. A magnitude and/or level of processing required may be determined for each of the small portions or parts of the ML algorithm. For example, the magnitude and/or the level of processing required may be based on the computing resources available.

The invention claimed is:

1. A surgical computing device comprising:
a processor configured to:
obtain surgical data associated with a surgical task of a surgical procedure;
determine a first set of parameters associated with a first surgical data subblock of the surgical data and a second set of parameters associated with a second surgical data subblock of the surgical data;
determine a first processing level to be used for processing the first surgical data subblock, wherein the first processing level is obtained based on a first capability associated with a first processing device located in a first computational hierarchal level of a healthcare provider's network;
determine a second processing level to be used for processing the second surgical data subblock, wherein the second processing level is obtained based on a second capability associated with a second processing device located in a second computational hierarchy of the healthcare provider's network;
send the first surgical data subblock to the first processing device, wherein the first surgical data subblock is sent for processing to the first processing device based on at least one of the first set of parameters associated with the first surgical data subblock and the first processing level; and
send the second surgical data subblock to the second processing device, wherein the second surgical data subblock is sent for processing to the second processing level of the surgical data based on at least one of the second set of parameters associated with the second surgical data subblock and the second processing level.

2. The surgical computing device of claim 1, wherein the first set of the parameters associated with the first surgical data subblock comprises at least one of a first surgical data magnitude associated with the first surgical data subblock, a first data granularity associated with the first surgical data subblock, a timeliness of a result associated with the first surgical data subblock.

3. The surgical computing device of claim 1, wherein each of the second set of the parameters associated with the second surgical data subblock comprises at least one of a magnitude of the second surgical data subblock, timeliness of result associated with the second surgical data subblock.

4. The surgical computing device of claim 1, wherein the first processing device is located within protected part of the healthcare provider's network, and the second processing device is located within unprotected part of the healthcare provider's network.

5. The surgical computing device of claim 4, wherein the first processing device is a first edge server or a fog computing device located within protected part of the healthcare provider's network, and the second processing device is second edge server or an enterprise cloud server, wherein the second edge server is located within unprotected part of the healthcare provider's network.

6. The surgical computing device of claim 1, wherein the first capability associated with the first processing device or the second capability associated with the second processing device comprises at least one of a processing power, a memory size, or a time taken to process surgical data.

7. The surgical computing device of claim 1, wherein time taken to process the first surgical data subblock by the first processing device is lower than time taken to process the second surgical data subblock by the second processing device.

8. The surgical computing device of claim 1, wherein the surgical computing device is one of a surgical hub, an edge server, or a fog computing device.

9. A surgical data processing method implemented on a surgical computing device, the method comprising:
obtaining surgical data associated with a surgical task of a surgical procedure;
determining a first set of parameters associated with a first surgical data subblock of the surgical data and a second set of parameters associated with a second surgical data subblock of the surgical data;
determining a first processing level to be used for processing the first surgical data subblock, wherein the first processing level is obtained based on a first capability associated with a first processing device located in a first computational hierarchal level of a healthcare provider's network;
determining a second processing level to be used for processing the second surgical data subblock, wherein the second processing level is obtained based on a second capability associated with a second processing device located in a second computational hierarchy of the healthcare provider's network;
sending the first surgical data subblock to the first processing device, wherein the first surgical data subblock is sent for processing to the first processing device based on at least one of the first set of parameters associated with the first surgical data subblock and the first processing level; and
sending the second surgical data subblock to the second processing device, wherein the second surgical data subblock is sent for processing to the second processing level of the surgical data based on at least one of the second set of parameters associated with the second surgical data subblock and the second processing level.

10. The method of claim 9, wherein the first set of the parameters associated with the first surgical data subblock comprises at least one of a first surgical data magnitude associated with the first surgical data subblock, a first data granularity associated with the first surgical data subblock, a timeliness of a result associated with the first surgical data subblock.

11. The method of claim 9, wherein each of the second set of the parameters associated with the second surgical data subblock comprises at least one of a magnitude of the second surgical data subblock, timeliness of result associated with the second surgical data subblock.

12. The method of claim 9, wherein the first processing device is located within protected part of the healthcare provider's network, and the second processing device is located within unprotected part of the healthcare provider's network.

13. The method of claim 12, wherein the first processing device is a first edge server or a fog computing device located within protected part of the healthcare provider's network, and the second processing device is second edge server or an enterprise cloud server, wherein the second edge server is located within unprotected part of the healthcare provider's network.

14. The method of claim 9, wherein the first capability associated with the first processing device or the second capability associated with the second processing device comprises at least one of a processing power, a memory size, or a time taken to process surgical data.

15. The method of claim 9, wherein time taken to process the first surgical data subblock by the first processing device is lower than time taken to process the second surgical data subblock by the second processing device.

16. The method of claim 9, wherein the surgical computing device is one of a surgical hub, an edge server, or a fog computing device.

* * * * *